(12) United States Patent
Kassab et al.

(10) Patent No.: US 8,147,424 B2
(45) Date of Patent: Apr. 3, 2012

(54) DEVICES, SYSTEMS, AND METHODS FOR OBTAINING BIOPSY TISSUE SAMPLES

(75) Inventors: Ghassan S. Kassab, Indianapolis, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 0 days.

(21) Appl. No.: 12/597,852

(22) PCT Filed: Apr. 16, 2008

(86) PCT No.: PCT/US2008/060513
§ 371 (c)(1),
(2), (4) Date: Apr. 13, 2010

(87) PCT Pub. No.: WO2008/134247
PCT Pub. Date: Nov. 6, 2008

(65) Prior Publication Data
US 2010/0228221 A1  Sep. 9, 2010

Related U.S. Application Data

(60) Provisional application No. 60/914,452, filed on Apr. 27, 2007, provisional application No. 60/817,421, filed on Jun. 30, 2006.

(30) Foreign Application Priority Data

Jun. 29, 2007 (WO) ................ PCT/US2007/015207
Feb. 5, 2008 (WO) ................ PCT/US2008/053061
Mar. 12, 2008 (WO) ................ PCT/US2008/056666

(51) Int. Cl.
*A61B 5/00* (2006.01)

(52) U.S. Cl. .................................................... 600/564
(58) Field of Classification Search ........... 600/564–568
See application file for complete search history.

(56) References Cited

U.S. PATENT DOCUMENTS

| | | | |
|---|---|---|---|
| 3,583,404 A | 6/1971 | McWhorter | |
| 3,630,207 A | 12/1971 | Kahn et al. | |
| 4,991,578 A | 2/1991 | Cohen | |
| 5,195,968 A | 3/1993 | Lundquist et al. | |
| 5,292,332 A | 3/1994 | Lee | |
| 5,407,430 A | 4/1995 | Peters | |
| 5,715,817 A | 2/1998 | Stevens-Wright et al. | |
| 5,782,764 A * | 7/1998 | Werne ........................... | 600/411 |
| 5,810,744 A * | 9/1998 | Chu et al. ...................... | 600/567 |
| 5,928,164 A * | 7/1999 | Burbank et al. .............. | 600/567 |

(Continued)

OTHER PUBLICATIONS

PCT/US2008/053061, International Searching Authority, PCT Search Report, dated Oct. 1, 2008.

(Continued)

*Primary Examiner* — Max Hindenburg
*Assistant Examiner* — Michael C Stout
(74) *Attorney, Agent, or Firm* — Ice Miller LLP

(57) ABSTRACT

Devices, systems, and methods for accessing tissue in a minimally invasive manner and taking a biopsy tissue sample therefrom are disclosed. At least some of the embodiments disclosed herein enable a tissue sample to be taken from the external surface of the heart in a non-invasive manner. In addition, various disclosed embodiments provide devices, systems and methods for accessing the pericardial space through the interior of the heart and engaging the epicardial surface and removing a tissue sample therefrom for diagnostic purposes through the use of suction.

49 Claims, 36 Drawing Sheets

U.S. PATENT DOCUMENTS

| | | |
|---|---|---|
| 5,972,013 A | 10/1999 | Schmidt |
| 5,980,469 A * | 11/1999 | Burbank et al. ............ 600/567 |
| 6,083,237 A * | 7/2000 | Huitema et al. ............ 606/180 |
| 6,113,611 A | 9/2000 | Allen et al. |
| 6,338,345 B1 | 1/2002 | Johnson et al. |
| 6,500,167 B1 | 12/2002 | Webster, Jr. |
| 6,595,982 B2 | 7/2003 | Sekino et al. |
| 6,626,930 B1 | 9/2003 | Allen et al. |
| 6,663,633 B1 | 12/2003 | Pierson, III |
| 6,692,458 B2 | 2/2004 | Forman et al. |
| 6,773,418 B1 | 8/2004 | Sharrow et al. |
| 6,776,784 B2 | 8/2004 | Ginn |
| 6,837,893 B2 | 1/2005 | Miller |
| 6,890,295 B2 | 5/2005 | Michels |
| 6,918,890 B2 | 7/2005 | Schmidt |
| 6,991,616 B2 | 1/2006 | Bencini et al. |
| 7,029,468 B2 | 4/2006 | Honebrink |
| 7,081,125 B2 | 7/2006 | Edwards et al. |
| 7,326,231 B2 | 2/2008 | Phillips et al. |
| 7,398,781 B1 * | 7/2008 | Chin ............................ 128/898 |
| 7,842,068 B2 | 11/2010 | Ginn |
| 7,931,628 B2 | 4/2011 | Zhu et al. |
| 7,942,897 B2 | 5/2011 | Lafontaine |
| 7,959,580 B2 * | 6/2011 | McCullough et al. ........ 600/566 |
| 2002/0072768 A1 | 6/2002 | Ginn |
| 2002/0091354 A1 | 7/2002 | Navia, Sr. |
| 2002/0165561 A1 | 11/2002 | Ainsworth |
| 2002/0168317 A1 | 11/2002 | Daighighian et al. |
| 2003/0009145 A1 | 1/2003 | Struijker-Boudier et al. |
| 2003/0109852 A1 | 6/2003 | Peterson et al. |
| 2003/0216759 A1 * | 11/2003 | Burbank et al. ............ 606/157 |
| 2003/0225420 A1 | 12/2003 | Wardle |
| 2004/0010216 A1 | 1/2004 | Zhu et al. |
| 2004/0018228 A1 | 1/2004 | Fischell et al. |
| 2004/0059280 A1 | 3/2004 | Makower et al. |
| 2004/0086479 A1 | 5/2004 | Grinstaff et al. |
| 2004/0087938 A1 | 5/2004 | Leckrone et al. |
| 2004/0102804 A1 * | 5/2004 | Chin ............................ 606/190 |
| 2004/0167558 A1 | 8/2004 | Igo et al. |
| 2004/0230131 A1 | 11/2004 | Kassab et al. |
| 2005/0054994 A1 | 3/2005 | Cioanta et al. |
| 2005/0113760 A1 | 5/2005 | Chachques et al. |
| 2005/0148818 A1 * | 7/2005 | Mesallum ..................... 600/116 |
| 2005/0159677 A1 * | 7/2005 | Shabaz et al. ................. 600/567 |
| 2005/0256450 A1 | 11/2005 | Palasis et al. |
| 2005/0261673 A1 | 11/2005 | Bonner et al. |
| 2005/0272975 A1 | 12/2005 | McWeeney et al. |
| 2006/0106288 A1 | 5/2006 | Roth et al. |
| 2006/0106442 A1 | 5/2006 | Richardson et al. |
| 2006/0173377 A1 * | 8/2006 | McCullough et al. ........ 600/566 |
| 2006/0184153 A1 * | 8/2006 | Mark et al. .................... 604/500 |
| 2006/0207612 A1 | 9/2006 | Jackson et al. |
| 2006/0217764 A1 | 9/2006 | Abbott et al. |
| 2006/0240133 A1 | 10/2006 | Munz et al. |
| 2006/0247672 A1 * | 11/2006 | Vidlund et al. ............... 606/190 |
| 2006/0270975 A1 | 11/2006 | Savage |
| 2007/0010708 A1 | 1/2007 | Ness |
| 2007/0010793 A1 | 1/2007 | Callas et al. |
| 2008/0045859 A1 * | 2/2008 | Fritsch et al. ................. 600/567 |
| 2008/0228104 A1 * | 9/2008 | Uber et al. .................... 600/567 |
| 2010/0280407 A1 * | 11/2010 | Polster .......................... 600/566 |

OTHER PUBLICATIONS

PCT/US2008/053061, International Searching Authority, Written Opinion, dated Oct. 1, 2008.

PCT/US2008/060513, International Searching Authority, PCT Search Report, dated Sep. 2, 2008.

PCT/US2008/060513, International Searching Authority, Written Opinion, dated Sep. 2, 2008.

PCT/US2007/015207, International Searching Authority, PCT Search Report, dated Sep. 11, 2008.

PCT/US2007/015207, International Searching Authority, Written Opinion, dated Sep. 11, 2008.

PCT/US2008/056666, International Searching Authority, PCT Search Report, dated Aug. 29, 2008.

PCT/US2008/056666, International Searching Authority, Written Opinion, dated Aug. 29, 2008.

PCT/US2008/073004, International Searching Authority, PCT Search Report, dated Nov. 14, 2008.

PCT/US2008/073004, International Searching Authority, Written Opinion, dated Nov. 14, 2008.

Huang, Guofeng, Engineering RGD-Modified Liposomes for Targeted Drug Delivery to Activated Platelets, Doctoral Thesis, Aug. 2006, Case Western Reserve University, Ohio.

Uchida et al. "Angiogenic therapy of acute myocardial infarction by intrapericardial injection of . . . " American Heart Journal, vol. 130, No. 6, pp. 1182-1188 (Dec. 1995).

* cited by examiner

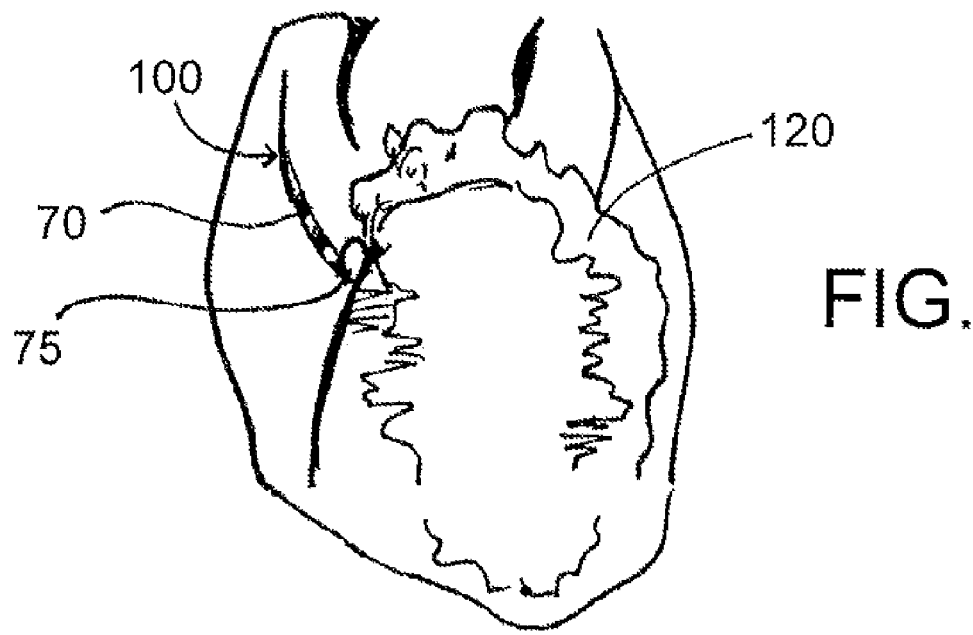
FIG. 3A
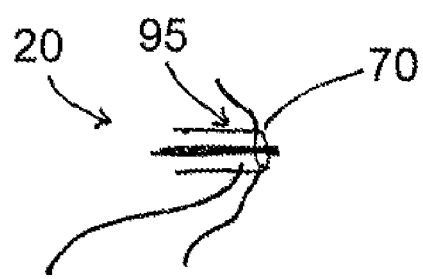
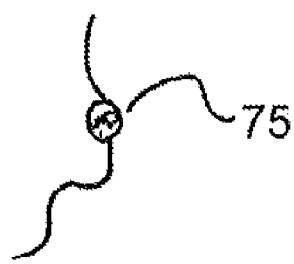
FIG. 3B

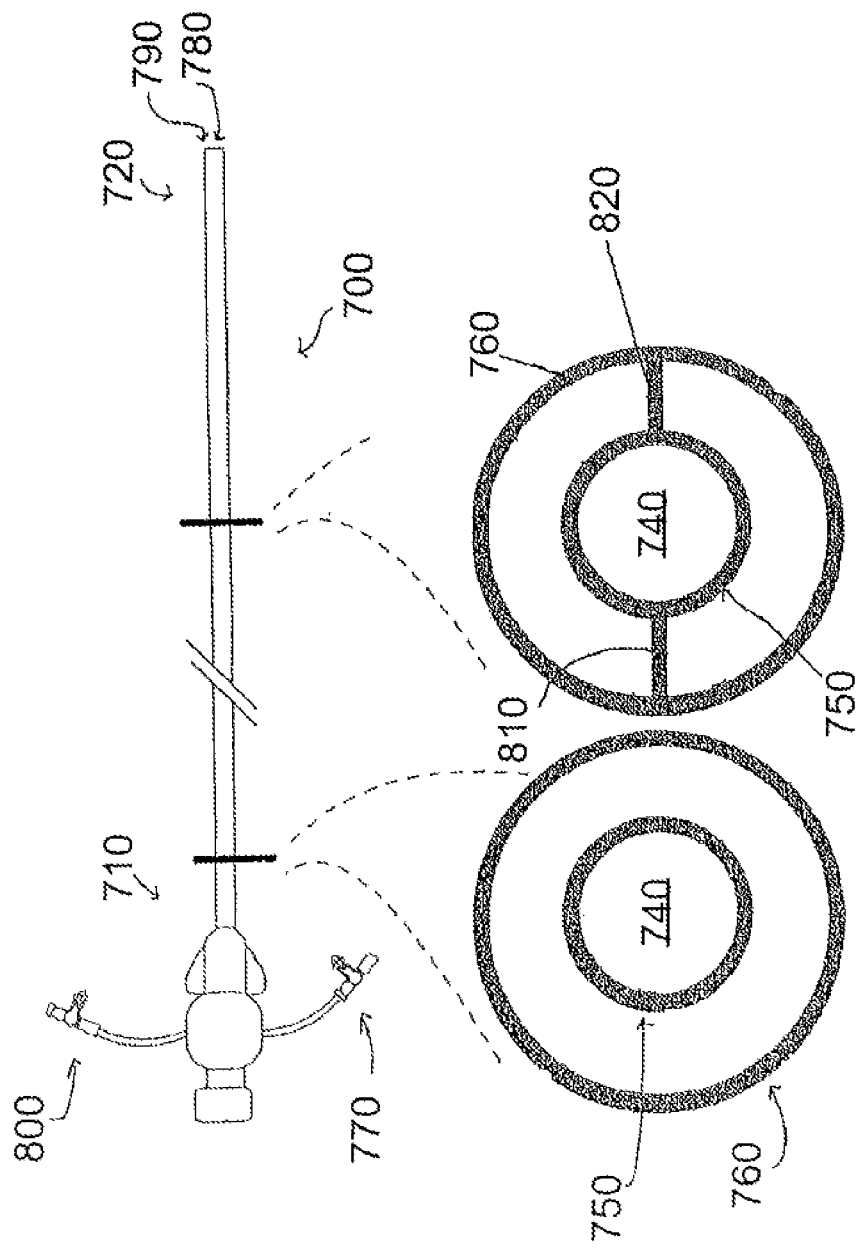

FIG. 6A
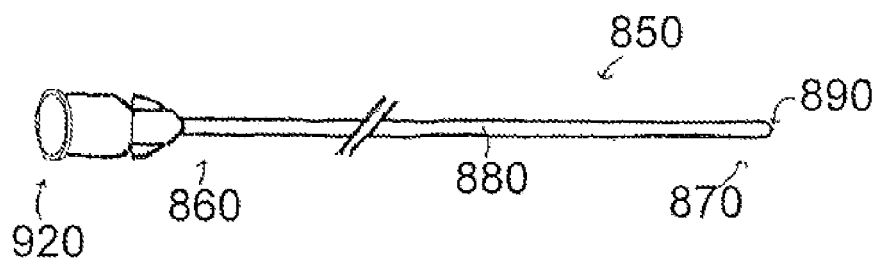
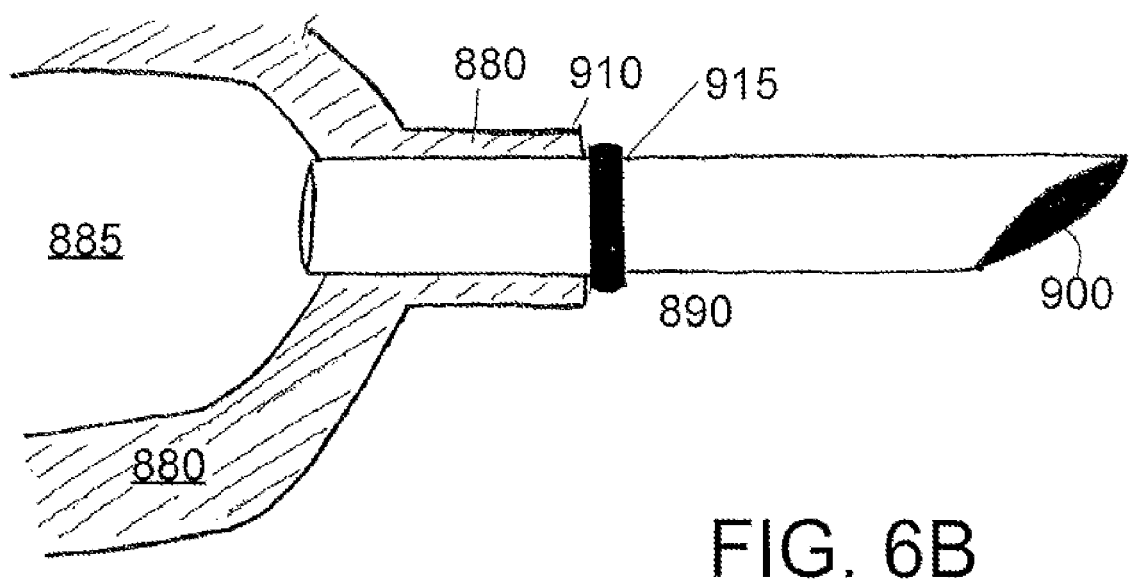
FIG. 6B
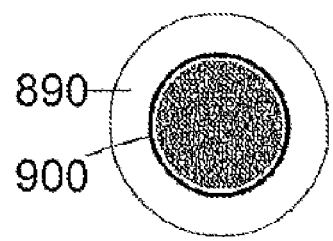
FIG. 6C

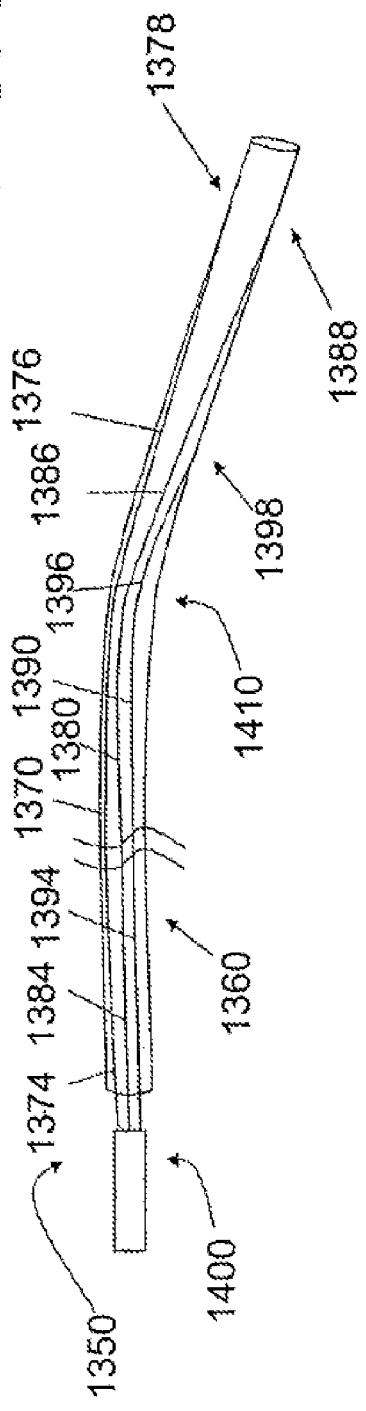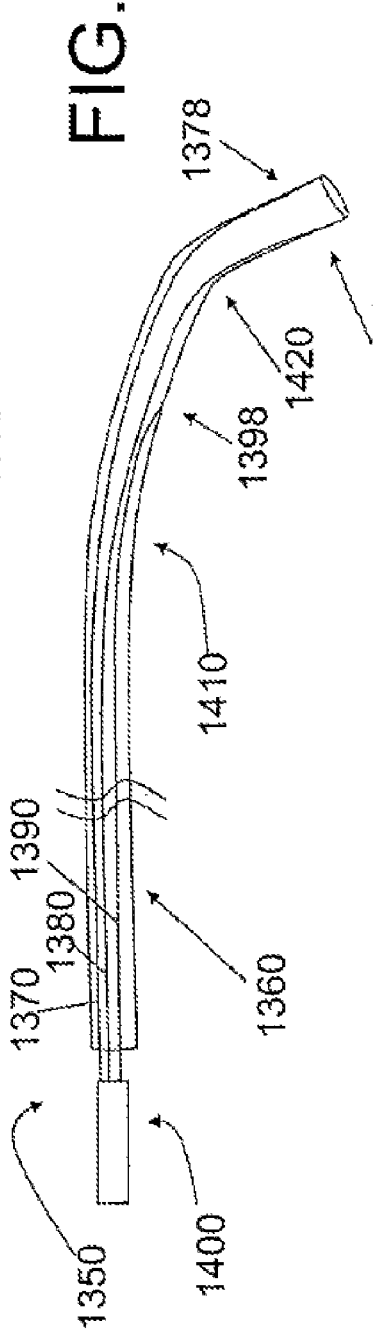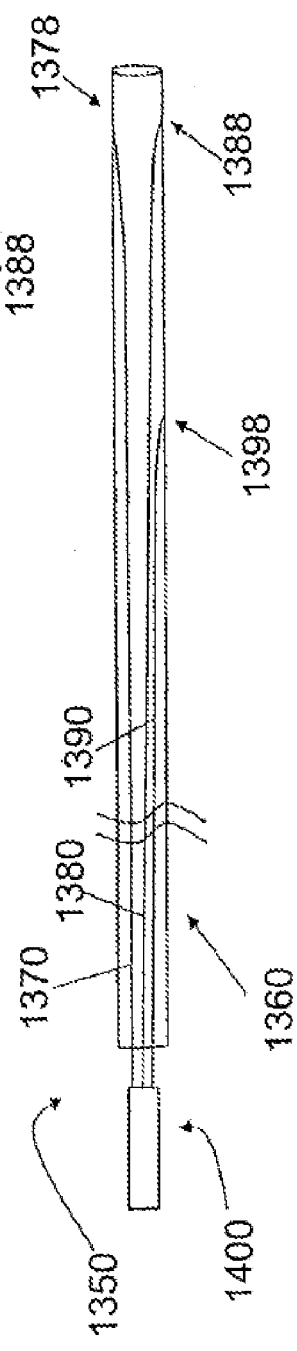

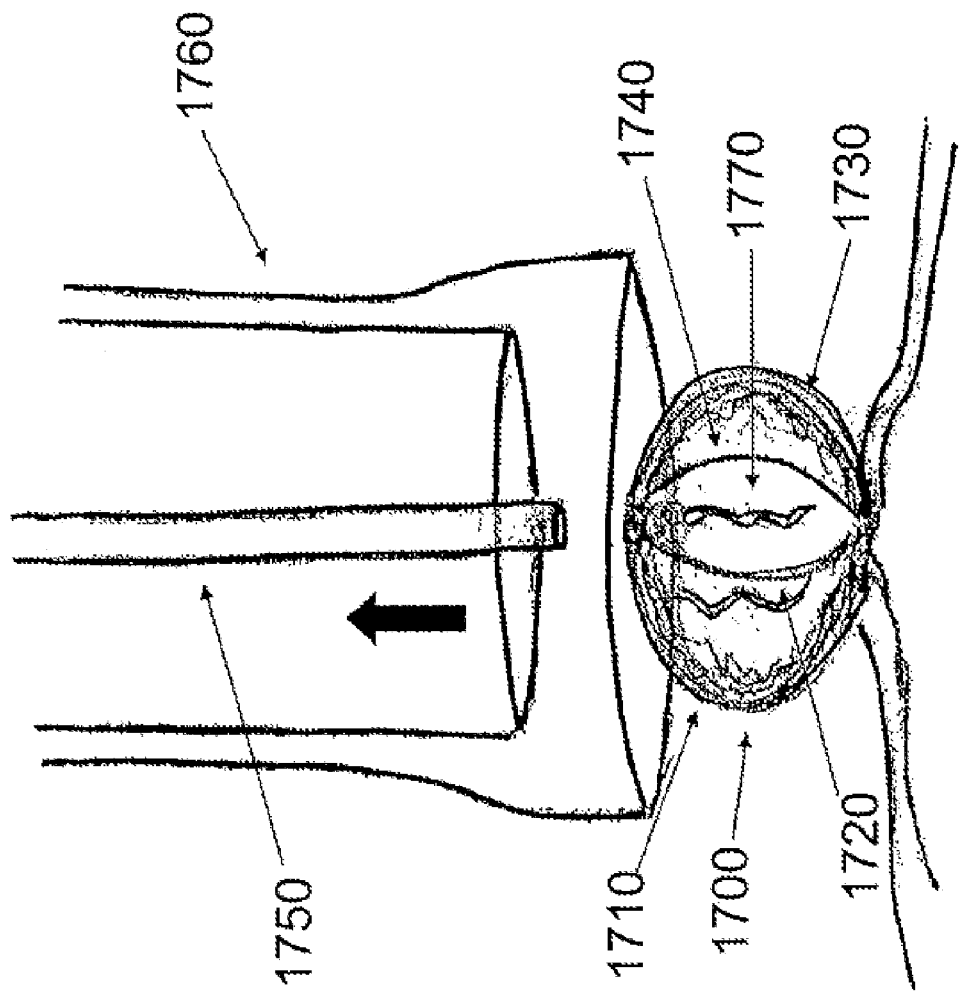

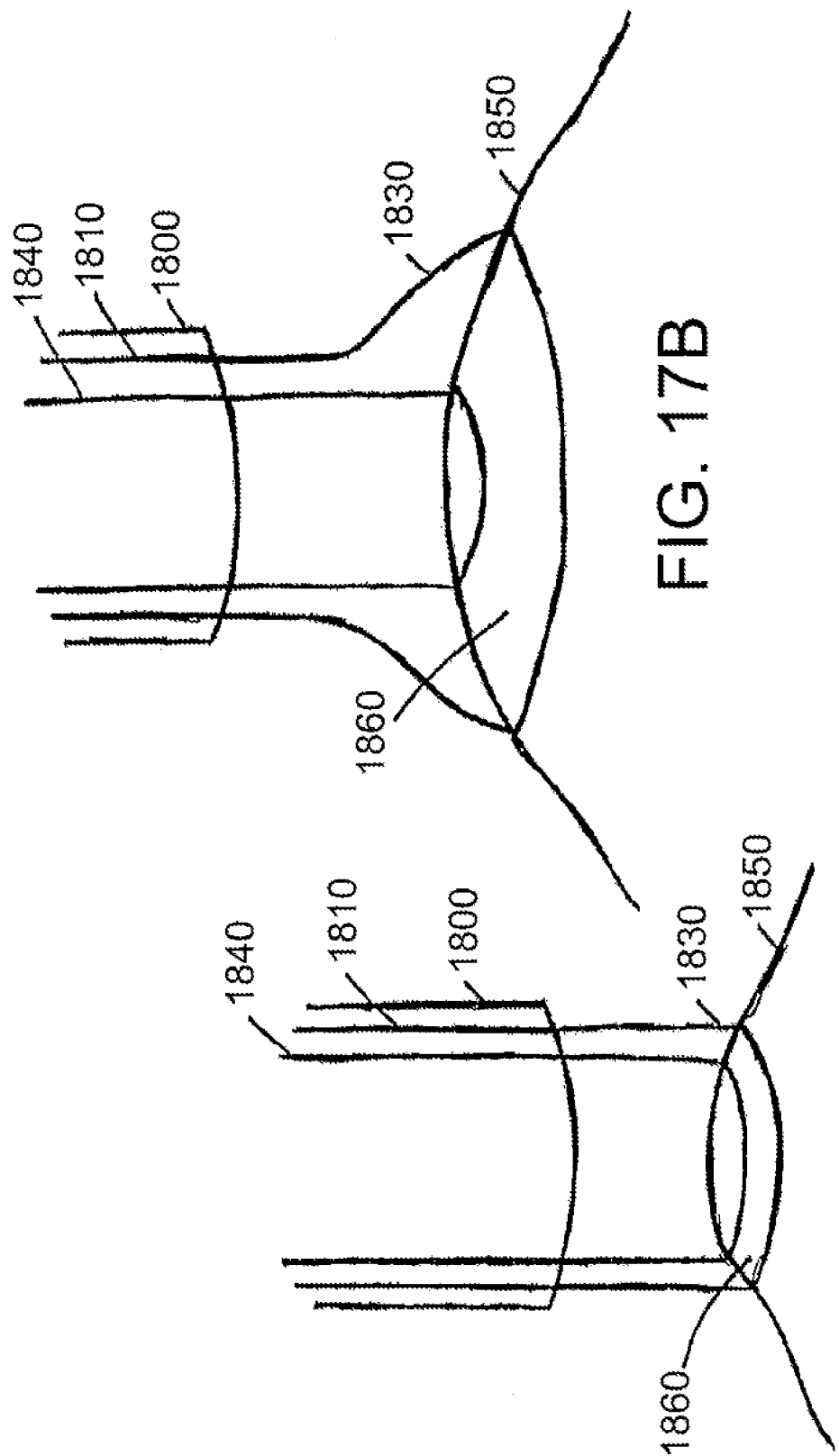

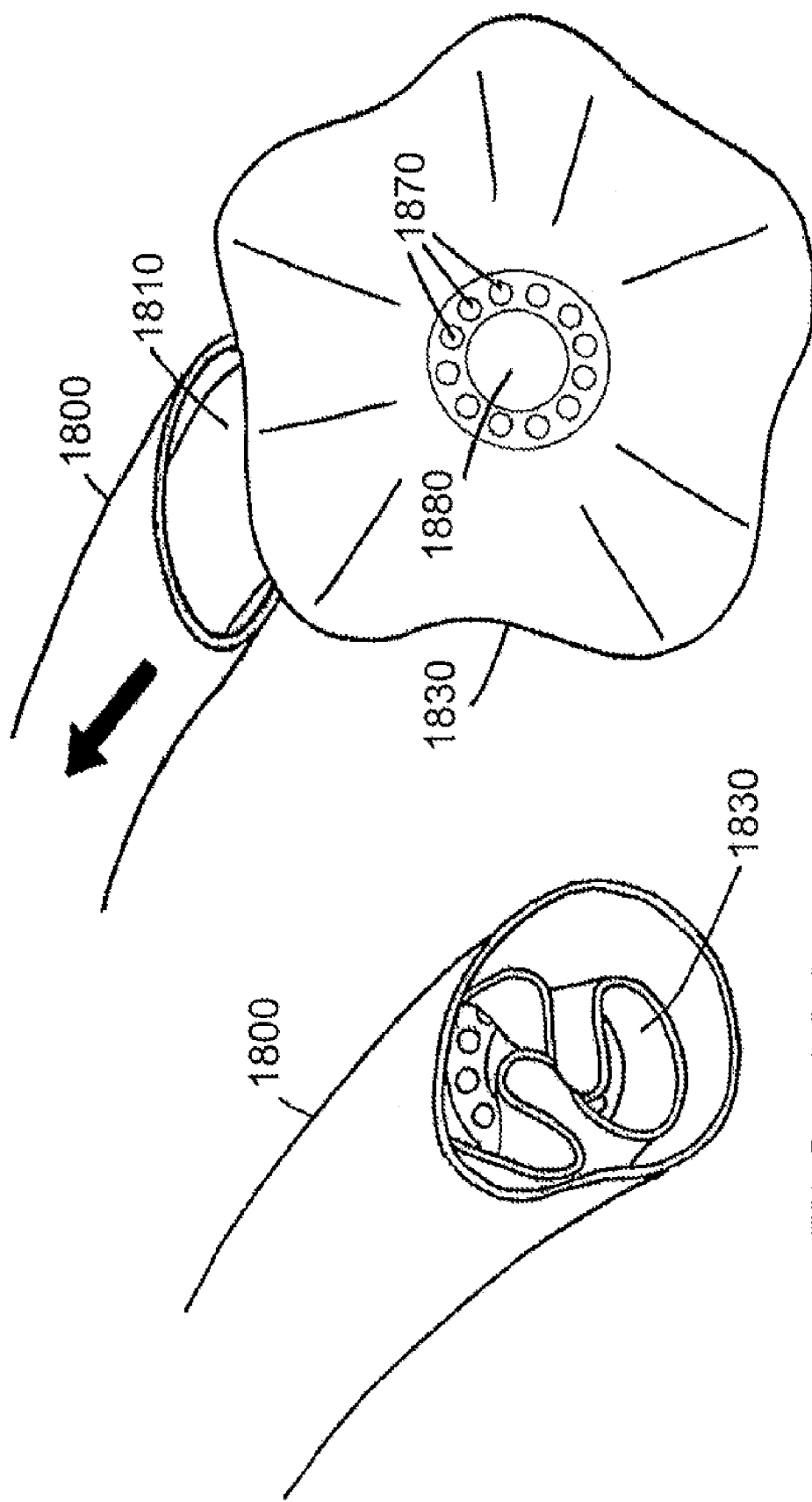

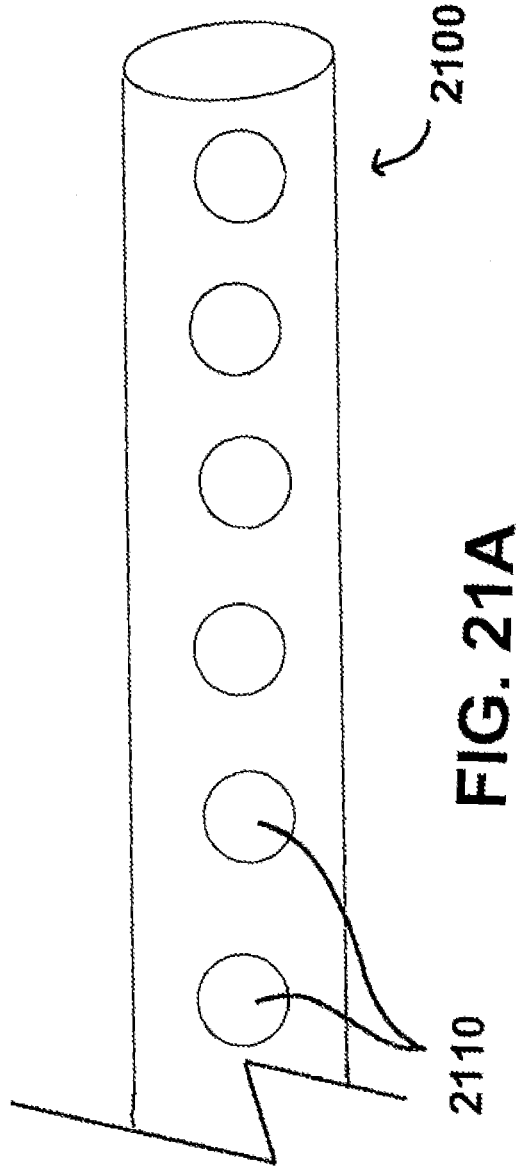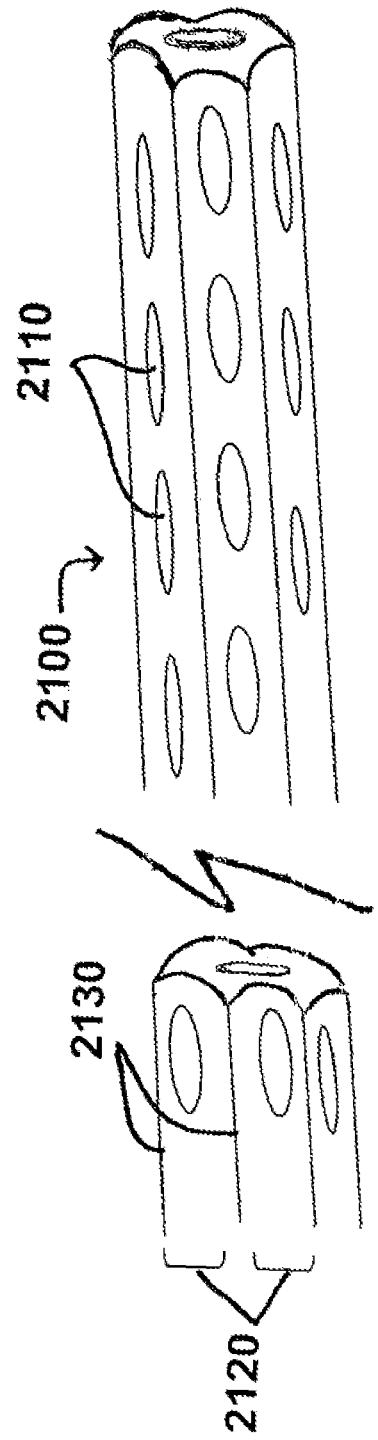
FIG. 21A
FIG. 21B

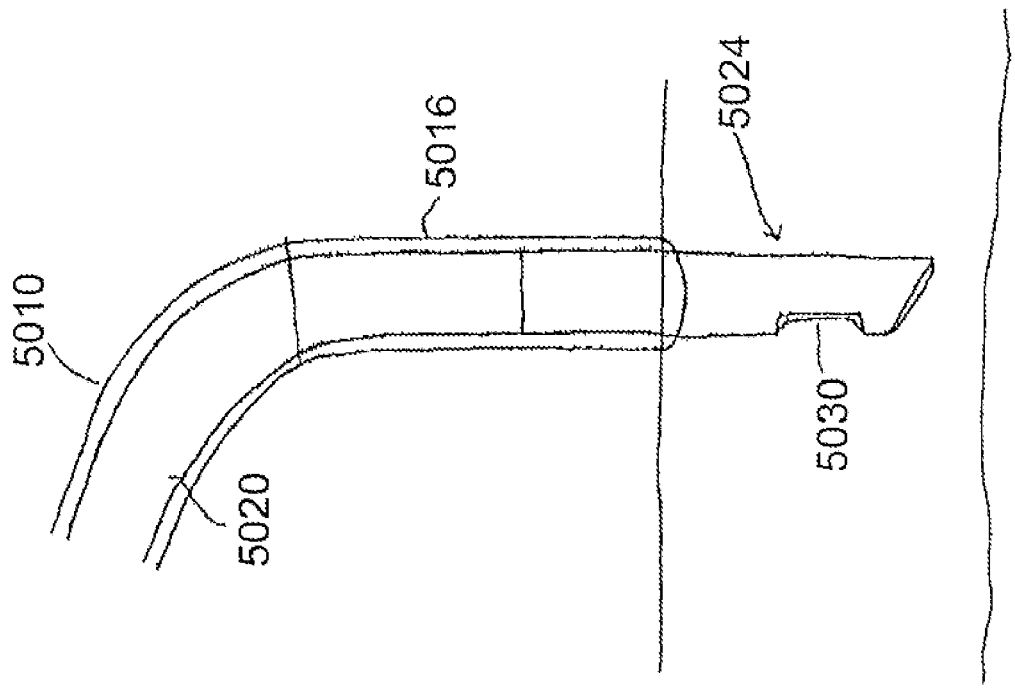
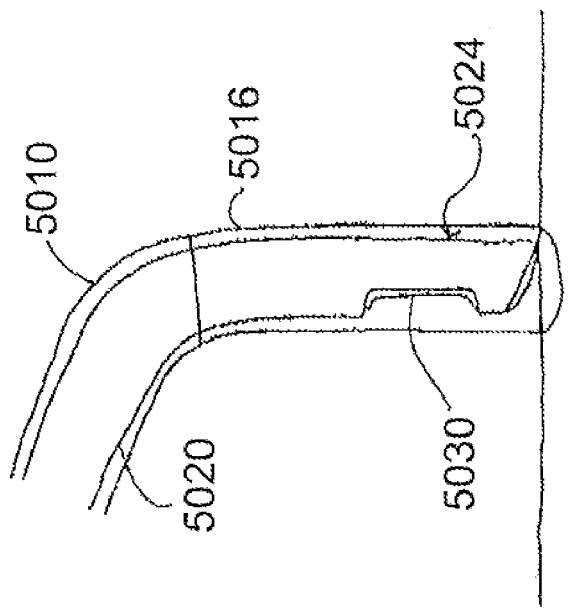

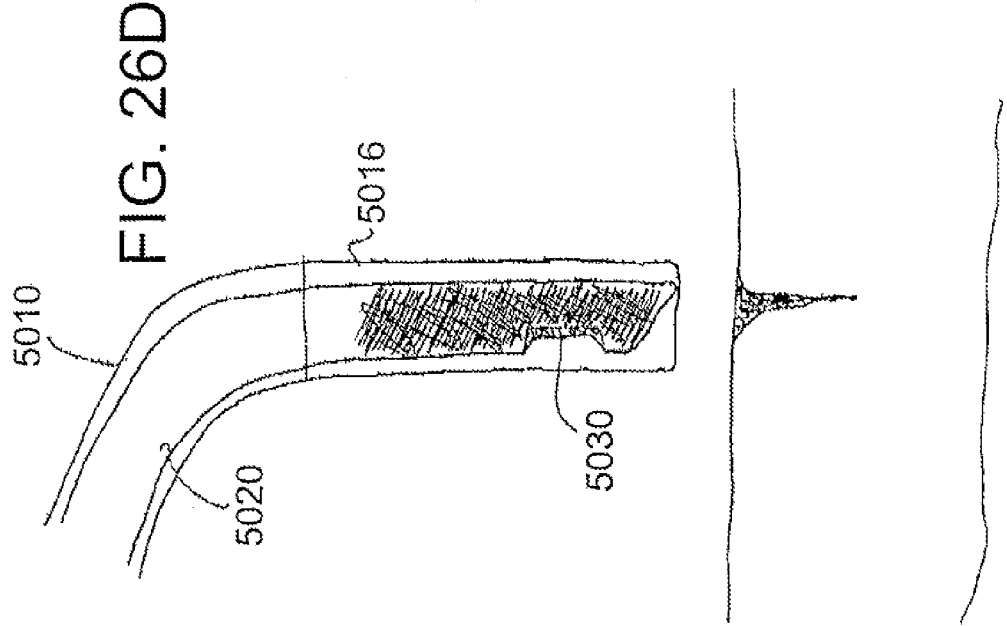
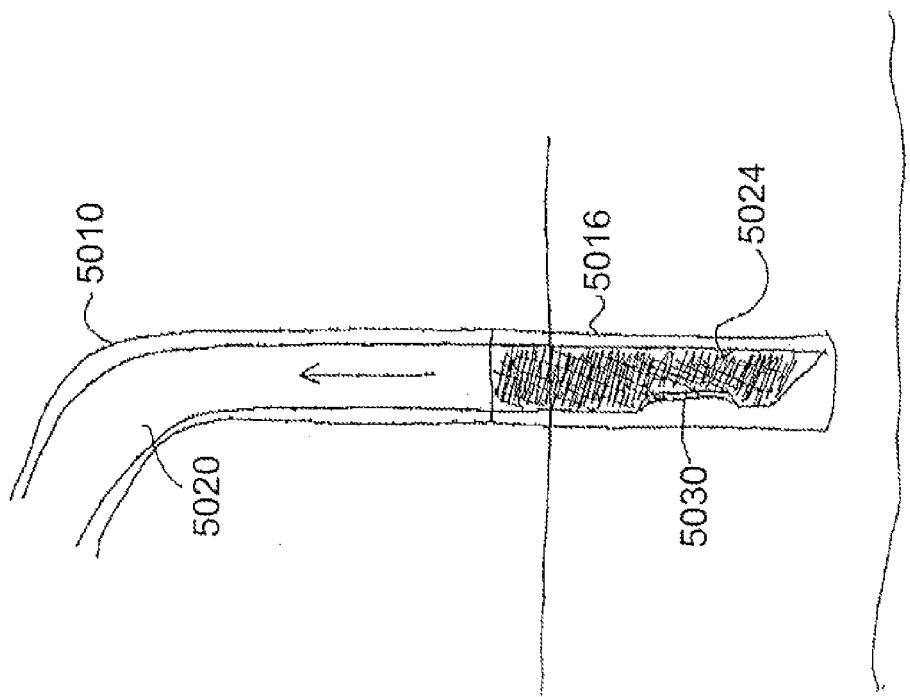

DEVICES, SYSTEMS, AND METHODS FOR OBTAINING BIOPSY TISSUE SAMPLES

The present application (a) is related to, claims the priority benefit of, and is a U.S. §371 national stage patent application of, International Patent Application No. PCT/US2008/060513, filed Apr. 16, 2008, which is related to, claims the priority benefit of and in at least some designated countries should be considered a continuation-in-part application of International Patent Application No. PCT/US2008/056666, filed Mar. 12, 2008, which is related to, claims the priority benefit of and in at least some designated countries should be considered a continuation-in-part application of, International Patent Application No. PCT/US2008/053061, filed Feb. 5, 2008, which is related to, claims the priority benefit of, and in at least some designated countries should be considered a continuation-in-part application of, International Application Serial No. PCT/US2007/015207, filed Jun. 29, 2007, which claims priority to U.S. Provisional Patent Application Ser. No. 60/914,452, filed Apr. 27, 2007, and U.S. Provisional Patent Application Ser. No. 60/817,421, filed Jun. 30, 2006, and (b) is related to, and claims the priority benefit of, U.S. Provisional Patent Application Ser. No. 60/914,452, filed Apr. 27, 2007. The contents of each of these applications are hereby incorporated by reference in their entirety into this disclosure.

BACKGROUND

Historically, advances in non-invasive diagnostic techniques such as echocardiography, computed tomography, and magnetic resonance imaging ("MRI") significantly reduced the use of diagnostic endomyocardial biopsy ("EMB") in practice. Despite this however, EMB remains a necessary diagnostic procedure because specific myocardial disorders that have unique prognoses and treatment are difficult to diagnose by noninvasive methods. Further, recent advantages in molecular biology and biomedical markers have once again increased the need of EMB. Specifically, analysis of a myocardial biopsy specimen may provide essential information on cardiac pathogensis. (Pawlak, Walczak et al. 2005)

Indications for endomyocardial biopsy may include unexplained cardiomyopathy, myocarditis, ventricular arrhythmias, cardiac hemachromatosis, amyloidosis, anthracycline cardiotoxicity, cardiac sarcoidosis, giant cell myocarditis, hypereosinophilic syndrome, or endocardial fibroelastosis. (Kilo, Laufer et al. 2006) EMB is also often used to evaluate the efficacy of immunosuppressive therapy after cardiac transplantation. (Kilo, Laufer et al. 2006) Finally, EMB may provide insight in the setting of unexplained, new-onset heart failure associated with a normal-sized or dilated left ventricle in addition to hemodynamic compromise. (Cooper, Baughman et al. 2007) Further, EMB may also be employed in the event of a suspected cardiac tumor. In fact, the performance of a EMB is recommended in the event (1) the diagnosis of a cardiac tumor cannot be established by noninvasive modalities (such as cardiac MRI) or less invasive biopsy; (2) tissue diagnosis can be expected to influence the course of therapy; (3) the chances of successful biopsy are believed to be reasonably high; and (4) the procedure is performed by an experienced operator. (Cooper, Baughman et al. 2007) The first nonsurgical techniques for cardiac biopsies were reported in 1958. In the 1960s, the safety of cardiac biopsy improved with sampling of the right interventricular septum, and designation of the heart borders by right heart catheterization before biopsy. While biopsy tissue samples had historically been obtained using cutting techniques, Sakakibara and Konno (Sakakibara and Konno 1962) introduced the use of a flexible bioptome that a biopsy sample to be obtained through a pinching technique. Some time thereafter, Caves et al (Caves, Stinson et al. 1973) modified the Konno biopsy forceps (Stanford Caves-Shulz bioptome) to allow percutaneous biopsies through the right internal jugular vein with only local anesthesia and rapid tissue removal. The reusable Stanford-Caves bioptome became the standard device for EMB for approximately 2 decades. (Cooper, Baughman et al. 2007)

The femoral artery may be used as a percutaneous access site for left ventricular biopsy. The right internal jugular vein is the most common percutaneous access site for right ventricular EMB in the United States. In Germany and Italy, the femoral vein is commonly used for percutaneous access. (Cooper, Baughman et al. 2007) EMB is usually performed safely under fluoroscopic guidance. Some operators use fluoroscopy and echocardiography in combination to enhance entry into the right ventricle.

EMB is a very safe procedure and procedural mortality ranges from 0-0.4%. A number of potential complications are inherent, however, in the operation including: Perforation/pericardial tamponade (Incidence: 0-0.5%), Tricuspid valve damage (14%), Bleeding at puncture site (venous/arterial due to accidental arterial puncture) (0.14-0.4%); Pneumothorax (0.1%), Arrhythmias (supraventricular/ventricular tachycardia/complete heart block) (0.25-1.1%). Overall, complications are infrequent for skilled surgeons, and especially life-threatening complications are rarely encountered. (Kilo, Laufer et al. 2006)

The risks of EMB may be divided into those that are acute and those that are delayed. Immediate risks of biopsy include perforation with pericardial tamponade, ventricular or supraventricular arrhythmias, heart block, pneumothorax, puncture of central arteries, pulmonary embolization, nerve paresis, venous hematoma, damage to the tricuspid valve, and creation of arterial venous fistula within the heart. The risks of EMB vary with the experience of the operator, clinical status of the patient, presence or absence of left bundle-branch block, access site, and possibly bioptome. Delayed complications include access site bleeding, damage to the tricuspid valve, pericardial tamponade, and deep venous thrombosis. (Cooper, Baughman et al. 2007)

Clearly, there is a need for myocardial biopsy including the epicardial tissue that is easy to use, relatively inexpensive, and safe.

BRIEF SUMMARY

Disclosed herein are devices, systems, and methods for engaging a tissue, including, but not limited to, accessing the internal and external tissues of the heart. At least some of the disclosed embodiments provide access to the external surface of the heart through the pericardial space for localized delivery of leads to the heart tissue. In addition, various disclosed embodiments provide devices, systems, and methods for engaging a tissue.

In at least one embodiment of a system for use with a vacuum source for engaging a tissue according to the present disclosure, the system comprises an engagement catheter comprising a proximal end, a distal end, first and second lumens extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, a delivery catheter comprising a proximal end, a distal end, and a hollow tube extending between the proximal end and the distal end, the delivery catheter configured such that the hollow tube is capable of insertion into the second lumen of the engagement catheter, a needle located at the distal end of the delivery catheter, and a vacuum port located at the proximal end of the engagement catheter, the vacuum port being operatively connected to the first lumen of the engagement catheter and capable of operative connection to the vacuum source, wherein the first lumen of the engagement catheter includes a suction port located at or near the distal end of the engagement catheter, the suction port configured to allow the proximal end of the skirt to removably engage a surface of a tissue such that the skirt is capable of forming a reversible seal with the surface of the tissue when a vacuum source is operatively attached to the vacuum port. In another embodiment, the system is capable of enlarging a pericardial space between the targeted tissue and a pericardial sac that surrounds a heart by retracting the targeted tissue away from the pericardial sac. In yet another embodiment, the tissue engaged by the system is a heart. In an additional embodiment, the system is capable of enlarging a pericardial space between the heart and a pericardial sac when the skirt is attached to an interior wall of the heart.

In at least one embodiment of a system for use with a vacuum source for engaging a tissue according to the present disclosure, the skirt comprises a deformable configuration. In another embodiment, the deformable configuration of the skirt is capable of expanding to an expanded configuration. In yet another embodiment, the expanded configuration is a frusto-conical configuration. In an additional embodiment, the expanded configuration is a an irregular frusto-conical configuration.

In at least one embodiment of a system for use with a vacuum source for engaging a tissue according to the present disclosure, the system further comprises a sleeve comprising a proximal end, a distal end, and a lumen extending between the proximal end and the distal end, wherein the sleeve is positioned circumferentially around the engagement catheter, wherein the sleeve slidingly engages the engagement catheter. In another embodiment, the sleeve may be positioned at the distal end of the engagement catheter, wherein the sleeve at least partially surrounds the skirt. In yet another embodiment, the deformable configuration of the skirt is collapsed when at least partially surrounded by the sleeve.

In at least one embodiment of a system for use with a vacuum source for engaging a tissue according to the present disclosure, the sleeve is positioned along the engagement catheter so not to surround the skirt, wherein the skirt is capable of expanding to an expanded configuration. In another embodiment, the expanded configuration is a frusto-conical configuration. In yet another embodiment, the expanded configuration is a an irregular frusto-conical configuration.

In at least one embodiment of a system for use with a vacuum source for engaging a tissue according to the present disclosure, the targeted tissue comprises a portion of an atrial wall. In another embodiment, the targeted tissue comprises a portion of an atrial appendage. In yet another embodiment, the needle is positioned to be capable of piercing the targeted tissue when the hollow tube is inserted into the second lumen and the suction port is attached to the targeted tissue, such that, when the targeted tissue is pierced, access to the pericardial space is achieved. In an additional embodiment, the system further comprises a guide wire for insertion into the pericardial space. In yet an additional embodiment, the needle comprises a hollow needle in communication with the hollow tube, and the guide wire is capable of insertion through the hollow tube and the hollow needle into the pericardial space.

In at least one embodiment of a system for use with a vacuum source for engaging a tissue according to the present disclosure, the engagement catheter further comprises an injection channel in fluid communication with the second lumen of the engagement catheter, the injection channel being configured to administer a fluid to the targeted tissue. In another embodiment, the fluid comprises an adhesive. In yet another embodiment, the injection channel is ring-shaped.

In at least one embodiment of a system for use with a vacuum source for engaging a tissue according to the present disclosure, the engagement catheter further comprises an injection channel formed along the length of the engagement catheter, the injection channel having at its distal end at least one opening for administering a fluid to the targeted tissue, the injection channel being capable of operable attachment to an external fluid source at the proximal end of the injection channel, such that fluid from the external fluid source can flow through the injection channel to the targeted tissue when the external fluid source is operatively attached to the injection channel. In another embodiment, the needle comprises a needle wire for piercing the targeted tissue. In yet another embodiment, the needle comprises a pressure tip needle.

In at least one embodiment of a system for use with a vacuum source for engaging a tissue according to the present disclosure, the engagement catheter comprises a curvature along a length of the engagement catheter. In another embodiment, the curvature of the engagement catheter forms an angle that is approximately forty-five degrees. In yet another embodiment, the curvature of the engagement catheter forms an angle that is approximately ninety degrees, so that a portion of the engagement catheter is approximately perpendicular to another portion of the engagement catheter. In an additional embodiment, the curvature of the engagement catheter forms an angle so that a portion of the engagement catheter is approximately parallel to another portion of the engagement catheter.

In at least one embodiment of an engagement catheter for use with a vacuum source for engaging a tissue according to the present disclosure, the engagement catheter comprises an elongated tube comprising a proximal end, a distal end, an outer wall positioned circumferentially along the length of the tube, and an inner wall positioned circumferentially along the length of the tube, wherein the outer wall and the inner wall form at least one suction channel along the length of the tube between the outer wall and the inner wall, a skirt operatively connected to the distal end of the tube, the skirt comprising a proximal end having a circumference substantially similar to an outer circumference of the tube, the skirt further comprising a distal end having a circumference larger than the circumference of the tube, a vacuum port in communication with the proximal end of the tube, the vacuum port being operatively connected to the at least one suction channel and capable of operative connection to the vacuum source, and a suction port in communication with the at least one suction channel at the distal end of the tube, the suction port configured to allow the proximal end of the skirt to removably engage a surface of a tissue such that the skirt is capable of forming a reversible seal with the surface of the tissue when a vacuum source is operatively attached to the vacuum port. In another embodiment, the skirt comprises a deformable configuration. In yet another embodiment, the deformable configuration of the skirt is capable of expanding to an expanded configuration. In an additional embodiment, the expanded configuration is a frusto-conical configuration. In yet an additional embodiment, the expanded configuration is a an irregular frusto-conical configuration.

In at least one embodiment of an engagement catheter for use with a vacuum source for engaging a tissue according to the present disclosure, the skirt has a collapsed configuration when the skirt is at least partially surrounded by a sleeve, and wherein the skirt has an expanded configuration when the skirt is not surrounded by the sleeve. In another embodiment, wherein the tissue engaged by the skirt of the engagement catheter is a heart. In yet another embodiment, wherein the skirt is capable of enlarging a pericardial space between the heart and a pericardial sac when the skirt is attached to an interior wall of the heart.

In at least one embodiment of an engagement catheter for use with a vacuum source for engaging a tissue according to the present disclosure, the engagement catheter further comprises at least one internal lumen support positioned within the at least one suction channel and attached to the outer wall and the inner wall, the at least one internal lumen support extending from the distal end of the tube along at least a substantial portion of the length of the tube. In another embodiment, wherein the at least one internal lumen support comprises two internal lumen supports, and the at least one suction channel comprises two suction channels. In yet another embodiment, further comprising an injection channel formed along the length of the tube, the injection channel having at its distal end at least one opening for administering a fluid to the targeted tissue, the injection channel being capable of operable attachment to an external fluid source at the proximal end of the injection channel, such that fluid from the external fluid source can flow through the injection channel to the targeted tissue when the external fluid source is operatively attached to the injection channel.

In at least one embodiment of a method for engaging a tissue according to the present disclosure, the method comprises the steps of providing a system, comprising an engagement catheter comprising a proximal end, a distal end, first and second lumens extending between the proximal end and the distal end, and a skirt operatively connected to the distal end, the skirt comprising a proximal end having a circumference substantially similar to an outer circumference of the engagement catheter, the skirt further comprising a distal end having a circumference larger than the outer circumference of the engagement catheter, a delivery catheter comprising a proximal end, a distal end, and a hollow tube extending between the proximal end and the distal end, the delivery catheter configured such that the hollow tube is capable of insertion into the second lumen of the engagement catheter, a needle located at the distal end of the delivery catheter, and a vacuum port located at the proximal end of the engagement catheter, the vacuum port being operatively connected to the first lumen of the engagement catheter and capable of operative connection to the vacuum source, wherein the first lumen of the engagement catheter includes a suction port located at or near the distal end of the engagement catheter, the suction port configured to allow the proximal end of the skirt to removably engage a surface of a targeted tissue such that the skirt is capable of forming a reversible seal with the surface of the targeted tissue when a vacuum source is operatively attached to the vacuum port, and inserting the engagement catheter into a body such that the distal end of the engagement catheter is positioned at or near the targeted tissue.

In another embodiment, the system is capable of enlarging a pericardial space between the targeted tissue and a pericardial sac that surrounds a heart by retracting the targeted tissue away from the pericardial sac. In yet another embodiment, the step of inserting the engagement catheter into a body comprises the insertion of the engagement catheter such that the distal end of the engagement catheter is positioned inside the heart and the skirt is in contact with the targeted tissue on the interior of a wall of the heart. In an additional embodiment, the method further comprises the step of operatively connecting a vacuum source to the vacuum port such that the skirt is reversibly attached to the targeted tissue on the interior of a wall of the heart.

In at least one embodiment of a method for engaging a tissue according to the present disclosure, the method further comprises the step of inserting the delivery catheter into the second lumen of the engagement catheter In another embodiment, the method further comprises the step of piercing the targeted tissue on the interior of a wall of the heart with the needle. In yet another embodiment, the method further comprises the step of administering a substance into the pericardial space. In an additional embodiment, the method further comprises the steps of withdrawing the needle from the targeted tissue and administering a substance to the targeted tissue after withdrawal of the needle. In yet an additional embodiment, the substance comprises an adhesive for sealing a puncture wound in the targeted tissue.

In at least one embodiment of a method for engaging a tissue according to the present disclosure, the targeted tissue comprises a portion of an atrial wall. In another embodiment, the targeted tissue comprises a portion of an atrial appendage. In yet another embodiment, the method further comprises the step of accessing the pericardial space by inserting a guide wire through the wall of the heart into the pericardial space.

In at least one embodiment of catheter for use with a vacuum source for removing fluid from a tissue according to the present disclosure, the catheter comprises an elongated tube comprising a proximal end, a distal end, an outer wall positioned circumferentially along the length of the tube, and an inner wall positioned circumferentially along the length of the tube defining a lumen within the tube, wherein the inner wall forms at least one suction channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the at least one suction channel, a vacuum port in communication with the proximal end of the tube, the vacuum port being operatively connected to the at least one suction channel and capable of operative connection to the vacuum source, the suction channel configured to allow fluid present within a space in a body to enter the one or more apertures in communication with the at least one suction channel and be removed via the at least one suction channel when the vacuum source is operatively attached to the vacuum port. In another embodiment, at least one concave groove is defined on the outer wall extending along at least part of the length of the tube. In yet another embodiment, the one or more apertures defined along the tube are defined along the at least one concave groove. In an additional embodiment, the at least one concave groove defines one or more ridges extending along at least part of the length of the tube, wherein said ridges are configured and arranged to allow for a clearance between a tissue and the one or more apertures.

In at least one embodiment of catheter for use with a vacuum source for removing fluid from a tissue according to the present disclosure, the at least one concave groove comprises at least three concave grooves. In another embodiment, the one or more apertures comprise at least three apertures. In yet another embodiment, the catheter comprises a curvature along a length of the catheter. In an additional embodiment, the catheter further comprises at least one delivery channel defined within the tube and positioned along the length of the tube, wherein at least one of the one or more apertures is/are in communication with the at least one delivery channel.

In at least one embodiment of catheter for use with a vacuum source for removing fluid from a tissue according to the present disclosure, the at least one delivery catheter is operable to deliver a substance from a delivery source present at a proximal end of the delivery channel through at least one of the one or more apertures in communication with the at least one delivery channel for delivery to a target site. In another embodiment, the substance comprises a substance of at least one from the group consisting of a gas, a liquid, and a particulate. In yet another embodiment, the substance comprises a substance of at least one from the group consisting of an antibiotic, a cytostatic agent, a sclerosing agent, a cytotoxic agent, an immunomodulator, and a crystalloid glucocorticoid. In an additional embodiment, the vacuum port is further capable of operative connection to a delivery source, and wherein the suction channel is configured to deliver a substance when a delivery source containing the substance is operatively attached to the vacuum port, wherein the substance is delivered from the delivery source through the suction channel and through at least one of the one or more apertures in communication with the at least one suction channel to a target site. In yet an additional embodiment, the vacuum source comprises a syringe.

In at least one embodiment of a system for use with a vacuum source for removing fluid from a tissue according to the present disclosure, the system comprises an engagement catheter comprising a proximal end, a distal end, and a lumen extending between the proximal end and the distal end, a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at least one suction channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the at least one suction channel, a vacuum port in communication with the proximal end of the tube, the vacuum port being operatively connected to the at least one suction channel and capable of operative connection to the vacuum source, the suction channel configured to allow fluid present within a space in a body to enter the one or more apertures in communication with the at least one suction channel and be removed via the at least one suction channel when the vacuum source is operatively attached to the vacuum port, wherein the suction catheter is configured so that it is capable of insertion into the lumen of the engagement catheter. In another embodiment, the suction catheter is operable to enter a space of a tissue via insertion through the lumen of the engagement catheter. In yet another embodiment, the suction catheter is operable to enter a right atrial appendage of a heart via insertion through the lumen of the engagement catheter. In an additional embodiment, the suction catheter is further operable to enter a visceral pericardium of a heart to access a pericardial sac.

In at least one embodiment of a system for use with a vacuum source for removing fluid from a tissue according to the present disclosure, at least one concave groove is defined on the outer wall of the suction catheter extending along at least part of the length of the tube. In another embodiment, the one or more apertures defined along the tube are defined along the at least one concave groove. In yet another embodiment, the at least one concave groove defines one or more ridges extending along at least part of the length of the tube, wherein said ridges are configured and arranged to allow for a clearance between a tissue and the one or more apertures. In an additional embodiment, the catheter suction comprises a curvature along a length of the suction catheter.

In at least one embodiment of a system for use with a vacuum source for removing fluid from a tissue according to the present disclosure, wherein the suction catheter further comprises at least one delivery channel defined within the tube and positioned along the length of the tube, wherein at least one of the one or more apertures is/are in communication with the at least one delivery channel. In another embodiment, the at least one delivery catheter is operable to deliver a substance from a delivery source present at a proximal end of the delivery channel through at least one of the one or more apertures in communication with the at least one delivery channel for delivery to a target site. In yet another embodiment, the substance comprises a substance of at least one from the group consisting of a gas, a liquid, and a particulate.

In at least one embodiment of a system for use with a vacuum source for removing fluid from a tissue according to the present disclosure, the substance comprises a substance of at least one from the group consisting of an antibiotic, a cytostatic agent, a sclerosing agent, a cytotoxic agent, an immunomodulator, and a crystalloid glucocorticoid. In another embodiment, the vacuum port is further capable of operative connection to a delivery source, and wherein the suction channel is configured to deliver a substance when a delivery source containing the substance is operatively attached to the vacuum port, wherein the substance is delivered from the delivery source through the suction channel and through at least one of the one or more apertures in communication with the at least one suction channel to a target site. In yet another embodiment, the vacuum source comprises a syringe.

In at least one embodiment of a method for using a suction catheter to remove fluid from a tissue according to the present disclosure, the method comprising the steps of providing a system, comprising an engagement catheter comprising a proximal end, a distal end, and a first lumen extending between the proximal end and the distal end, and a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at first channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the first channel, a first port in communication with the proximal end of the tube, the first port being operatively connected to the first channel and capable of operative connection to the first vacuum source, the channel configured to allow fluid present within a space in a body to enter the one or more apertures in communication with the first channel and be removed via the first channel when the first vacuum source is operatively attached to the first port, wherein the suction catheter is configured so that it is capable of insertion into the first lumen of the engagement catheter, inserting the engagement catheter into a body such that the distal end of the engagement catheter is positioned at or near a tissue wall surrounding a space within a tissue, and inserting the suction catheter into the first lumen of the engagement catheter wherein the suction catheter exits the distal end of the engagement catheter through the tissue wall so that the distal end of the suction catheter is present within the space surrounded by the tissue wall and in contact with a fluid present within said space. In another embodiment, the method further comprises the step of operatively connecting a first vacuum source to the first port such that at least a portion of the fluid present within said space enters the one or more apertures in communication with the first channel and is removed via the first channel. In yet another embodiment, at least one concave groove is defined on the outer wall extending along at least part of the length of the tube.

In at least one embodiment of a method for using a suction catheter to remove fluid from a tissue according to the present disclosure, the one or more apertures defined along the tube are defined along the at least one concave groove. In another embodiment, the at least one concave groove defines one or more ridges extending along at least part of the length of the tube, wherein said ridges are configured and arranged to allow for a clearance between a tissue and the one or more apertures. In yet another embodiment, the tissue wall is a right atrial appendage of a heart. In an additional embodiment, the tissue wall is a visceral pericardium of a heart.

In at least one embodiment of a method for using a suction catheter to remove fluid from a tissue according to the present disclosure, the first port is further capable of operative connection to a delivery source, and wherein the first channel is configured to deliver a substance when a delivery source containing the substance is operatively attached to the first port. In another embodiment, the method further comprises the step of operatively connecting a delivery source containing a substance to the first port such that at least a portion of the substance present within the delivery source is delivered from the delivery source through the first channel and through at least one of the one or more apertures in communication with the first channel to a target site. In yet another embodiment, the substance comprises a substance of at least one from the group consisting of an antibiotic, a cytostatic agent, a sclerosing agent, a cytotoxic agent, an immunomodulator, and a crystalloid glucocorticoid. In an additional embodiment, the method further comprises the step of operatively connecting a first vacuum source to the first port such that at least a portion of the substance present within said space enters the one or more apertures in communication with the first channel and is removed via the first channel.

In at least one embodiment of a method for using a suction catheter to remove fluid from a tissue according to the present disclosure, the suction catheter further comprises a second lumen defining a second channel positioned within and along the length of the tube, wherein one or more delivery apertures are defined along the tube, and wherein the one or more delivery apertures extend from the outer wall of the tube to the second lumen of the tube, the one or more delivery apertures present at or near the distal end of the tube. In another embodiment, a second port is in communication at or near the proximal end of the tube, the second port being operably connected to the second channel, wherein the second port is further capable of operative connection to a delivery source, and wherein the second channel is configured to deliver a substance when a delivery source containing the substance is operatively attached to the second port. In yet another embodiment, the method further comprises the step of operatively connecting a delivery source containing a substance to the second port such that at least a portion of the substance present within the delivery source is delivered from the delivery source through the second channel and through at least one of the one or more delivery apertures in communication with the second channel to a target site.

In at least one embodiment of a method for using a suction catheter to remove fluid from a tissue according to the present disclosure, the method comprises the steps of providing a system, comprising, an engagement catheter comprising a proximal end, a distal end, and a first lumen extending between the proximal end and the distal end, a piercing catheter comprising a proximal end, a distal end, and a hollow cylinder extending between the proximal end and the distal end, the piercing catheter having a needle at the distal end of the delivery catheter, the piercing catheter configured such that the hollow cylinder is capable of insertion into the first lumen of the engagement catheter, and a suction catheter comprising an elongated tube comprising a proximal end, a distal end, an outer wall positioned circumferentially along the length of the tube, and an inner wall positioned circumferentially along the length of the tube defining a lumen within the tube, wherein the inner wall forms at first channel along the length of the tube, one or more apertures defined along the tube, wherein the one or more apertures extend from the outer wall of the tube to the inner wall of the tube, the one or more apertures present at or near the distal end of the tube, wherein at least one of the one or more apertures is/are in communication with the first channel, a first port in communication with the proximal end of the tube, the first port being operatively connected to the first channel and capable of operative connection to the first vacuum source, the channel configured to allow fluid present within a space in a body to enter the one or more apertures in communication with the first channel and be removed via the first channel when the first vacuum source is operatively attached to the first port, wherein the suction catheter is configured so that it is capable of insertion into the first lumen of the engagement catheter, inserting the engagement catheter into a body such that the distal end of the engagement catheter is positioned at or near a tissue wall surrounding a space within a tissue, inserting the piercing catheter into the first lumen of the engagement catheter wherein the piercing catheter exists the distal end of the engagement catheter and pierces the tissue wall with the needle of the piercing catheter, removing the piercing catheter from the engagement catheter, inserting the suction catheter into the first lumen of the engagement catheter wherein the suction catheter exits the distal end of the engagement catheter through the tissue wall so that the distal end of the suction catheter is present within the space surrounded by the tissue wall and in contact with a fluid present within said space, and operatively connecting a first vacuum source to the first port such that at least a portion of the fluid present within said space enters the one or more apertures in communication with the first channel and is removed via the first channel.

In at least one embodiment of a method for engaging a tissue according to the present disclosure, the method further comprises the step of removing the delivery catheter from the engagement catheter. In another embodiment, the method further comprises the step of inserting a suction catheter into the second lumen of the engagement catheter, wherein the suction catheter exits the distal end of the engagement catheter through the pierced tissue so that a distal end of the suction catheter is present within a space at least partially surrounded by the pierced tissue and in contact with a fluid present within said space. In yet another embodiment, the suction catheter comprises an elongated suction tube comprising a proximal end, a distal end, an outer wall positioned circumferentially along the length of the suction tube, and an inner wall positioned circumferentially along the length of the suction tube defining a lumen within the suction tube, wherein the inner wall forms of first channel along the length of the suction tube, one or more apertures defined along the tube, wherein the one or more apertures extend from the outer wall of the tube to the inner wall of the suction tube, the one or more apertures present at or near the distal end of the suction tube, wherein at least one of the one or more apertures is/are in communication with the first channel, a suction catheter port in communication with the proximal end of the suction tube, the suction catheter port being operatively connected to the first channel and capable of operative connection to a suction catheter vacuum source, the first channel configured to allow fluid present within a space in a body to enter the one or more apertures in communication with the first channel and be removed via the first channel when the suction catheter vacuum source is operatively attached to the suction catheter port, wherein the suction catheter is configured so that it is capable of insertion into the second lumen of the engagement catheter. In an additional embodiment, the method further comprises the step of operatively connecting a suction catheter vacuum source to the suction catheter port such that at least a portion of the fluid present within said space enters the one or more apertures in communication with the first channel and is removed via the first channel.

Also disclosed herein are devices, systems and methods for taking a biopsy tissue sample from a targeted tissue in a minimally invasive manner. At least some of the disclosed embodiments used the methods disclosed herein for accessing the external surface of the heart through the pericardial space to obtain access to a targeted tissue. In at least one embodiment of a system for obtaining a tissue sample from a targeted tissue the system comprises a first catheter, a second catheter slidably disposed within the first catheter, a torque mechanism coupled with both the first and second catheters, and at least one suction port in communication with either, or both, of the catheters and capable of operative connection to a vacuum source. The first catheter comprises a proximal end, a distal end, and a hollow interior; the distal end of the first catheter comprising a cutting portion capable of cutting a targeted tissue. In some embodiments, the cutting portion comprises a metallic cylinder having a sharp cutting edge. The second catheter is slidably disposed within the interior of the first catheter and comprises a proximal end, a hollow interior, a distal end, and an opening disposed proximal to the distal end of the second catheter, wherein the distal end is capable of puncturing the targeted tissue and the opening is in communication with the interior of the second catheter. In certain embodiments, the second catheter may comprise a hollow needle. In at least one alternative embodiment, the distal end of the second catheter comprises a tapered configuration. Both the first and second catheters may be comprised of a semi-rigid material that are capable of intravascular insertion.

In some embodiments, the torque mechanism of the system comprises at least one dial coupled with at least one shaft, the at least one dial being capable of rotational movement and the at least one shaft being capable of converting the rotational movement of the at least one dial into linear movement. For example, the at least one shaft may comprise a leadscrew. The at least one shaft is coupled with the proximal ends of the first and second catheters such that the at least one shaft is capable of advancing and retracting the first and second catheters. In at least one embodiment, the at least one shaft may be coupled with the first and second catheters in such a manner that the at least one shaft is capable of advancing and retracting the first and second catheters independently of each other. Further, in certain embodiments, the dial may be capable of segmented rotational movement and the at least one shaft is capable of converting the segmented rotational movement of the at least one dial into a defined amount of linear movement of the relevant catheter. For example, and without limitation, one segmented rotation of the at least one dial may correspond to 1 mm of linear movement of the relevant catheter.

Further embodiments of the system may comprise a limiter device coupled with the at least one shaft of the torque mechanism. The limiter device is capable of preventing the catheters from advancing farther than a specified distance. Certain embodiments comprise more than one limiter device and, in at least one embodiment, a first limiter device may be coupled with a first shaft that is coupled with the first catheter and a second limiter device may be coupled with a second shaft that is coupled with the second catheter. In such embodiments, the first limiter device is capable of preventing the first catheter from advancing farther than a first distance, and the second limiter device is capable of preventing the second catheter from advancing farther than a second distance. In at least one embodiment of a system for obtaining a tissue sample from a targeted tissue as disclosed herein, the system may be used to obtain a tissue sample from a heart through intravascular insertion.

In yet another embodiment, the biopsy system may comprise a single catheter having a proximal end, an open distal end, and a hollow interior. In this at least one embodiment, the distal end of the catheter comprises a tapered configuration, a cutting edge capable of slicing a targeted tissue and an opening. Further, in addition to being capable of advancing and retracting the catheter through operation of the torque mechanism as previously described with respect to alternative embodiments, in this at least one embodiment, the torque mechanism is further capable of converting rotational movement of the dial into rotational movement of the catheter. In this manner, when the catheter is rotated in a first direction, this causes the cutting edge of the catheter to slice a targeted tissue. Further, the cutting edge and the opening of the distal end of the catheter are configured to allow the sliced tissue to be drawn through the opening and into the interior of the catheter. For example, and without limitation, in at least one embodiment, the distal end of the catheter further comprises a first edge and a second edge configured in a tapered configuration such that the first edge overlaps the second edge and the opening is formed therebetween. In these embodiments, the distal end of the catheter may comprise a metallic material.

Embodiments of the system for accessing a targeted tissue and obtaining a tissue sample therefrom are also described herein. For example, and without limitation, certain embodiments of the system for accessing a targeted tissue and obtaining a tissue sample therefrom include embodiments of the biopsy system used in conjunction with a delivery catheter, a steering wire system, and a navigational tool. Such embodiments may also be used in conjunction with a guide wire. The embodiments of the system disclosed herein allows a clinician to access the epicardial surface of a heart and obtain a tissue sample therefrom in a minimally invasive manner. Further, embodiments of the system disclosed herein may be used in conjunction with other tissues of a body and need not be limited to application in the heart.

In such embodiments, the delivery catheter may comprise a proximal end, a distal end, and a first, second and third lumens extending between the proximal end and the distal end. In certain embodiments, the delivery catheter is capable of intravascular insertion into a body. The second and third lumens of the delivery catheter may each comprise a bend at a location proximal to the distal end of the delivery catheter and each of the bends may comprise an angle of between about ninety degrees and about thirty degrees. In some embodiments, the first lumen has an outlet disposed proximal to the distal end of the delivery catheter, the second lumen comprises an outlet disposed at or near the distal end of the delivery catheter, and the third lumen comprises an outlet positioned at or near the distal end of the delivery catheter. The steering wire system may be disposed within the first lumen of the delivery catheter, and the steering wire system is capable of facilitating the navigation of the delivery catheter through vasculature of a body. Similarly, in certain embodiments, a navigational tool may additionally be disposed within the second lumen of the delivery catheter. In certain embodiments, the navigational tool comprises a laser Doppler tip, an endo-camera, and a micro-camera, and may be capable of being advanced through the outlet of the second lumen of the delivery catheter. Such systems may further employ embodiments of the biopsy system as previously described herein. In certain embodiments, the biopsy system is slidably disposed within the third lumen of the delivery catheter.

In at least one embodiment, each of the navigational tool, the steering wire system and the biopsy system may be independently controlled by a user. In this manner, the embodiments of the system may be used to access certain targeted tissues and obtain a tissue sample therefrom.

In at least one embodiment of a method for engaging a tissue and retrieving a tissue sample therefrom, the method comprises the steps of providing a system comprising 1) a delivery catheter comprising a proximal end, a distal end, and first, second, and third lumens extending between the proximal end and the distal end, the second and third lumens each comprising a bend at a location proximal to the distal end of the delivery catheter, the first lumen having an outlet disposed proximal to the distal end of the delivery catheter, the second lumen comprising an outlet disposed at or near the distal end of the delivery catheter, and the third lumen comprising an outlet positioned at or near the distal end of the delivery catheter, 2) a steering wire system disposed within the first lumen of the delivery catheter, the steering wire system being capable of facilitating the navigation of the delivery catheter through vasculature of a body, 3) a navigational tool disposed within the second lumen of the delivery catheter, and 4) a biopsy system slidably disposed within the third lumen of the delivery catheter, the biopsy system comprising a) a first catheter having a proximal end, an open distal end, and a hollow interior, the distal end of the catheter comprising a cutting portion capable of cutting a targeted tissue, b) a second catheter slidably received within the interior of the first catheter, the second catheter having a proximal end, a hollow interior, a distal end capable of puncturing the targeted tissue, and an opening disposed proximal to the distal end of the second catheter and in communication with the interior of the second catheter, c) a torque mechanism comprising at least one dial coupled with at least one shaft, the at least one dial being capable of rotational movement and the at least one shaft being capable of converting the rotational movement of the at least one dial into linear movement, d) at least one suction port in communication with either the interior of the first catheter, the interior of the second catheter, or both, the at least one suction port capable of operative connection to a vacuum source, wherein the at least one shaft is coupled with the proximal end of the first catheter such that the at least one shaft is capable of advancing and retracting the first catheter and the at least one shaft is coupled with the proximal end of the second catheter such that the at least one shaft is capable of advancing and retracting the second catheter, and wherein the delivery catheter is capable of intravascular insertion into a body and the bends of the second and third lumens comprise an angle of between about ninety degrees and about thirty degrees; inserting the delivery catheter into a body such that the distal end of the delivery catheter is positioned at or near a targeted tissue; and advancing the first and second catheters through the outlet of the third lumen by operation of the torque mechanism such that the distal ends of the first and second catheters are positioned at or near the targeted tissue. In yet another embodiment, the method further comprises the step of accessing the pericardial space of a heart through an intravascular approach. Further, the method may also comprise the step of using the navigational tool to locate the targeted tissue on the epicardial surface of the heart. In certain embodiments, the step of inserting the delivery catheter into a body such that the distal end of the delivery catheter is positioned at or near a targeted tissue comprises the insertion of the delivery catheter such that the distal end of the delivery catheter is positioned in the pericardial space.

In still other embodiments, the method may further comprise the step of operatively connecting a vacuum source to the at least one suction port such that the distal end of the first catheter is reversibly coupled with the epicardial surface of a heart. Still further, the method may comprise the step of piercing the targeted tissue on the epicardial surface of the heart with the distal end of the second catheter. In certain embodiments of the method, the step of piercing the targeted tissue on the epicardial surface of the heart with the distal end of the second catheter further comprises operating the torque mechanism of the biopsy system to advance the distal end of the second catheter a first distance into the targeted tissue on the epicardial surface of the heart. In at least one additional embodiment, the method may further comprise the step of advancing the first catheter through operation of the torque mechanism such that the cutting portion of the first catheter cuts a portion of the targeted tissue on the epicardial surface of the heart. Still further, the method may comprise the step of operating the vacuum source to increase the suction through the interior of the second catheter such that the cut portion of the targeted tissue is pulled into the interior of the second catheter through the opening of the second catheter and detached from the epicardial surface of the heart. Still further, embodiments of the method may further comprise the step of withdrawing the first catheter and the second catheter containing the removed portion of the targeted tissue. Embodiments of this step may be performed in conjunction with decreasing the suction through the interior of the first catheter and/or increasing the suction through the interior of the second catheter.

In the certain embodiments of the biopsy system comprising a single catheter, the method may comprise the steps of inserting the delivery catheter into a body such that the distal end of the delivery catheter is positioned at or near a targeted tissue and advancing the catheter of the biopsy system through the outlet of the third lumen by operation of the torque mechanism such that the distal end of the catheter is positioned at or near the targeted tissue. Certain embodiments of the method may further comprise the step of operatively connecting a vacuum source to the suction port such that the distal end of the catheter is reversibly coupled with the epicardial surface of the heart. In addition, at least one embodiment of the method may further comprise the step of piercing the targeted tissue on the epicardial surface of the heart with the distal end of the catheter. In yet another embodiment, the method may further comprise the step of rotating the distal end of the catheter in a first direction (through operation of the torque mechanism) such that the cutting edge slices the targeted tissue, thereby removing a portion of the tissue from the epicardial surface of the heart and drawing the removed portion of the tissue into the interior of the catheter through the opening. In yet another embodiment, the method may further comprise the step of operating the vacuum source to increase the suction through the interior of the catheter such that the removed portion of tissue is maintained within the interior of the catheter. In addition, the method may further comprise the step of withdrawing the catheter containing the removed portion of tissue from the epicardial surface of the heart.

BRIEF DESCRIPTION OF THE DRAWINGS

FIG. 3A shows removal of an embodiment of a catheter as disclosed herein;

FIG. 3B shows the resealing of a puncture according to an embodiment as disclosed herein;

FIG. 5A shows an embodiment of an engagement catheter as disclosed herein;

FIG. 5B shows a cross-sectional view of the proximal end of the engagement catheter shown in FIG. 5A;

FIG. 5C shows a cross-sectional view of the distal end of the engagement catheter shown in FIG. 5A;

FIG. 6A shows an embodiment of a delivery catheter as disclosed herein;

FIG. 6B shows a close-up view of the needle shown in FIG. 6A;

FIG. 6C shows a cross-sectional view of the needle shown in FIGS. 6A and 6B;

FIG. 9A shows another embodiment of a steering wire system as disclosed herein, the embodiment being deflected in one location;

FIG. 9B shows the steering wire system shown in FIG. 9A, wherein the steering wire system is deflected at two locations;

FIG. 9C shows the steering wire system shown in FIGS. 9A and 9B in its original position;

FIG. 15C shows the embodiment of FIGS. 15A-15C deployed on the cardiac tissue;

FIG. 17A shows an embodiment of a portion of an apparatus for engaging a tissue that has engaged a tissue, as disclosed herein;

FIG. 17B shows an embodiment of a portion of an apparatus for engaging a tissue having an expanded skirt that has engaged a tissue, as disclosed herein;

FIG. 18A shows an embodiment of a portion of an apparatus for engaging a tissue having a collapsed skirt present within a sleeve, as disclosed herein;

FIG. 18B shows an embodiment of a portion of an apparatus for engaging a tissue having an expanded skirt, as disclosed herein;

FIG. 21A shows an embodiment of a portion of an apparatus for removing fluid from a tissue, as disclosed herein;

FIG. 21B shows an embodiment of a portion of an apparatus comprising grooves for removing fluid from a tissue, as disclosed herein;

FIGS. 26A-26D show an embodiment of a biopsy system collecting a tissue sample from a targeted tissue;

DETAILED DESCRIPTION

It will be appreciated by those of skill in the art that the following detailed description of the disclosed embodiments is merely exemplary in nature and is not intended to limit the scope of the appended claims.

The disclosed embodiments include devices, systems, and methods useful for accessing various tissues of the heart from inside the heart. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space. At least some embodiments of such devices, systems and methods are further described in U.S. patent application Ser. No. 12/596,964 to Kassab et al. and U.S. patent application Ser. No. 12/596,968 to Kassab et al., each of which are incorporated by reference in their entirety herein.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, as explained in more detail below, epicardial pacing leads may be delivered via the pericardial space, and an ablation catheter may be used on the epicardial tissue from the pericardial space.

Figure 1A:
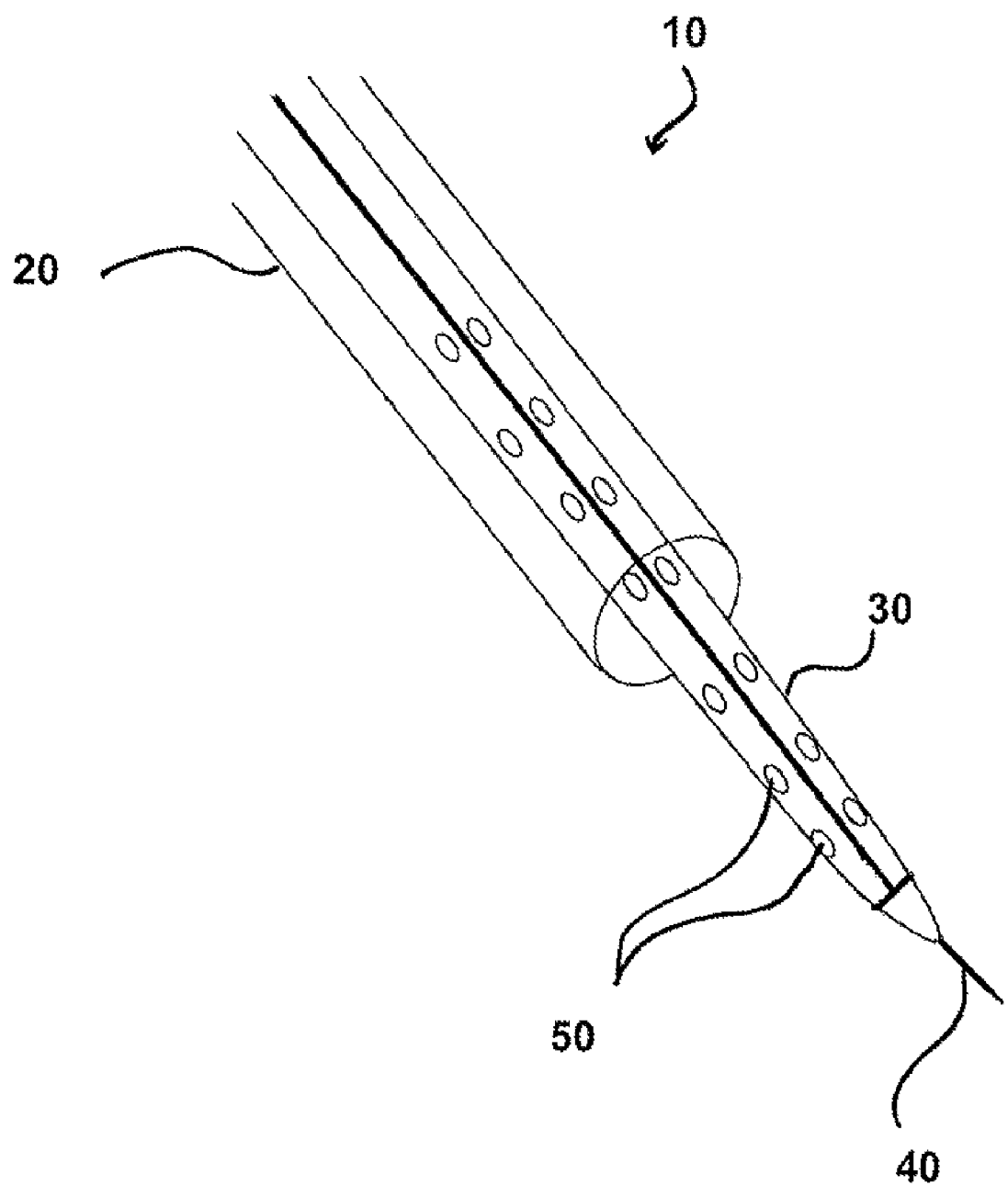
FIG. 1A shows an embodiment of an engagement catheter and an embodiment of a delivery catheter as disclosed herein.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter.

Figure 2A:
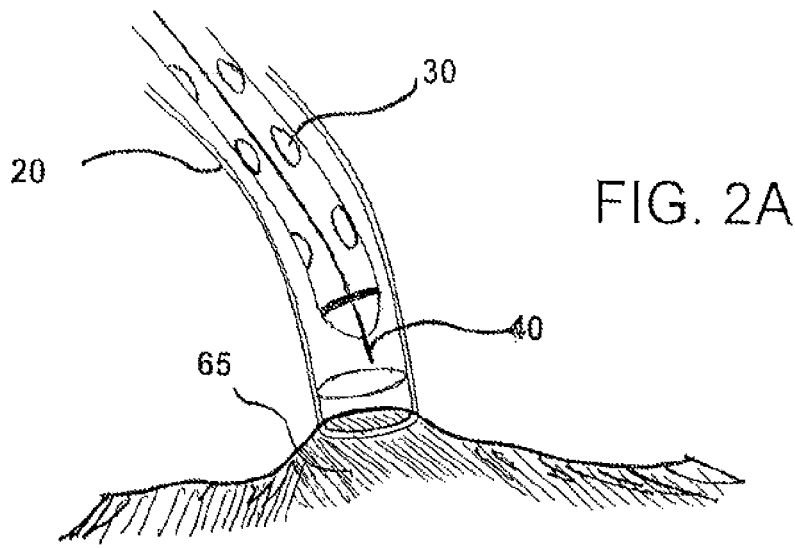
FIG. 2A shows a percutaneous intravascular technique for accessing the pericardial space through a right atrial wall or atrial appendage using the engagement and delivery catheters shown in FIG. 1A.
Figure 2B:
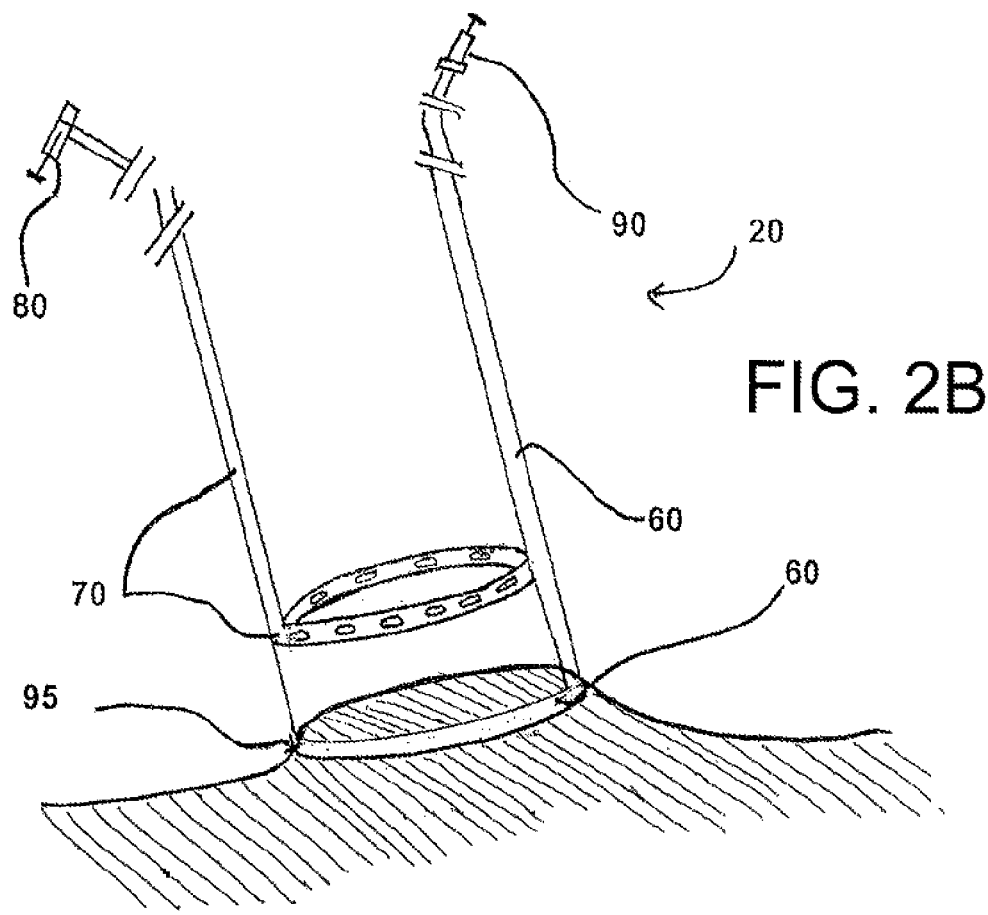
FIG. 2B shows the embodiment of an engagement catheter shown in FIG. 2A.
Figure 2C:
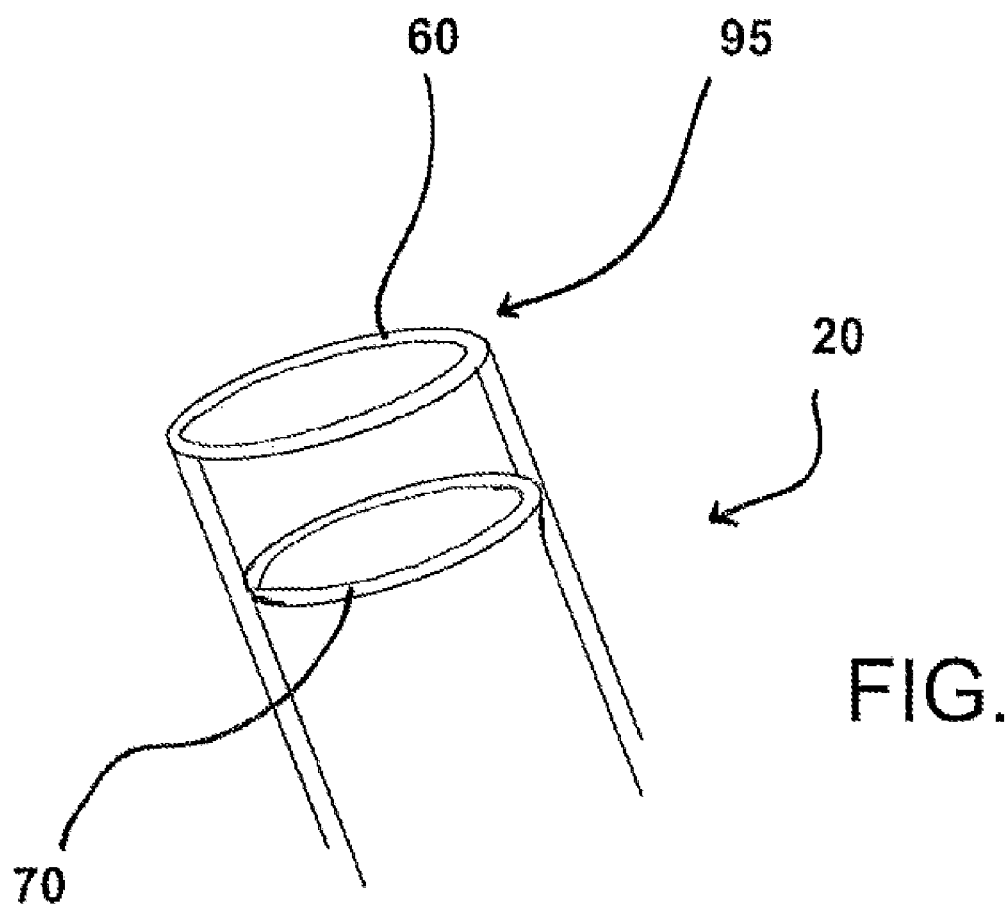
FIG. 2C shows another view of the distal end of the engagement catheter embodiment shown in FIGS. 2A and 2B.

As shown in more detail in FIGS. 2A, 2B, 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Figure 1B:
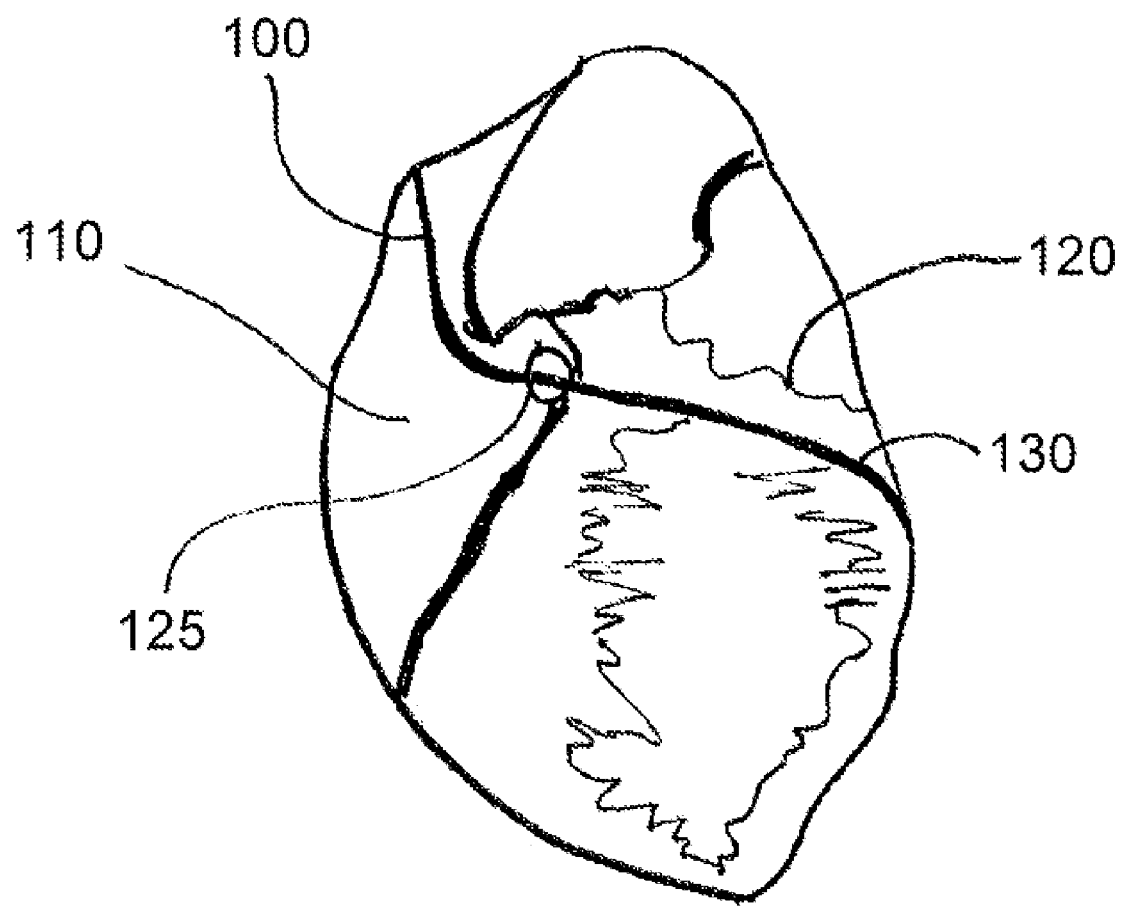
FIG. 1B shows a percutaneous intravascular pericardial delivery using another embodiment of an engagement catheter and another embodiment of a delivery catheter as disclosed herein.

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Flouroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transseptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Referring now to FIG. 3A, the catheter system shown in FIG. 1B is retrieved by pull back through the route of entry. However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity or the heart, as discussed herein; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Figure 4A:
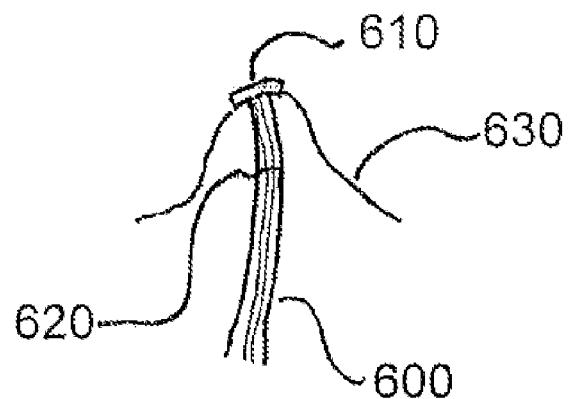
FIG. 4A to 4C show a closure of a hole in the atrial wall using an embodiment as disclosed herein.
Figure 4B:
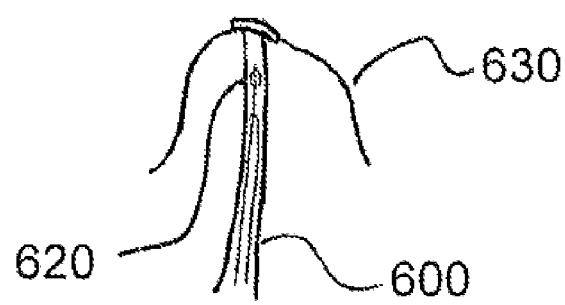
Figure 4C:
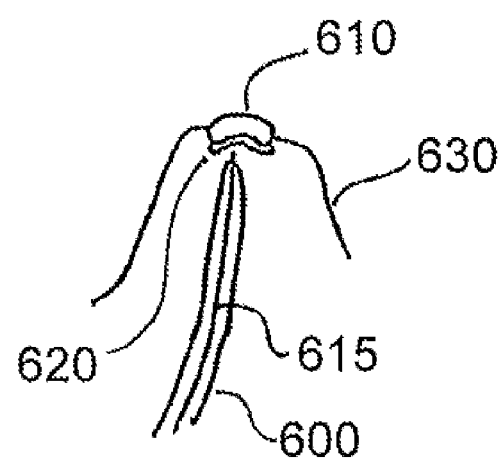

Other examples for sealing the puncture wound in the atrial wall or appendage are shown in FIGS. 4A-4F. Referring now to FIGS. 4A-4C, a sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded to an expanded configuration once it is outside of the catheter. As shown in FIG. 4A, external cover 610 is deployed (in its expanded configuration) on the outside of the atrial wall to seal a puncture wound in the targeted tissue, having already been delivered through the puncture wound into the pericardial space. Internal cover 620 is delivered through engagement catheter 600 (in its folded configuration), as shown in FIGS. 4A and 4B, by an elongated delivery wire 615, to which internal cover 620 is reversibly attached (for example, by a screw-like mechanism). Once internal cover 620 is in position on the inside of atrial wall 630 at the targeted tissue, internal cover 620 is deployed to help seal the puncture wound in the targeted tissue (see FIG. 4C).

Internal cover 620 and external cover 610 may be made from a number of materials, including a shape-memory alloy such as nitinol. Such embodiments are capable of existing in a catheter in a folded configuration and then expanding to an expanded configuration when deployed into the body. Such a change in configuration can result from a change in temperature, for example. Other embodiments of internal and external covers may be made from other biocompatible materials and deployed mechanically.

After internal cover 620 is deployed, engagement catheter 600 releases its grip on the targeted tissue and is withdrawn, leaving the sandwich-type closure to seal the puncture wound, as shown in FIG. 4C. External cover 610 and internal cover 620 may be held in place using a biocompatible adhesive. Similarly, external cover 610 and internal cover 620 may be held in place using magnetic forces, such as, for example, by the inside face (not shown) of external cover 610 comprising a magnet, by the inside face (not shown) of internal cover 620 comprising a magnet, or both inside faces of external cover 610 or internal cover 620 comprising magnets.

Figure 4D:
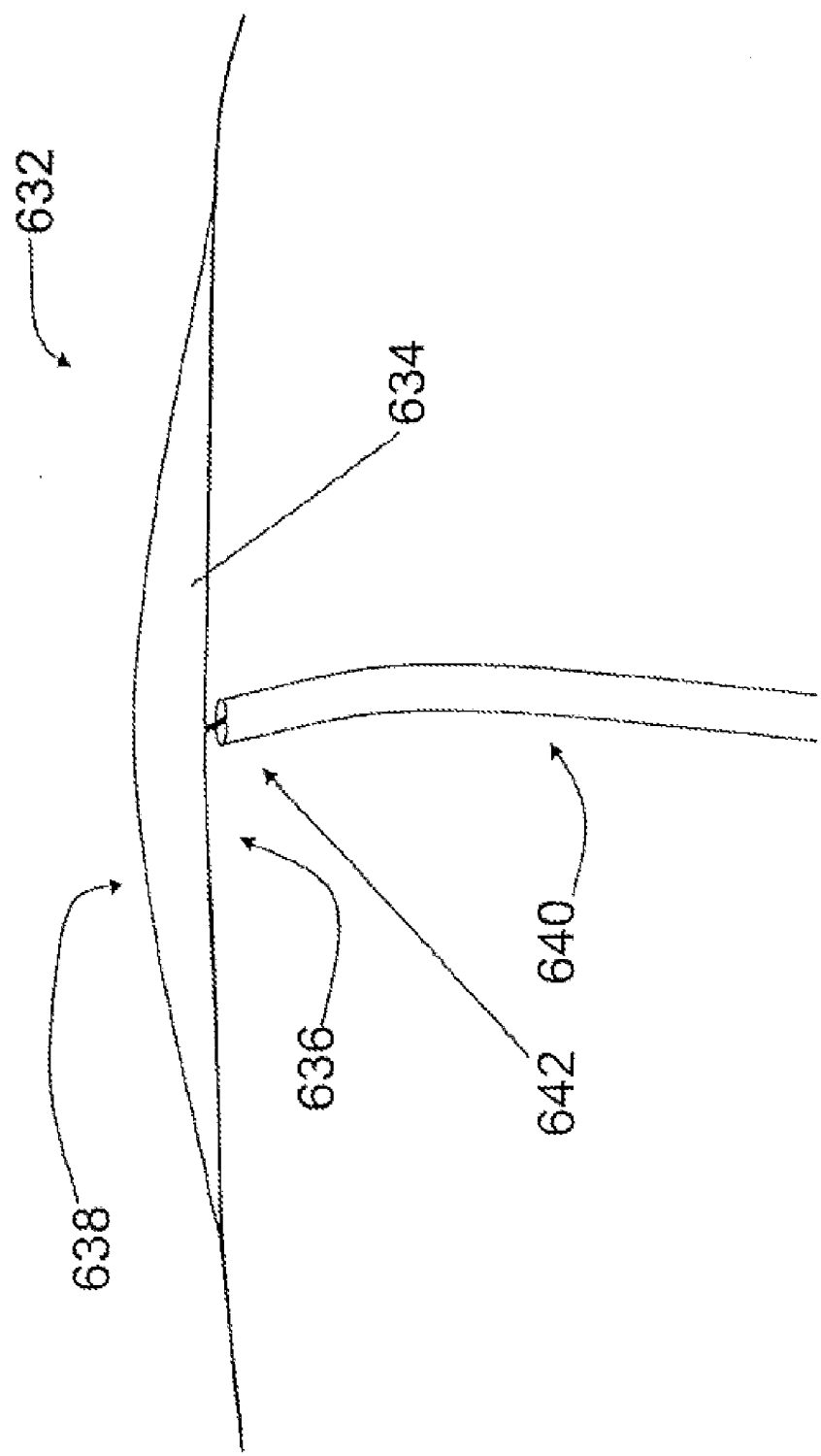
FIG. 4D shows another closure of a hole in cardiac tissue using another embodiment as disclosed herein.

In the embodiment shown in FIGS. 4A, 4B, and 4C, the closure member comprises external cover 610 and internal cover 620. However, in at least certain other embodiments, the closure member need not have two covers. For example, as shown in FIG. 4D, closure member 632 is made of only one cover 634. Cover 634 has a first face 636 and a second face 638, and first face 636 is configured for reversible attachment to distal end 642 of delivery wire 640. Closure member 632 may be made of any suitable material, including nitinol, which is capable of transitioning from a folded configuration to an expanded configuration.

Figure 4E:
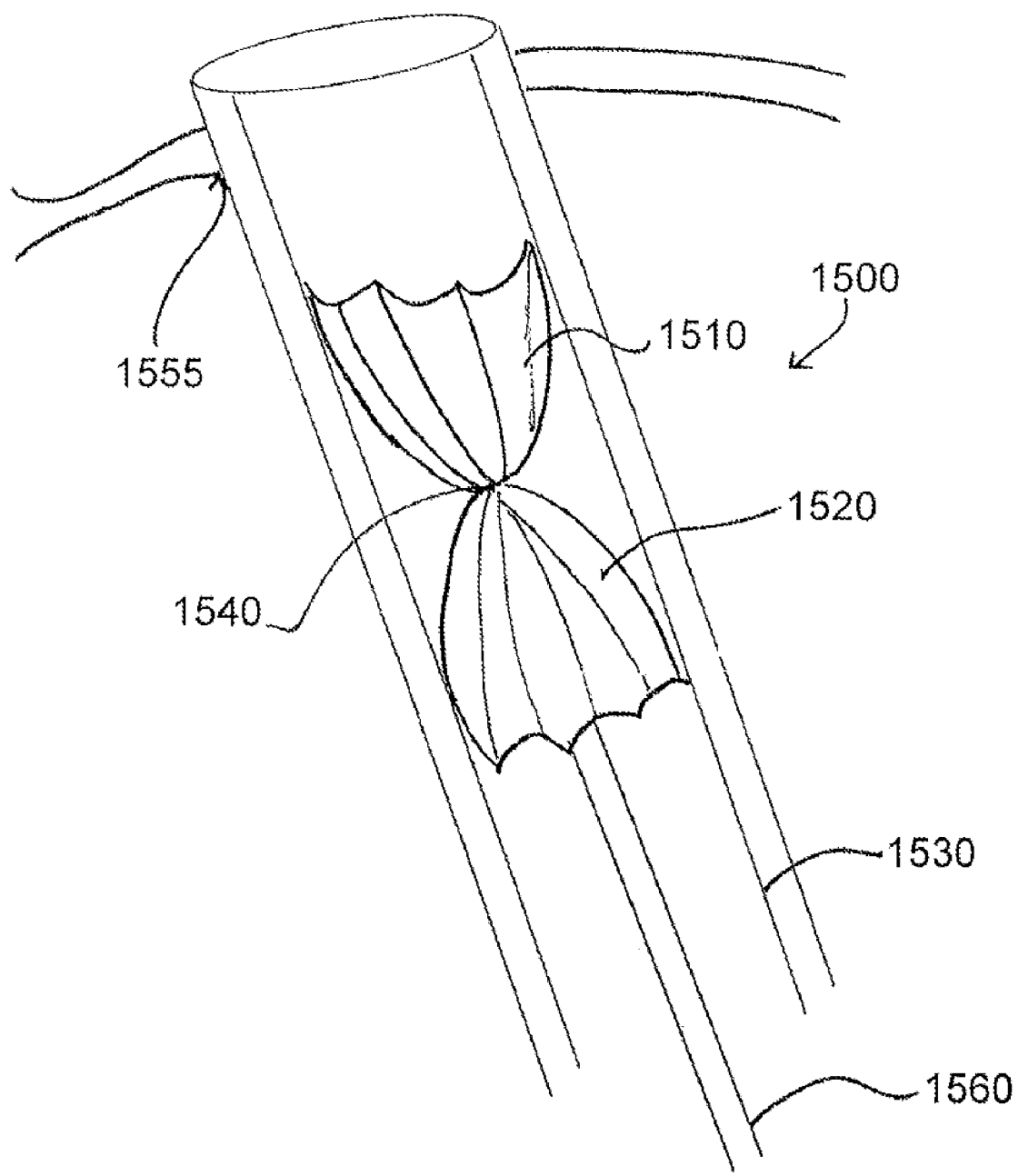
FIG. 4E shows yet another closure of a hole in cardiac tissue using another embodiment as disclosed herein.

In the embodiment shown in FIG. 4E, a closure member 1500 comprises an external cover 1510 and an internal cover 1520 within a delivery catheter 1530. External cover 1510 and internal cover 1520 are attached at a joint 1540, which may be formed, for example, by a mechanical attachment or by a magnetic attachment. In embodiments having a magnetic attachment, each of the external cover and the internal cover may have a ferromagnetic component that is capable of magnetically engaging the other ferromagnetic component.

Delivery catheter 1530 is shown after insertion through hole 1555 of atrial wall 1550. Closure member 1500 may be advanced through delivery catheter 1530 to approach atrial wall 1550 by pushing rod 1560. Rod 1560 may be reversibly attached to internal cover 1520 so that rod 1560 may be disconnected from internal cover 1520 after closure member 1500 is properly deployed. For example, rod 1560 may engage internal cover 1520 with a screw-like tip such that rod 1560 may be easily unscrewed from closure member 1500 after deployment is complete. Alternatively, rod 1560 may simply engage internal cover 1520 such that internal cover 1520 may be pushed along the inside of delivery catheter 1530 without attachment between internal cover 1520 and rod 1560.

Closure member 1500 is advanced through delivery catheter 1530 until external cover 1510 reaches a portion of delivery catheter 1530 adjacent to atrial wall 1550; external cover 1510 is then pushed slowly out of delivery catheter 1530 into the pericardial space. External cover 1510 then expands and is positioned on the outer surface of atrial wall 1550. When external cover 1510 is properly positioned on atrial wall 1550, joint 1540 is approximately even with atrial wall 1550 within hole 1555. Delivery catheter 1530 is then withdrawn slowly, causing hole 1555 to close slightly around joint 1540. As delivery catheter 1530 continues to be withdrawn, internal cover 1520 deploys from delivery catheter 1530, thereby opening into its expanded formation. Consequently, atrial wall 1550 is pinched between internal cover 1520 and external cover 1510, and hole 1555 is closed to prevent leakage of blood from the heart.

Figure 4F:
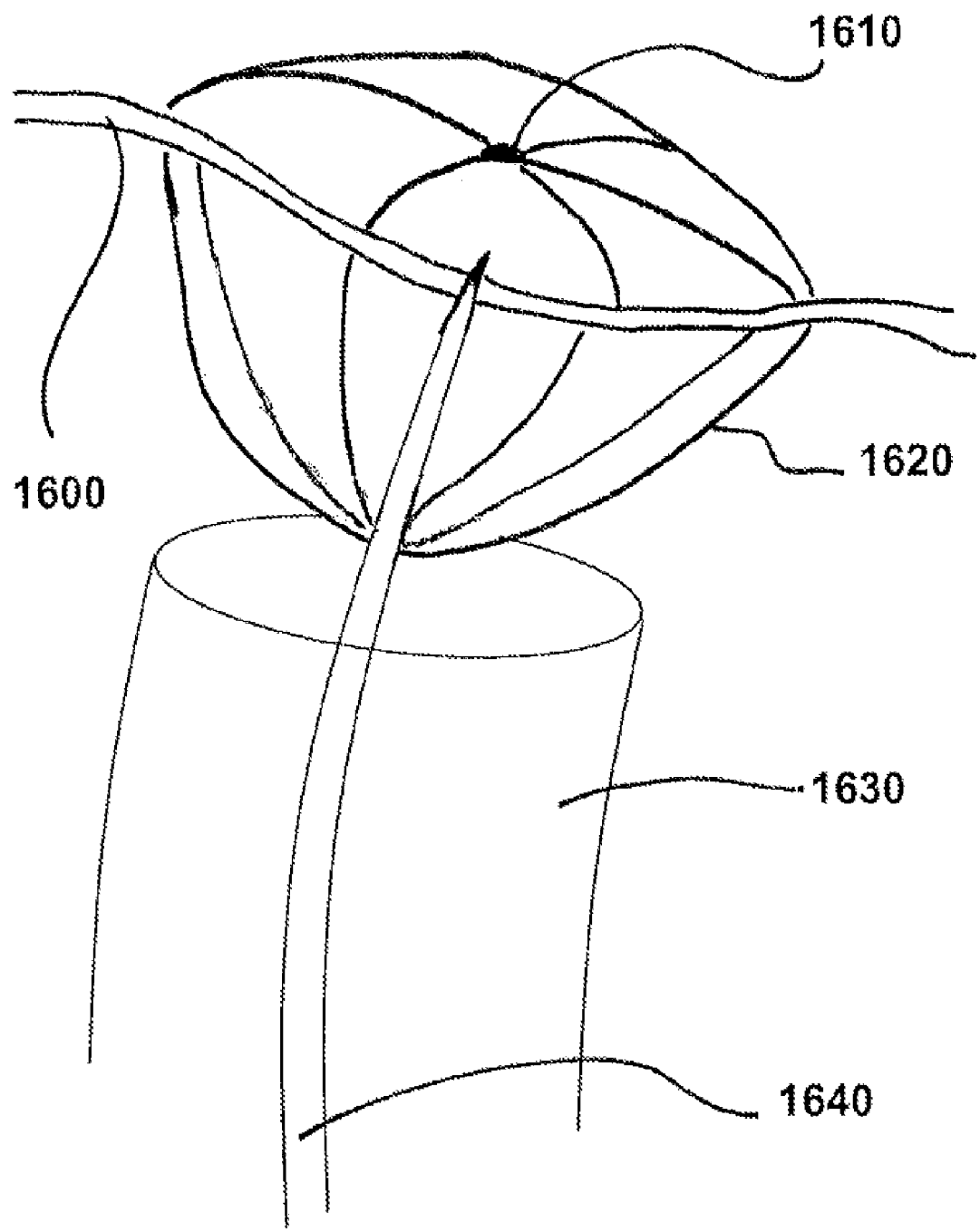
FIG. 4F shows still another closure of a hole in cardiac tissue using another embodiment as disclosed herein.

FIG. 4F shows the occlusion of a hole (not shown) in atrial wall 1600 due to the sandwiching of atrial wall 1600 between an external cover 1610 and an internal cover 1620. External cover 1610 is shown deployed on the outside surface of atrial wall 1600, while delivery catheter 1630 is deployed on the inside surface of atrial wall 1600. As shown, rod 1640 is engaged with internal cover 1620, and delivery catheter 1650 is in the process of being withdrawn, which allows internal cover 1620 to fully deploy. Rod 1640 is then withdrawn through delivery catheter 1630. An engagement catheter (not shown) may surround delivery catheter 1650, as explained more fully herein.

Other examples for sealing a puncture wound in the cardiac tissue are shown in FIGS. 12-15. Referring now to FIG. 12A, there is shown a plug 650 having a first end 652, a second end 654, and a hole 656 extending from first end 652 to second end 654. Plug 650 may be made from any suitable material, including casein, polyurethane, silicone, and polytetrafluoroethylene. Wire 660 has been slidably inserted into hole 656 of plug 650. Wire 660 may be, for example, a guide wire or a pacing lead, so long as it extends through the hole in the cardiac tissue (not shown). As shown in FIG. 12A, first end 652 is covered with a radiopaque material, such as barium sulfate, and is therefore radiopaque. This enables the clinician to view the placement of the plug in the body using radiographic imaging. For example, the clinician can confirm the location of the plug during the procedure, enabling a safer and more effective procedure for the patient.

As shown in FIG. 12A, first end 652 of plug 650 has a smaller diameter than second end 654 of plug 650. Indeed, plug 680 shown FIG. 12B and plug 684 shown in FIGS. 13 and 14 have first ends that are smaller in diameter than their respective second ends. However, not all embodiments of plug have a first end that is smaller in diameter than the second end. For example, plug 682 shown in FIG. 12C has a first end with a diameter that is not smaller than the diameter of the second end. Both types of plug can be used to close holes in cardiac tissue.

Referring again to FIG. 12A, elongated shaft 670 has a proximal end (not shown), a distal end 672, and a lumen 674 extending from the proximal end to distal end 672. Although no catheter is shown in FIG. 12A, plug 650, wire 660, and shaft 670 are configured for insertion into a lumen of a catheter (see FIG. 14), such as an embodiment of an engagement catheter disclosed herein. Plug 650 and shaft 670 are also configured to be inserted over wire 660 and can slide along wire 660 because each of lumen 656 of plug 650 and lumen 674 of shaft 670 is slightly larger in circumference than wire 660.

Figure 13:
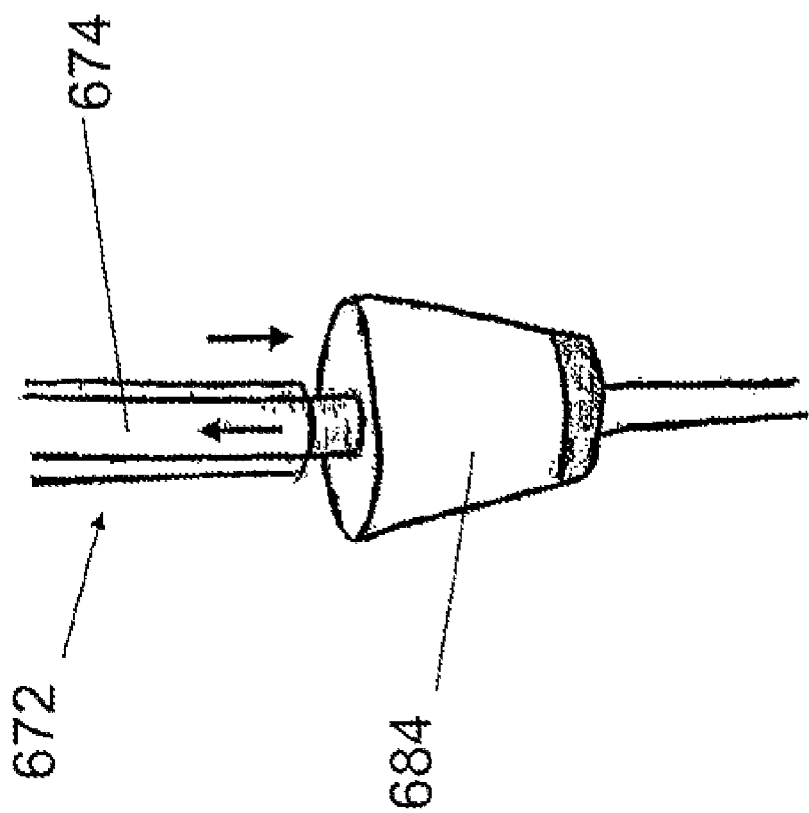
FIG. 13 shows another embodiment of a system for closing a hole in cardiac tissue, as disclosed herein.
Figure 14:
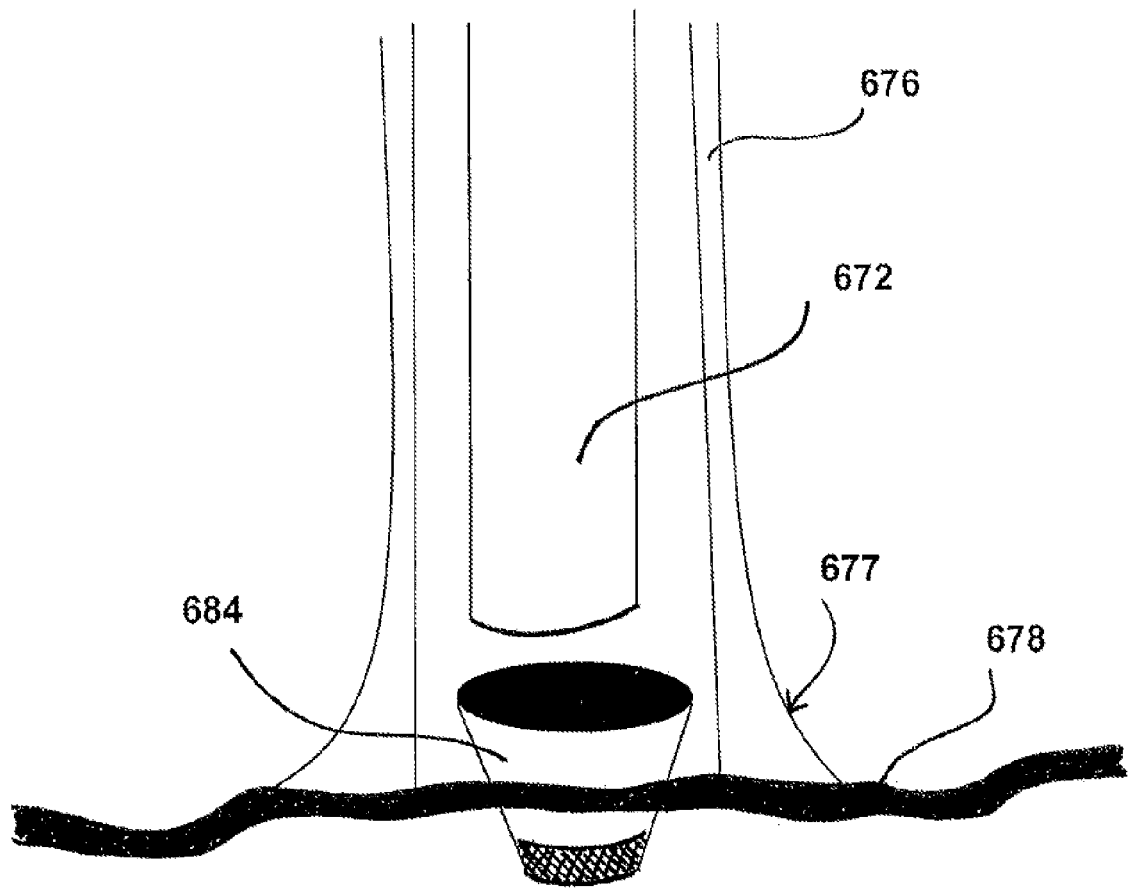
FIG. 14 shows another embodiment of a system for closing a hole in cardiac tissue, as disclosed herein.

As shown in FIGS. 13 and 14, shaft 672 is used to push plug 684 along wire 674 within elongated tube 676 to and into the hole in the targeted cardiac tissue 678. Distal end 677 of elongated tube 676 is shown attached to cardiac tissue 678, but distal end 677 need not be attached to cardiac tissue 678 so long as distal end 677 is adjacent to cardiac tissue 678. Once plug 684 is inserted into the hole, wire 674 may be withdrawn from the hole in plug 684 and the interior of the heart (not shown) and shaft 672 is withdrawn from elongated tube 676. In some embodiments, the plug is self-sealing, meaning that the hole of the plug closes after the wire is withdrawn. For example, the plug may be made from a dehydrated protein matrix, such as casein or ameroid, which swells after soaking up fluid. After shaft 672 is withdrawn, elongated tube 676 can be withdrawn from the heart.

It should be noted that, in some embodiments, the wire is not withdrawn from the hole of the plug. For example, where the wire is a pacing lead, the wire may be left within the plug so that it operatively connects to the CRT device.

Referring now to FIG. 12B, there is shown a plug 680 that is similar to plug 684. However, plug 680 comprises external surface 681 having a ridge 683 that surrounds plug 680 in a helical or screw-like shape. Ridge 683 helps to anchor plug 680 into the hole of the targeted tissue (not shown). Other embodiments of plug may include an external surface having a multiplicity of ridges surrounding the plug, for example, in a circular fashion.

Figure 15A:
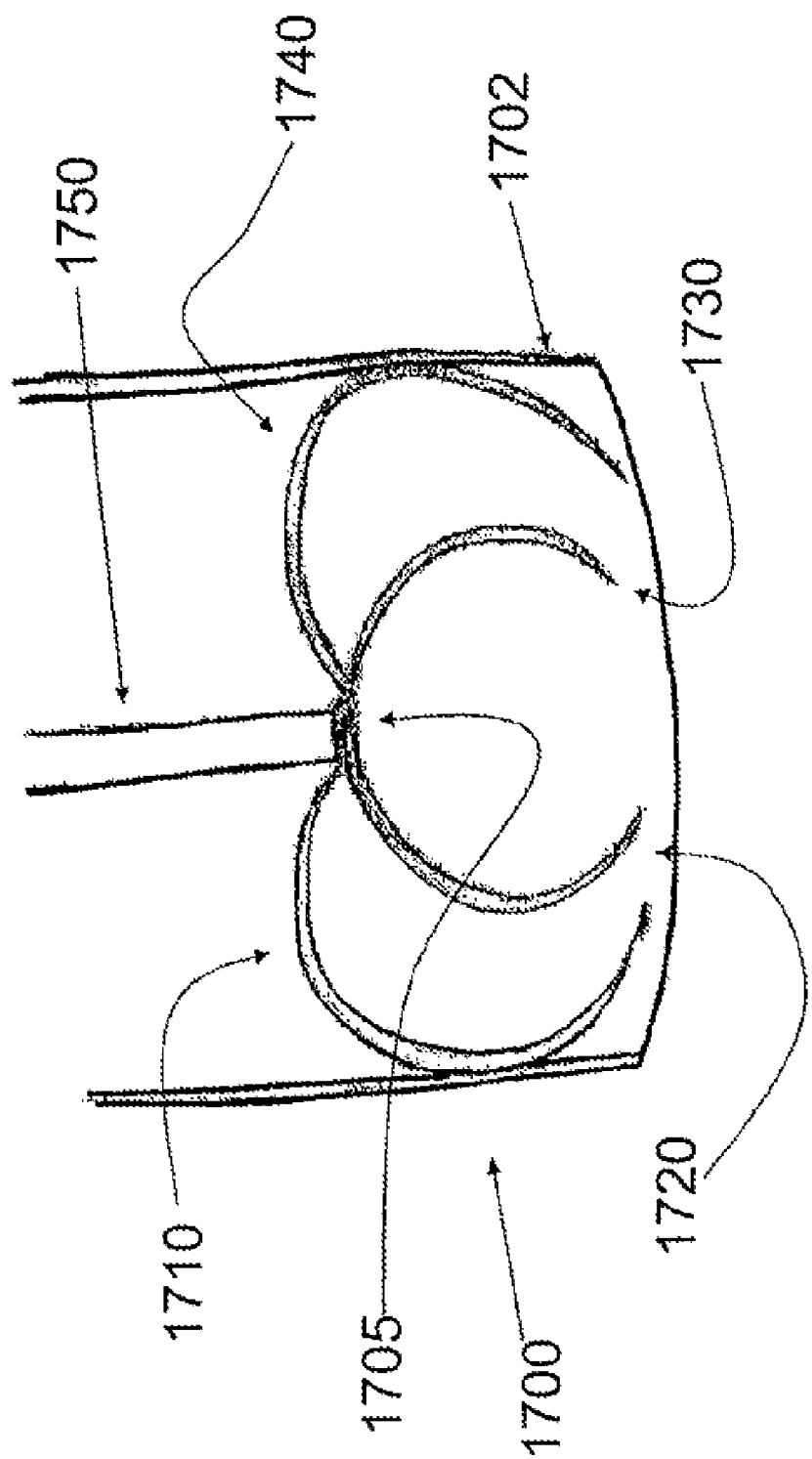
FIG. 15A shows another embodiment of a system for closing a hole in cardiac tissue, as disclosed herein.
Figure 15B:
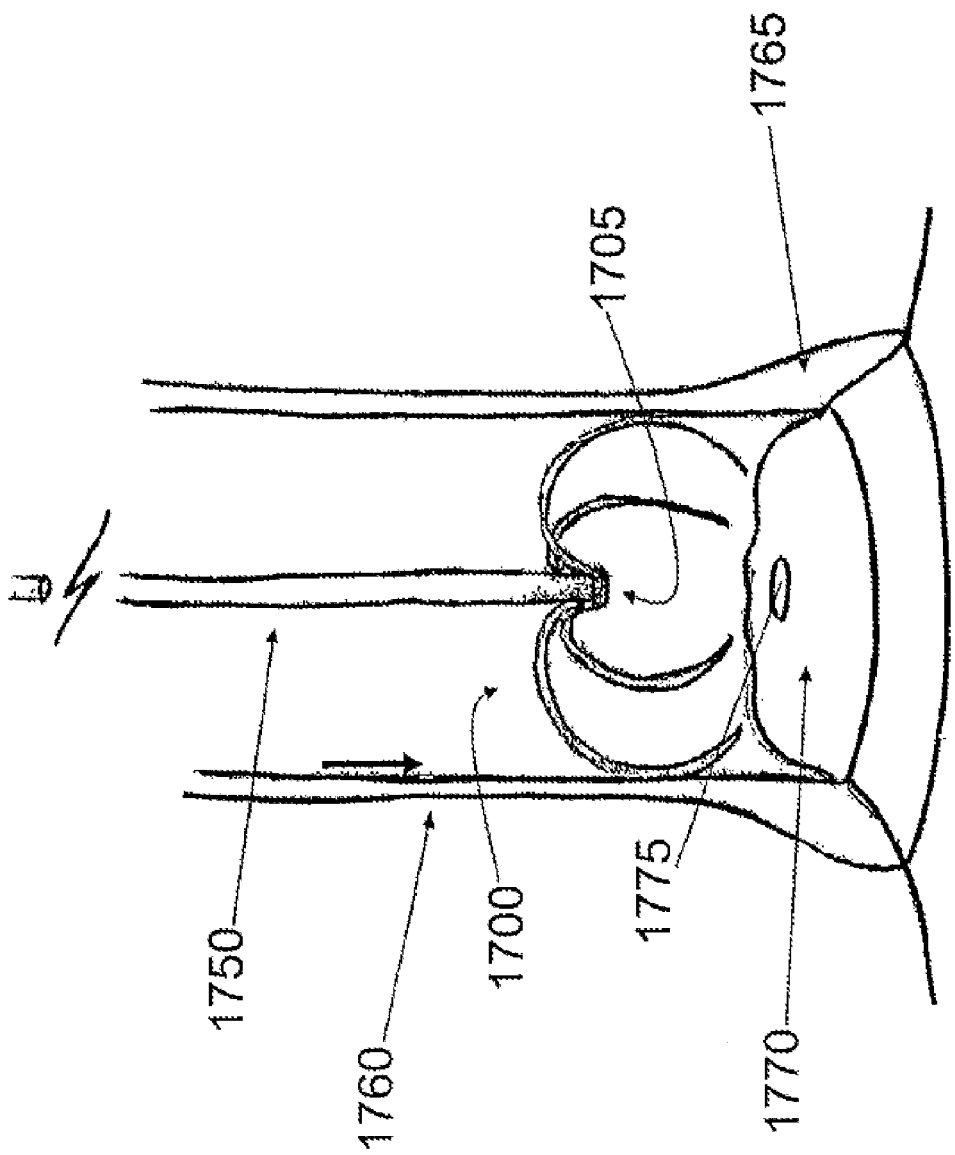
FIG. 15B shows the embodiment of FIG. 15A approaching cardiac tissue.

FIGS. 15A-15C show yet another embodiment of a closure member for closing a hole in a tissue. Spider clip 1700 is shown within catheter 1702 and comprises a head 1705 and a plurality of arms 1710, 1720, 1730, and 1740. Each of arms 1710, 1720, 1730, and 1740 is attached at its proximal end to head 1705. Although spider clip 1700 has four arms, other embodiments of spider clip include fewer than, or more than, four arms. For example, some embodiments of spider clip have three arms, while others have five or more arms.

Referring again to FIGS. 15A-15C, arms 1710, 1720, 1730, and 1740 may be made from any flexible biocompatible metal that can transition between two shapes, such as a shape-memory alloy (e.g., nitinol) or stainless steel. Spider clip 1700 is capable of transitioning between an open position (see FIG. 15A), in which the distal ends of its arms 1710, 1720, 1730, and 1740 are spaced apart, and a closed position (see FIG. 15C), in which the distal ends of arms 1710, 1720, 1730, and 1740 are gathered together. For embodiments made from a shape-memory alloy, the clip can be configured to transition from the open position to the closed position when the metal is warmed to approximately body temperature, such as when the clip is placed into the cardiac tissue. For embodiments made from other types of metal, such as stainless steel, the clip is configured in its closed position, but may be transitioned into an open position when pressure is exerted on the head of the clip. Such pressure causes the arms to bulge outward, thereby causing the distal ends of the arms to separate.

In this way, spider clip 1700 may be used to seal a wound or hole in a tissue, such as a hole through the atrial wall. For example, FIG. 15B shows spider clip 1700 engaged by rod 1750 within engagement catheter 1760. As shown, engagement catheter 1760 has a bell-shaped suction port 1765, which, as disclosed herein, has aspirated cardiac tissue 1770. Cardiac tissue 1770 includes a hole 1775 therethrough, and suction port 1765 fits over hole 1775 so as to expose hole 1775 to spider clip 1700.

Rod 1750 pushes spider clip 1700 through engagement catheter 1760 to advance spider clip 1700 toward cardiac tissue 1770. Rod 1750 simply engages head 1705 by pushing against it, but in other embodiments, the rod may be reversibly attached to the head using a screw-type system. In such embodiments, the rod may be attached and detached from the head simply by screwing the rod into, or unscrewing the rod out of, the head, respectively.

In at least some embodiments, the spider clip is held in its open position during advancement through the engagement catheter by the pressure exerted on the head of the clip by the rod. This pressure may be opposed by the biasing of the legs against the engagement catheter during advancement.

Referring to FIG. 15C, spider clip 1700 approaches cardiac tissue 1770 and eventually engages cardiac tissue 1770 such that the distal end of each of arms 1710, 1720, 1730, and 1740 contacts cardiac tissue 1670. Rod 1750 is disengaged from spider clip 1700, and spider clip 1700 transitions to its closed position, thereby drawing the distal ends of arms 1710, 1720, 1730, and 1740 together. As the distal ends of the arms are drawn together, the distal ends grip portions of cardiac tissue 1770, thereby collapsing the tissue between arms 1710, 1720, 1730, and 1740 such that hole 1775 is effectively closed.

Rod 1750 is then withdrawn, and engagement catheter 1760 is disengaged from cardiac tissue 1770. The constriction of cardiac tissue 1770 holds hole 1775 closed so that blood does not leak through hole 1775 after engagement catheter 1760 is removed. After a relatively short time, the body's natural healing processes permanently close hole 1775. Spider clip 1700 may remain in the body indefinitely.

Figure 16A:
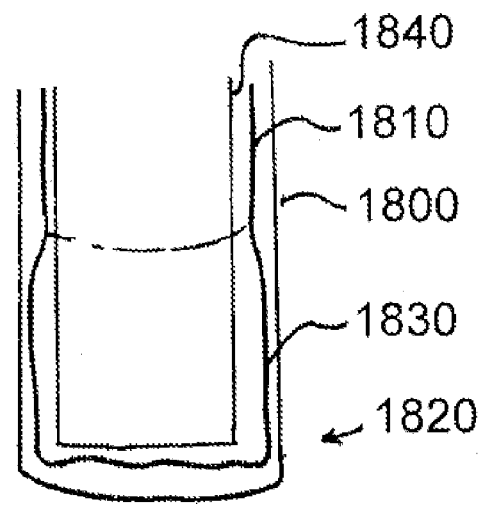
FIG. 16A shows an embodiment of a portion of an apparatus for engaging a tissue having a skirt positioned substantially within a sleeve, as disclosed herein.
Figure 16B:
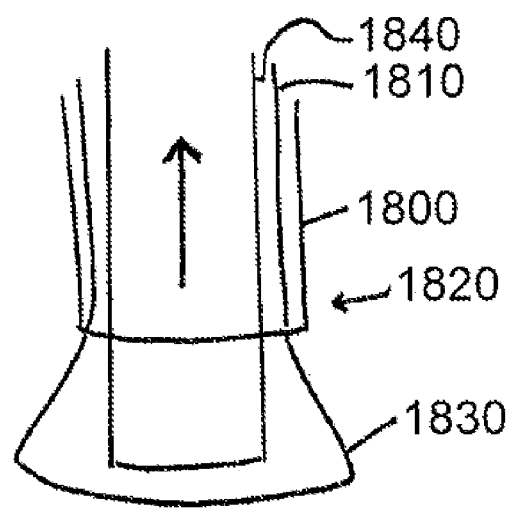
FIG. 16B shows another embodiment of a portion of an apparatus for engaging a tissue, as disclosed herein.
Figure 16C:
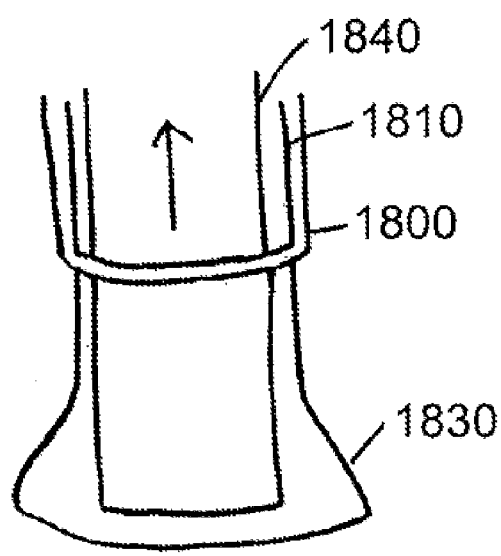
FIG. 16C shows an embodiment of a portion of an apparatus for engaging a tissue having a skirt positioned substantially outside of a sleeve, as disclosed herein.

FIGS. 16A, 16B, and 16C show an embodiment of a portion of an apparatus for engaging a tissue as disclosed herein. As shown in FIG. 16A, a sleeve 1800 is present around at least a portion of an engagement catheter 1810. Sleeve 1800, as described herein, may comprise a rigid or flexible tube having a lumen therethrough, appearing around the outside of engagement catheter 1810 and slidingly engaging engagement catheter 1810. In at least the embodiment shown in FIG. 16A, the distal end 1820 of engagement catheter 1810 comprises a skirt 1830, shown in FIG. 16A as being housed within sleeve 1800. A delivery catheter 1840 may be present within engagement catheter 1810 as shown to facilitate the delivery of a product (gas, liquid, and/or particulate(s)) to a target site. In this embodiment, delivery catheter 1840 is present at least partially within the lumen of engagement catheter 1810, and engagement catheter is placed at least partially within the lumen of sleeve 1800.

Referring now to FIG. 16B, an embodiment of an apparatus as shown in FIG. 16A or similar to the embodiment shown in FIG. 16A is shown with sleeve 1800 being "pulled back" from the distal end of engagement catheter 1810. As shown in FIG. 16B, as sleeve 1800 is pulled back (in the direction of the arrow), skirt 1830 becomes exposed, and as sleeve 1800 is no longer present around skirt 1830, skirt 1830 may optionally expand into a frusto-conical ("bell-shaped") skirt 1830. Skirt 1830 may be reversibly deformed (collapsed) when present within the lumen of sleeve 1800 as shown in FIG. 16A and in FIG. 18A described in further detail herein. It can be appreciated that many alternative configurations of skirt 1830 to the frusto-conical configuration may exist, including an irregular frusto-conical configuration, noting that a configuration of skirt 1830 having a distal portion (closest to a tissue to be engaged) larger than a proximal position may benefit from suction of a larger surface area of a tissue as described in further detail herein.

FIG. 16C shows an embodiment of an apparatus described herein having an expanded skirt 1830. As shown in FIG. 16C, sleeve 1800 has been pulled back (in the direction of the arrow) so that the expanded configuration of skirt 1830 may be present to engage a tissue (not shown).

FIGS. 17A and 17B shown alternative embodiments of a portion of an apparatus for engaging a tissue as described herein. FIGS. 17A and 17B each show a sleeve 1800, an engagement catheter 1810 having a skirt 1830, and a delivery catheter 1840. In each figure, skirt 1830 is shown engaging a surface of a tissue 1850. In the embodiments shown in FIGS. 17A and 17B, the relative sizes of the sleeves 1800, engagement catheters 1810, and delivery catheters 1840 are similar as shown, but the relative sizes of the skirts 1830 of the engagement catheters 1810 are clearly different. The exemplary embodiment of the portion of an apparatus for engaging a tissue shown in FIG. 17A comprises a skirt 1830 of the same or substantially similar relative size as the engagement catheter 1810, meaning that the diameters of the engagement catheter 1810 and the skirt 1830 shown in FIG. 17A are approximately the same. Conversely, the exemplary embodiment of the portion of an apparatus for engaging a tissue shown in FIG. 17B comprises a skirt 1830 notably larger than the engagement catheter 1810, meaning that the diameters of the engagement catheter 1810 and the skirt 1830 at its widest point shown in FIG. 17B are notably different. As shown in FIG. 17B, as skirt 1830 extends from engagement catheter 1810 to tissue 1850, the diameter of skirt 1830 increases. As such, skirt 1830 of the embodiment shown in FIG. 17B may engage a larger surface area of a tissue (shown by 1860) than the embodiment of the skirt 1830 shown in FIG. 17A. The ability to engage a larger surface area of a tissue 1850 by skirt 1830 allows a better reversible engagement of a tissue 1850 when a vacuum is provided as described in detail herein. This improved suction allows a person using such an apparatus to more effectively engage a tissue 1850 than would otherwise be possible when skirt 1830 engages a smaller surface area of a tissue.

FIGS. 18A and 18B show perspective views of an embodiment of a portion of an apparatus for engaging a tissue. FIG. 18A represents an embodiment whereby a skirt 1830 of an engagement catheter 1810 is positioned substantially within a sleeve 1800. FIG. 18B represents an embodiment whereby a skirt 1830 of an engagement catheter 1810 is positioned outside of sleeve 1800. As such, the positioning of skirt 1830 within sleeve 1800 can be seen in the embodiments of FIGS. 16A and 18A, and the positioning of skirt 1830 outside of sleeve 1800 can be seen in the embodiments of FIGS. 16C and 18B.

As shown in FIG. 18A, skirt 1830 of engagement catheter 1810 is positioned within sleeve 1800, whereby the configuration of skirt 1830 is collapsed so that skirt 1830 may fit within sleeve 1800. As sleeve 1800 moves in the direction of the arrow shown in FIG. 18B, skirt 1830 becomes exposed and its configuration is allowed to expand because there are no constraints provided by the inner wall of sleeve 1800.

The embodiments shown in FIGS. 18A and 18B also show an exemplary embodiment of a configuration of an engagement catheter 1810. As shown in FIG. 18B, engagement catheter 1810 defines a number of apertures (representing lumens) present at the distal end of engagement catheter 1810 (at the proximal end of skirt 1830), including, but not limited to, one or more vacuum ports 1870 (representing the aperture at or near the distal end of a vacuum tube), and a delivery port 1880 (representing the aperture at or near the distal end of a delivery tube). A vacuum source (not shown) may be coupled to a suction port located at a proximal end of one or more vacuum tubes as described herein, whereby gas, fluid, and/or particulate(s) may be introduced into one or more vacuum ports 1870 by the introduction of a vacuum at a vacuum port. Gas, fluid, and/or particulate(s) may be introduced from delivery aperture 1880 to a tissue (not shown in FIG. 18A or 18B).

As shown by the exemplary embodiments of FIGS. 17A and 17B, the ability for a user of such an apparatus for engaging a tissue to obtain proper suction depends at least in part on the relative placement of skirt 1830 and delivery catheter 1840 at or near a tissue 1850. As described in detail herein regarding the exemplary embodiment shown in FIG. 5D, if a vacuum source provides suction through one or more vacuum ports 1870 (shown in FIGS. 18A and 18B), but skirt 1830 has not effectively engaged a tissue 1850, gas, fluid, and/or particulate(s) in the area of tissue 1850 and/or gas, fluid and/or particulate(s) delivered via delivery catheter 1840 to the area of tissue 1850 may be aspirated by one or more vacuum ports 1870. In a situation where skirt 1830 has effectively engaged a tissue 1850 but where delivery catheter 1840 has not engaged a tissue 1850, any gas, liquid, and/or particulate(s) delivered by delivery catheter 1840 may be aspirated by one or more vacuum ports 1870. In a situation where skirt 1830 and delivery catheter 1840 have effectively engaged a tissue 1850, most, if not all, of any gas, liquid, and/or particulate(s) delivered by delivery catheter 1840 to tissue 1850 would not be aspirated by one or more vacuum ports 1870 as the placement of delivery catheter 1840 on or within tissue 1850 would provide direct delivery at or within tissue 1850.

Figure 19:
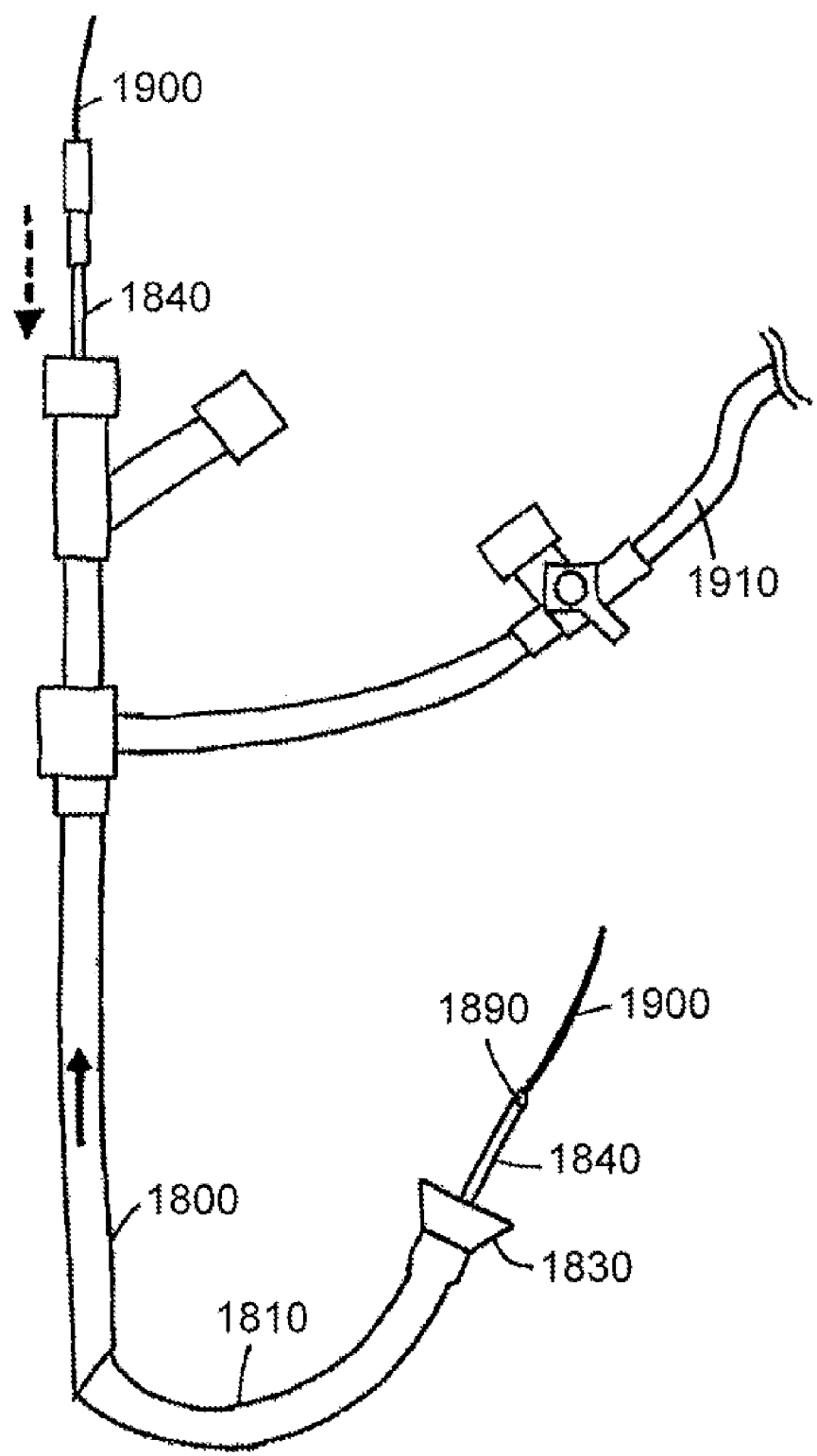
FIG. 19 shows an embodiment of a system for engaging a tissue, as disclosed herein.

An exemplary embodiment of a system and/or device for engaging a tissue as described herein is shown in Fla 19. As shown in FIG. 19, an exemplary apparatus shows a sleeve 1800 which has been moved in the direction of the arrow to reveal skirt 1830 at the distal end of engagement catheter 1810, allowing skirt to resume an expanded, frusto-conical configuration. As shown in this embodiment, delivery catheter 1840 has been introduced at the proximal end of the apparatus (in the direction shown by the dashed arrow), allowing delivery catheter 1840 to exit out of a delivery lumen (not shown) at the distal end of engagement catheter 1840. A needle 1890 may be present at the distal end of delivery catheter 1840, facilitating the potential puncture of a tissue (not shown) to allow the distal end of delivery catheter 1840 to enter a tissue.

In addition, and as shown in the exemplary embodiment of FIG. 19, a lead 1900 may be introduced into delivery catheter 1840 (in the direction shown by the dashed arrow), whereby the distal end of lead 1900 may exit an aperture of needle 1890 and optionally enter a tissue and/or a lumen of a tissue. As described herein, any number of suitable types of leads 1900 may be used with the delivery catheters described herein, including sensing leads and/or pacing leads. A vacuum source 1910 may also provide a source of vacuum to such an apparatus to allow skirt 1830 to engage a tissue using suction.

The exemplary embodiment of an apparatus for engaging a tissue as shown in FIG. 19 comprises an engagement catheter 1810 having a curvature. Such a curved engagement catheter 1810 allows a user of such an apparatus, for example, to insert a portion of the apparatus into a body or tissue from one direction, and engage a tissue with skirt 1830, delivery catheter 1840, needle 1890, and/or lead 1900 from another direction. For example, a user may introduce a portion of an apparatus from one side of the heart, and the apparatus may engage the heart from a different direction than the direction of introduction of the apparatus.

It can also be appreciated that an exemplary embodiment of an apparatus of the present disclosure may be used to engage an internal portion of an organ. As previously referenced herein, such an apparatus may be used to engage the surface of a tissue. However, it can be appreciated that such a tissue may be an outer surface of any number of tissues, including, but not limited to, a heart, lungs, intestine, stomach, or any number of other organs or tissues. It can also be appreciated that some of these types of organs or tissues, including the heart for example, may have one or more internal tissue surfaces capable of being engaged by an apparatus of the present disclosure. For example, a user of such an apparatus may use the apparatus to engage the septum of the heart dividing one side of the heart from another. Such use may facilitate the delivery of a gas, liquid, and/or particulate(s) to a particular side of the heart, as such a targeted delivery may provide beneficial effects, including, but not limited to, the ability to deliver a lead to pace the inner wall of the left side of the heart.

Figure 20A:
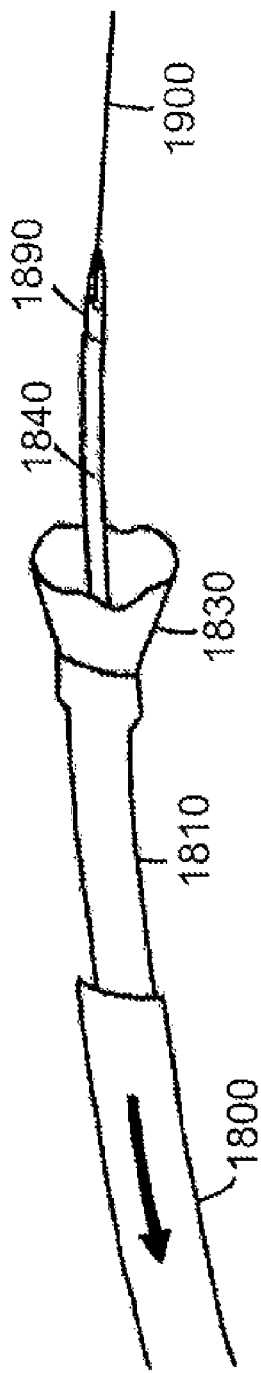
FIG. 20A shows an embodiment of a portion of an apparatus for engaging a tissue having a lead positioned therethrough, as disclosed herein.
Figure 20B:
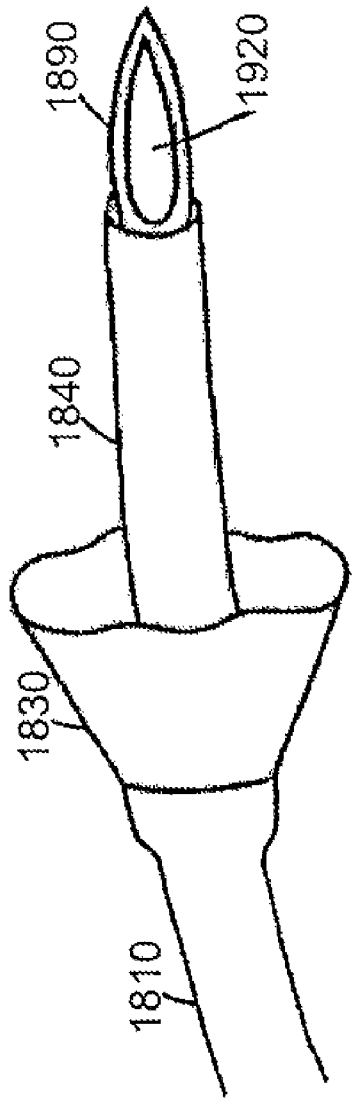
FIG. 20B shows an embodiment of a portion of an apparatus for engaging a tissue showing a needle, as disclosed herein.
Figure 20C:
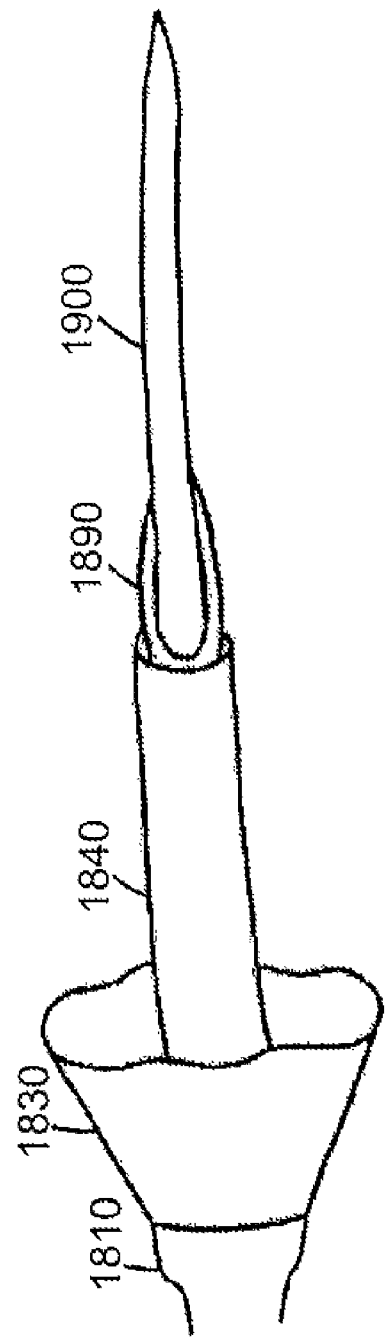
FIG. 20C shows the embodiment of FIG. 20B having a lead positioned therethrough.

Referring now to FIGS. 20A, 20B, and 20C, embodiments of a portion of an apparatus for engaging a tissue according to the present disclosure are shown. As shown in FIG. 20A, an exemplary embodiment of a portion of an apparatus for engaging a tissue comprises sleeve 1800 slidingly engaging engagement catheter 1810, and when sleeve 1800 is slid in the direction of the arrow shown, skirt 1830 is revealed, having an expanded, optionally frusto-conical configuration as shown. Delivery catheter 1840 may exit out of a delivery lumen (not shown), with needle 1890 present at the distal end of delivery catheter 1840. As shown in the embodiment of FIG. 20A, lead 1900 is present, exiting out of an aperture of needle 1890.

FIGS. 20B and 20C show a closer view of an embodiment of a portion of an apparatus for engaging a tissue according to the present disclosure than is shown in FIG. 20A. As shown in FIGS. 20B and 20C, aperture 1920 of needle 1890 is shown, and as shown in FIG. 20C, lead 1900 may exit aperture 1920 of needle 1890.

Referring now to FIGS. 5A, 5B, 5C, and 5D, there is shown another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

Figure 5D:
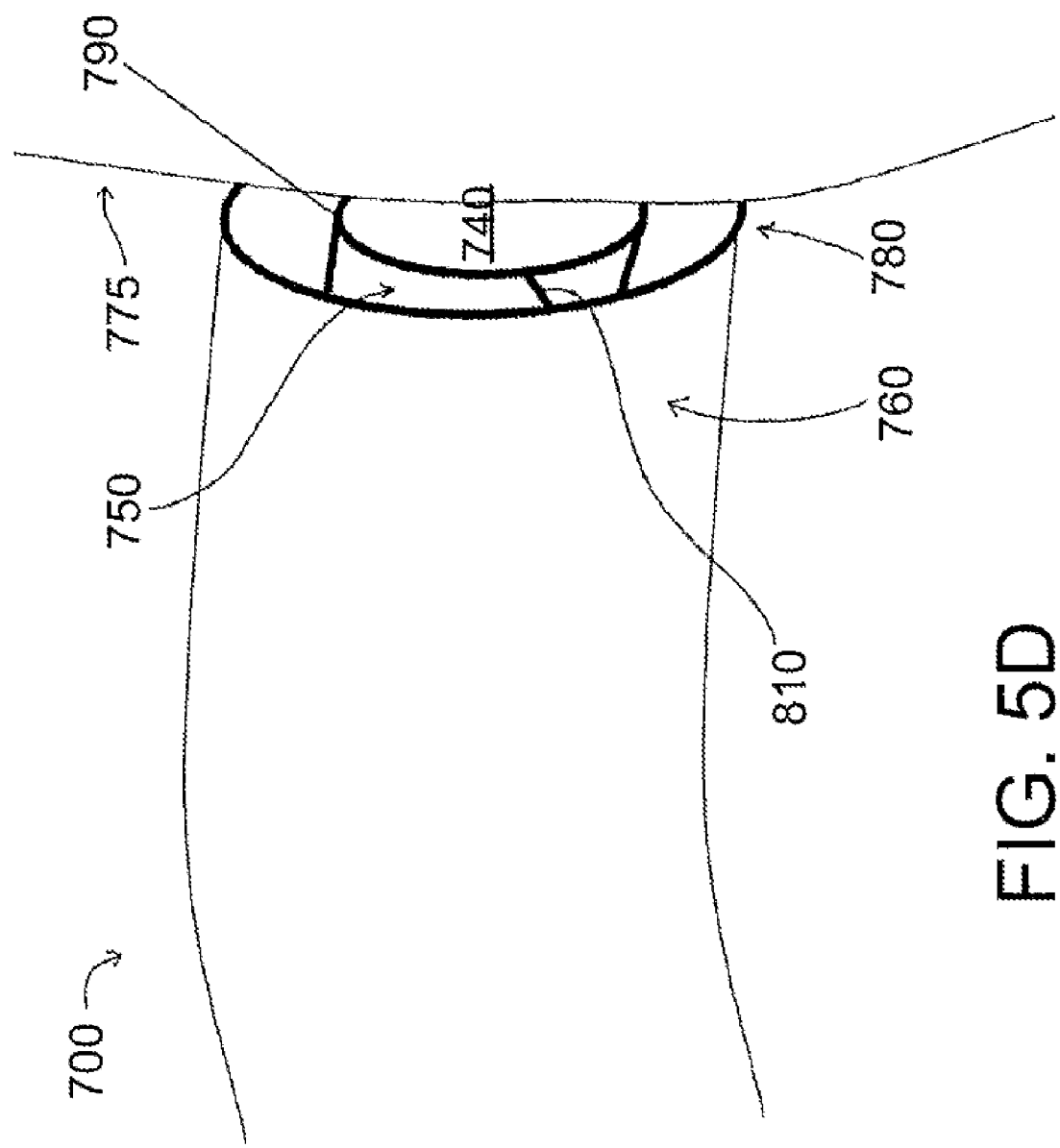
FIG. 5D shows the engagement catheter shown in FIG. 5A approaching a heart wall from inside of the heart.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tampondae) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads (as discussed herein); (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 7:
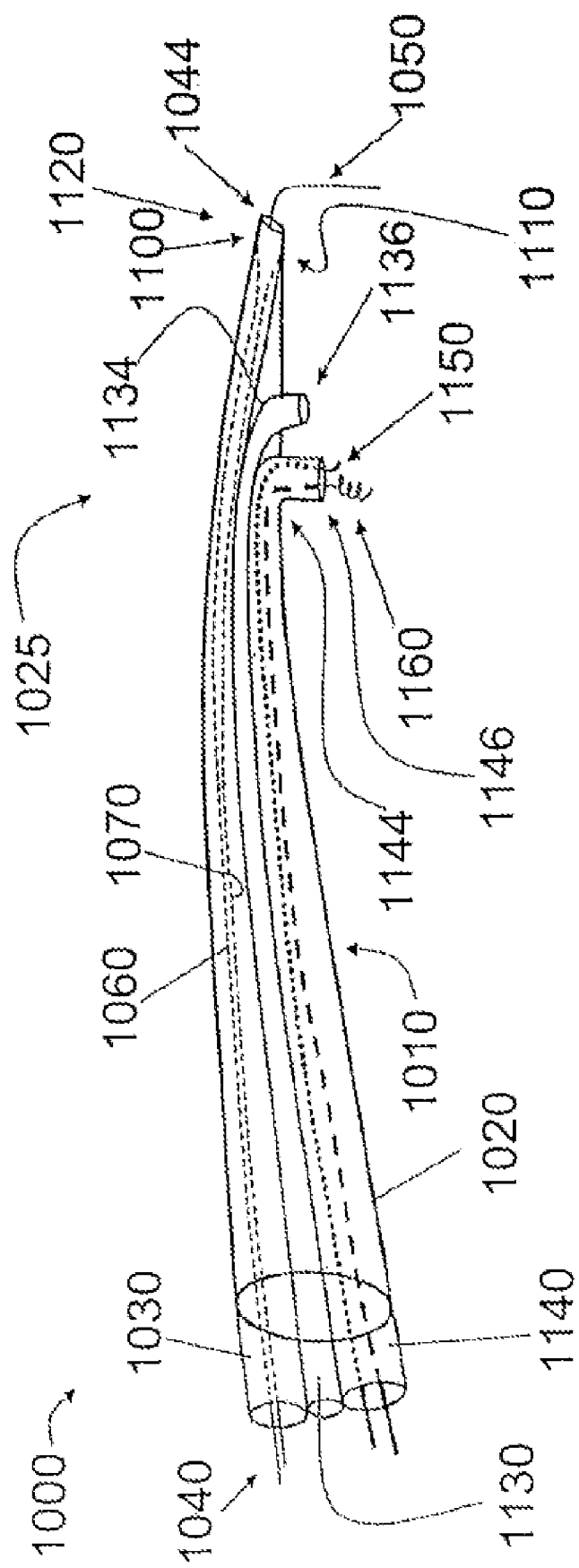
FIG. 7 shows an embodiment of a delivery catheter as disclosed herein.

Referring now to FIG. 7, there is shown a delivery catheter 1000. Delivery catheter 1000 includes an elongated tube 1010 having a wall 1020 extending from a proximal end (not shown) of tube 1010 to a distal end 1025 of tube 1010. Tube 1010 includes two lumens, but other embodiments of delivery catheters may have fewer than, or more than, two lumens, depending on the intended use of the delivery catheter. Tube 1010 also includes a steering channel 1030, in which a portion of steering wire system 1040 is located. Steering channel 1030 forms orifice 1044 at distal end 1025 of tube 1010 and is sized to fit over a guide wire 1050.

Figure 8:
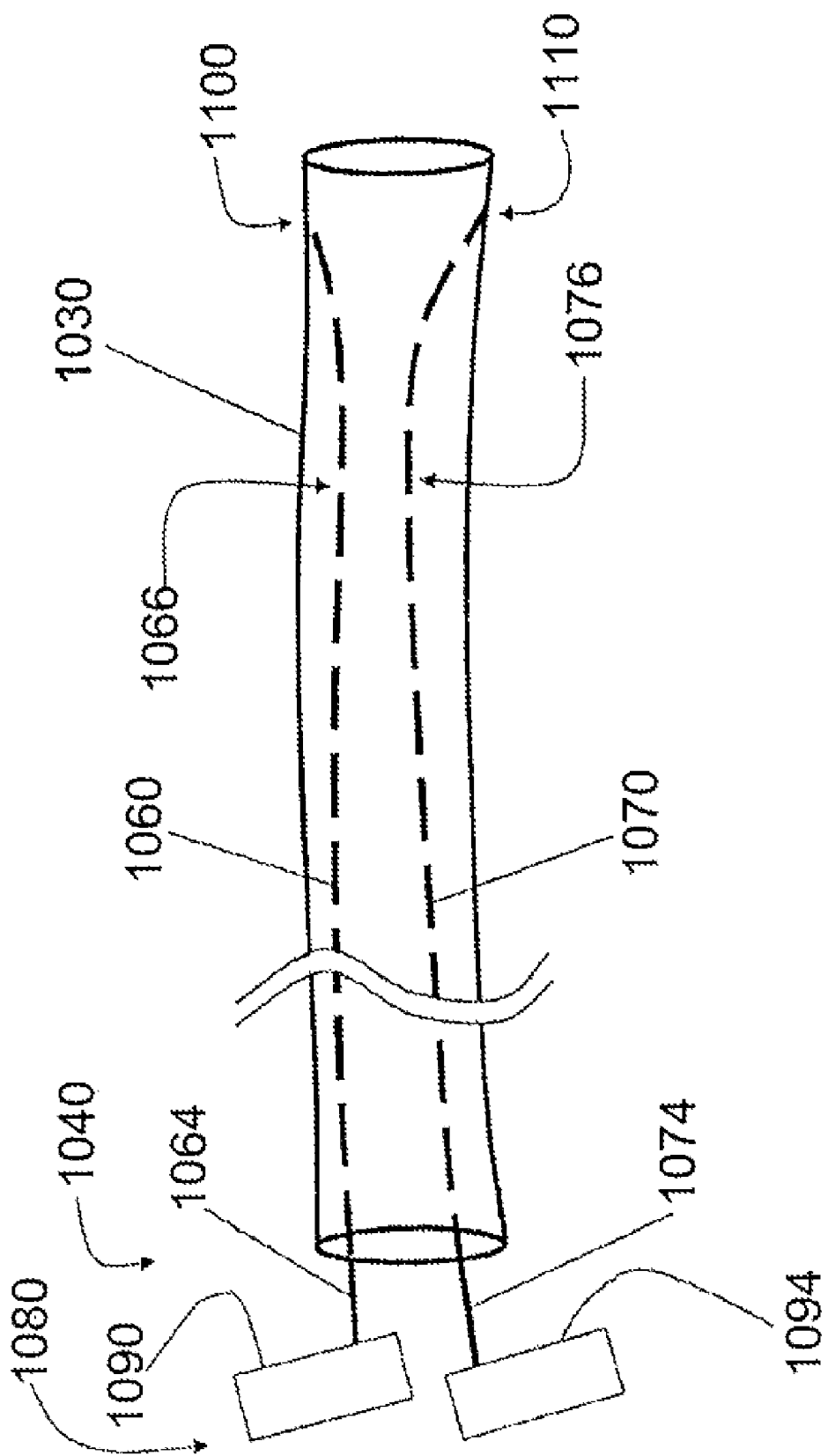
FIG. 8 shows an embodiment of a steering wire system within a steering channel.

FIG. 8 shows in more detail steering wire system 1040 within steering channel 1030 (which is shown cut away from the remainder of the delivery catheter). Steering wire system 1040 is partially located in steering channel 1030 and comprises two steering wires 1060 and 1070 and a controller 1080, which, in the embodiment shown in FIG. 8, comprises a first handle 1090 and a second handle 1094. First handle 1090 is attached to proximal end 1064 of steering wire 1060, and second handle 1094 is attached to proximal end 1074 of steering wire 1070. Distal end 1066 of steering wire 1060 is attached to the wall of the tube of the delivery catheter within steering channel 1030 at attachment 1100, and distal end 1076 of steering wire 1070 is attached to the wall of the tube of the delivery catheter within steering channel 1030 at attachment 1110. As shown in FIG. 7, attachment 1100 and attachment 1110 are located on opposing sides of steering channel 1030 near distal tip 1120 of delivery catheter 1000.

Figure 11:
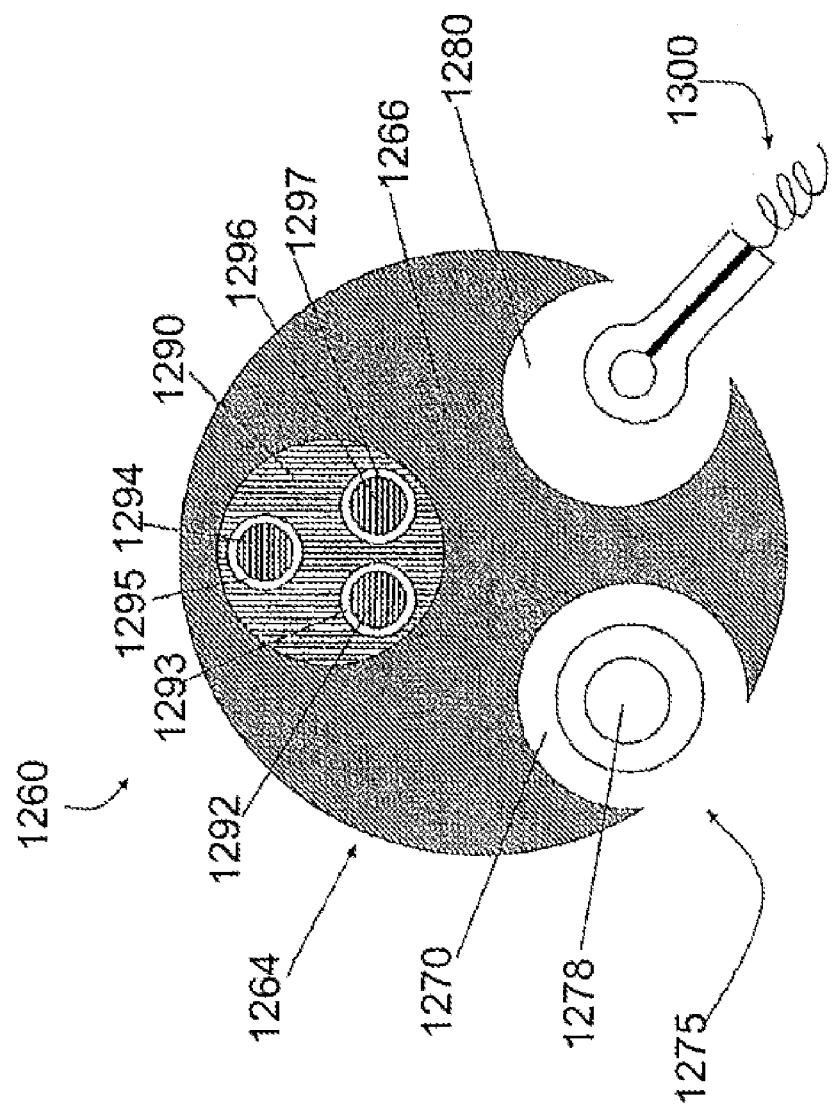
FIG. 11 shows a cross-sectional view of another embodiment of a delivery catheter as disclosed herein.
Figure 12:
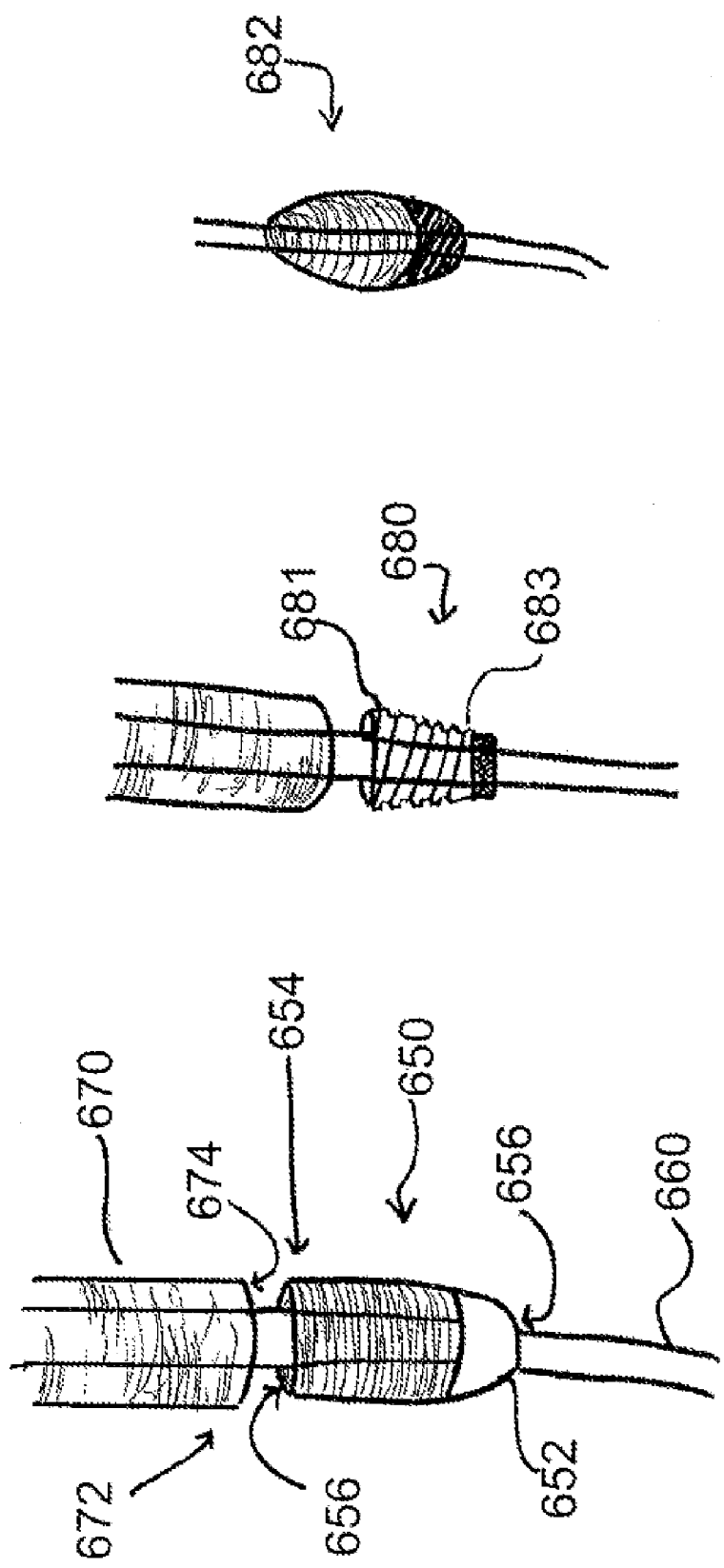
FIG. 12A shows an embodiment of a system for closing a hole in cardiac tissue, as disclosed herein.
FIG. 12B shows another embodiment of a system for closing a hole in cardiac tissue, as disclosed herein.
FIG. 12C shows another embodiment of a system for closing a hole in cardiac tissue, as disclosed herein.

In the embodiment of FIG. 8, steering wires 1060 and 1070 are threaded as a group through steering channel 1030. However, the steering wire systems of other embodiments may include steering wires that are individually threaded through smaller lumens within the steering channel. For example, FIG. 11 shows a cross-sectional view of a delivery catheter 1260 having an elongated tube 1264 comprising a wall 1266, a steering channel 1290, a first lumen 1270, and a second lumen 1280. Delivery catheter 1260 further includes a steering wire 1292 within a steering wire lumen 1293, a steering wire 1294 within a steering wire lumen 1295, and a steering wire 1296 within a steering wire lumen 1297. Each of steering wire lumens 1293, 1295, and 1297 is located within steering channel 1290 and is formed from wall 1266. Each of steering wires 1292, 1294, and 1296 is attached to wall 1266 within steering channel 1290. As will be explained, the attachment of each steering wire to the wall may be located near the distal tip of the delivery catheter, or may be located closer to the middle of the delivery catheter.

Referring now to FIGS. 7 and 8, steering wire system 1040 can be used to control distal tip 1120 of delivery catheter 1000. For example, when first handle 1090 is pulled, steering wire 1060 pulls distal tip 1120, which bends delivery catheter 1000, causing tip deflection in a first direction. Similarly, when second handle 1094 is pulled, steering wire 1070 pulls distal tip 1120 in the opposite direction, which bends delivery catheter 1000, causing tip deflection in the opposite direction. Thus, delivery catheter 1000 can be directed (i.e., steered) through the body using steering wire system 1040.

Although steering wire system 1040 has only two steering wires, other embodiments of steering wire systems may have more than two steering wires. For example, some embodiments of steering wire systems may have three steering wires (see FIG. 11), each of which is attached to the steering channel at a different attachment. Other embodiments of steering wire systems may have four steering wires. Generally, more steering wires give the clinician more control for directing the delivery catheter because each additional steering wire enables the user to deflect the tip of the delivery catheter in an additional direction. For example, four steering wires could be used to direct the delivery catheter in four different directions (e.g., up, down, right, and left).

If a steering wire system includes more than two steering wires, the delivery catheter may be deflected at different points in the same direction. For instance, a delivery catheter with three steering wires may include two steering wires for deflection in a certain direction and a third steering wire for reverse deflection (i.e., deflection in the opposite direction). In such an embodiment, the two steering wires for deflection are attached at different locations along the length of the delivery catheter. Referring now to FIGS. 9A-9C, there is shown a steering wire system 1350 within steering channel 1360 (which is shown cut away from the remainder of the delivery catheter) in different states of deflection. Steering wire system 1350 is partially located in steering channel 1360 and comprises three steering wires 1370, 1380, and 1390 and a controller 1400, which, in the embodiment shown in FIGS. 9A-9C, comprises a handle 1410. Handle 1410 is attached to proximal end 1374 of steering wire 1370, proximal end 1384 of steering wire 1380, and proximal end 1394 of steering wire 1390. Distal end 1376 of steering wire 1370 is attached to the wall of the tube of the delivery catheter within steering channel 1360 at attachment 1378, which is near the distal tip of the delivery catheter (not shown). Distal end 1386 of steering wire 1380 is attached to the wall of the tube of the delivery catheter within steering channel 1360 at attachment 1388, which is near the distal tip of the delivery catheter (not shown). Attachment 1378 and attachment 1388 are located on opposing sides of steering channel 1360 such that steering wires 1370 and 1380, when tightened (as explained below), would tend to deflect the delivery catheter in opposite directions. Distal end 1396 of steering wire 1390 is attached to the wall of the tube of the delivery catheter within steering channel 1360 at attachment 1398, which is located on the delivery catheter at a point closer to the proximal end of the delivery catheter than attachments 1378 and 1388. Attachment 1398 is located on the same side of steering channel 1360 as attachment 1388, such that steering wires 1380 and 1390, when tightened (as explained below), would tend to deflect the delivery catheter in the same direction. However, because attachment 1398 is closer to the proximal end of the delivery catheter than is attachment 1388, the tightening of steering wire 1390 tends to deflect the delivery catheter at a point closer to the proximal end of the delivery catheter than does the tightening of steering wire 1380. Thus, as shown in FIG. 9A, the tightening of steering wire 1390 causes a deflection in the delivery catheter approximately at point 1410. The tightening of steering wire 1380 at the same time causes a further deflection in the delivery catheter approximately at point 1420, as shown in FIG. 9B. The tightening of steering wire 1370, therefore, causes a reverse deflection, returning the delivery catheter to its original position (see FIG. 9C).

Referring again to FIG. 7, elongated tube 1010 further includes lumen 1130 and lumen 1140. Lumen 1130 extends from approximately the proximal end (not shown) of tube 1010 to or near distal end 1025 of tube 1010. Lumen 1130 has a bend 1134, relative to tube 1010, at or near distal end 1025 of tube 1010 and an outlet 1136 through wall 1020 of tube 1010 at or near distal end 1025 of tube 1010. Similarly, lumen 1140 has a bend 1144, relative to tube 1010, at or near distal end 1025 of tube 1010 and an outlet 1146 through wall 1020 of tube 1010 at or near distal end 1025 of tube 1010. In the embodiment shown in FIG. 7, lumen 1130 is configured as a laser Doppler tip, and lumen 1140 is sized to accept a retractable sensing lead 1150 and a pacing lead 1160 having a tip at the distal end of the lead. The fiberoptic laser Doppler tip detects and measures blood flow (by measuring the change in wavelength of light emitted by the tip), which helps the clinician to identify—and then avoid—blood vessels during lead placement. Sensing lead 1150 is designed to detect electrical signals in the heart tissue so that the clinician can avoid placing a pacing lead into electrically nonresponsive tissue, such as scar tissue. Pacing lead 1160 is a screw-type lead for placement onto the cardiac tissue, and its tip, which is an electrode, has a substantially screw-like shape. Pacing lead 1160 is capable of operative attachment to a CRT device (not shown) for heart pacing. Although lead 1160 is used for cardiac pacing, any suitable types of leads may be used with the delivery catheters described herein, including sensing leads.

Each of bend 1134 of lumen 1130 and bend 1144 of lumen 1140 forms an approximately 90-degree angle, which allows respective outlets 1136 and 1146 to face the external surface of the heart as the catheter is maneuvered in the pericardial space. However, other embodiments may have bends forming other angles, smaller or larger than 90-degrees, so long as the lumen provides proper access to the external surface of the heart from the pericardial space. Such angles may range, for example, from about 25-degrees to about 155-degrees. In addition to delivering leads and Doppler tips, lumen 1130 and lumen 1140 may be configured to allow, for example, the taking of a cardiac biopsy, the delivery of gene cell treatment or pharmacological agents, the delivery of biological glue for ventricular reinforcement, implementation of ventricular epicardial suction in the acute myocardial infarction and border zone area, the removal of fluid in treatment of pericardial effusion or cardiac tamponade, or the ablation of cardiac tissue in treatment of atrial fibrillation.

For example, lumen 1130 could be used to deliver a catheter needle for intramyocardial injection of gene cells, stems, biomaterials, growth factors (such as cytokinase, fibroblast growth factor, or vascular endothelial growth factor) and/or biodegradable synthetic polymers, RGD-liposome biologic glue, or any other suitable drug or substance for treatment or diagnosis. For example, suitable biodegradable synthetic polymer may include polylactides, polyglycolides, polycaprolactones, polyanhydrides, polyamides, and polyurethanes. In certain embodiments, the substance comprises a tissue inhibitor, such as a metalloproteinase (e.g., metalloproteinase 1).

The injection of certain substances (such as biopolymers and RGD-liposome biologic glue) is useful in the treatment of chronic heart failure to reinforce and strengthen the left ventricular wall. Thus, using the embodiments disclosed herein, the injection of such substances into the cardiac tissue from the pericardial space alleviates the problems and risks associated with delivery via the transthoracic approach. For instance, once the distal end of the delivery catheter is advanced to the pericardial space, as disclosed herein, a needle is extended through a lumen of the delivery catheter into the cardiac tissue and the substance is injected through the needle into the cardiac tissue.

The delivery of substances into the cardiac tissue from the pericardial space can be facilitated using a laser Doppler tip. For example, when treating ventricular wall thinning, the laser Doppler tip located in lumen 1140 of the embodiment shown in FIG. 7 can be used to measure the thickness of the left ventricular wall during the procedure (in real time) to determine the appropriate target area for injection.

Figure 10:
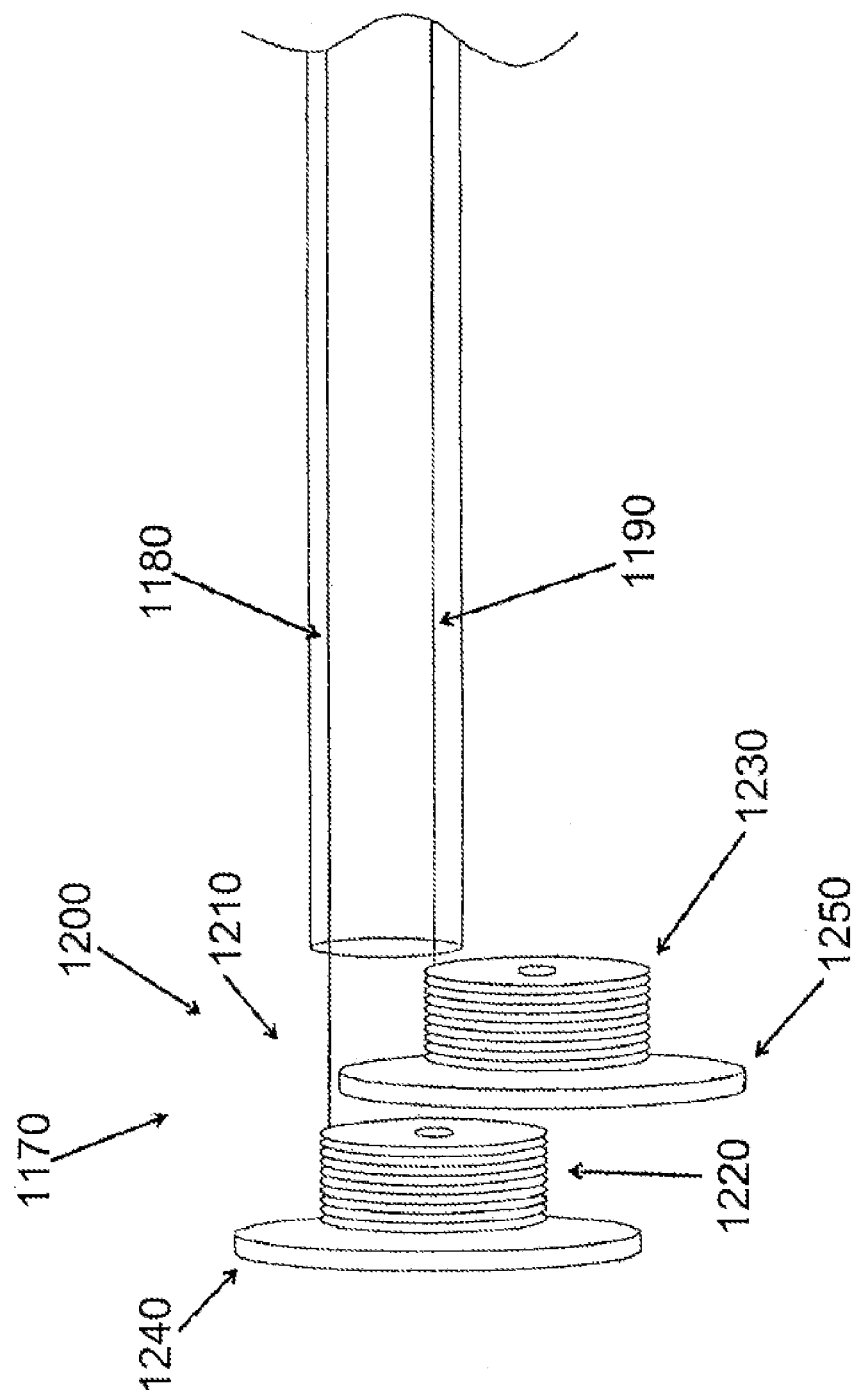
FIG. 10 shows a portion of another embodiment of a steering wire system.

Referring again to FIG. 8, although controller 1080 comprises first handle 1090 and second handle 1094, other embodiments of the controller may include different configurations. For example, instead of using handles, a controller may include any suitable torque system for controlling the steering wires of the steering wire system. Referring now to FIG. 10, there is shown a portion of a steering wire system 1170 having steering wire 1180, steering wire 1190, and controller 1200. Controller 1200 comprises a torque system 1210 having a first rotatable spool 1220, which is capable of collecting and dispensing steering wire 1180 upon rotation. For example, when first rotatable spool 1220 rotates in a certain direction, steering wire 1180 is collected onto spool 1220, thereby tightening steering wire 1180. When spool 1220 rotates in the opposite direction, steering wire 1180 is dispensed from spool 1220, thereby loosening steering wire 1180. Torque system 1210 also has a second rotatable spool 1230, which is capable of collecting and dispensing steering wire 1190 upon rotation, as described above.

Torque system 1210 further includes a first rotatable dial 1240 and a second rotatable dial 1250. First rotatable dial 1240 is attached to first rotatable spool 1220 such that rotation of first rotatable dial 1240 causes rotation of first rotatable spool 1220. Similarly, second rotatable dial 1250 is attached to second rotatable spool 1230 such that rotation of second rotatable dial 1250 causes rotation of second rotatable spool 1230. For ease of manipulation of the catheter, torque system 1210, and specifically first and second rotatable dials 1240 and 1250, may optionally be positioned on a catheter handle (not shown) at the proximal end of tube 1010.

Steering wire system 1170 can be used to direct a delivery catheter through the body in a similar fashion as steering wire system 1140. Thus, for example, when first rotatable dial 1240 is rotated in a first direction (e.g., clockwise), steering wire 1180 is tightened and the delivery catheter is deflected in a certain direction. When first rotatable dial 1240 is rotated in the other direction (e.g., counterclockwise), steering wire 1180 is loosened and the delivery catheter straightens to its original position. When second rotatable dial 1250 is rotated in one direction (e.g., counterclockwise), steering wire 1190 is tightened and the delivery catheter is deflected in a direction opposite of the first deflection. When second rotatable dial 1250 is rotated in the other direction (e.g., clockwise), steering wire 1190 is loosened and the delivery catheter is straightened to its original position.

Certain other embodiments of steering wire system may comprise other types of torque systems, so long as the torque system permits the clinician to reliably tighten and loosen the various steering wires. The magnitude of tightening and loosening of each steering wire should be controllable by the torque system.

Figure 23:
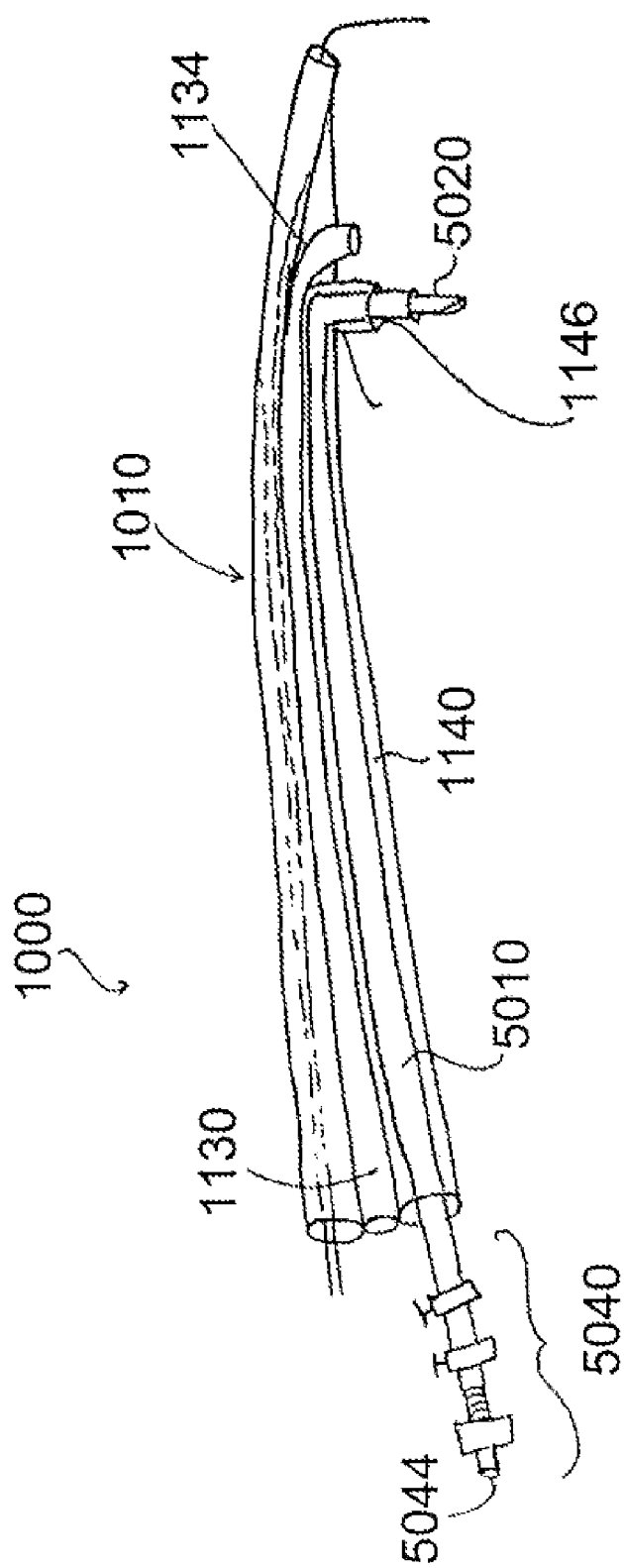
FIG. 23 shows an embodiment of a delivery catheter as disclosed herein comprising a biopsy system.

In one application, the delivery catheter 1000 can be used in conjunction with a biopsy system to obtain a sample of tissue from the surface of the heart. Now referring to FIG. 23, one embodiment of a biopsy system 5000 is shown positioned within the lumen 1140 of the delivery catheter 1000. The biopsy system 5000 (shown in detail in FIG. 24) is configured to extend through the lumen 1140 from approximately the proximal end (not shown) of the tube 1010 to at or near the distal end 1025 of the tube 1010. It will also be understood that the biopsy system 5000 may be alternatively disposed within the lumen 1130.

Figure 24:
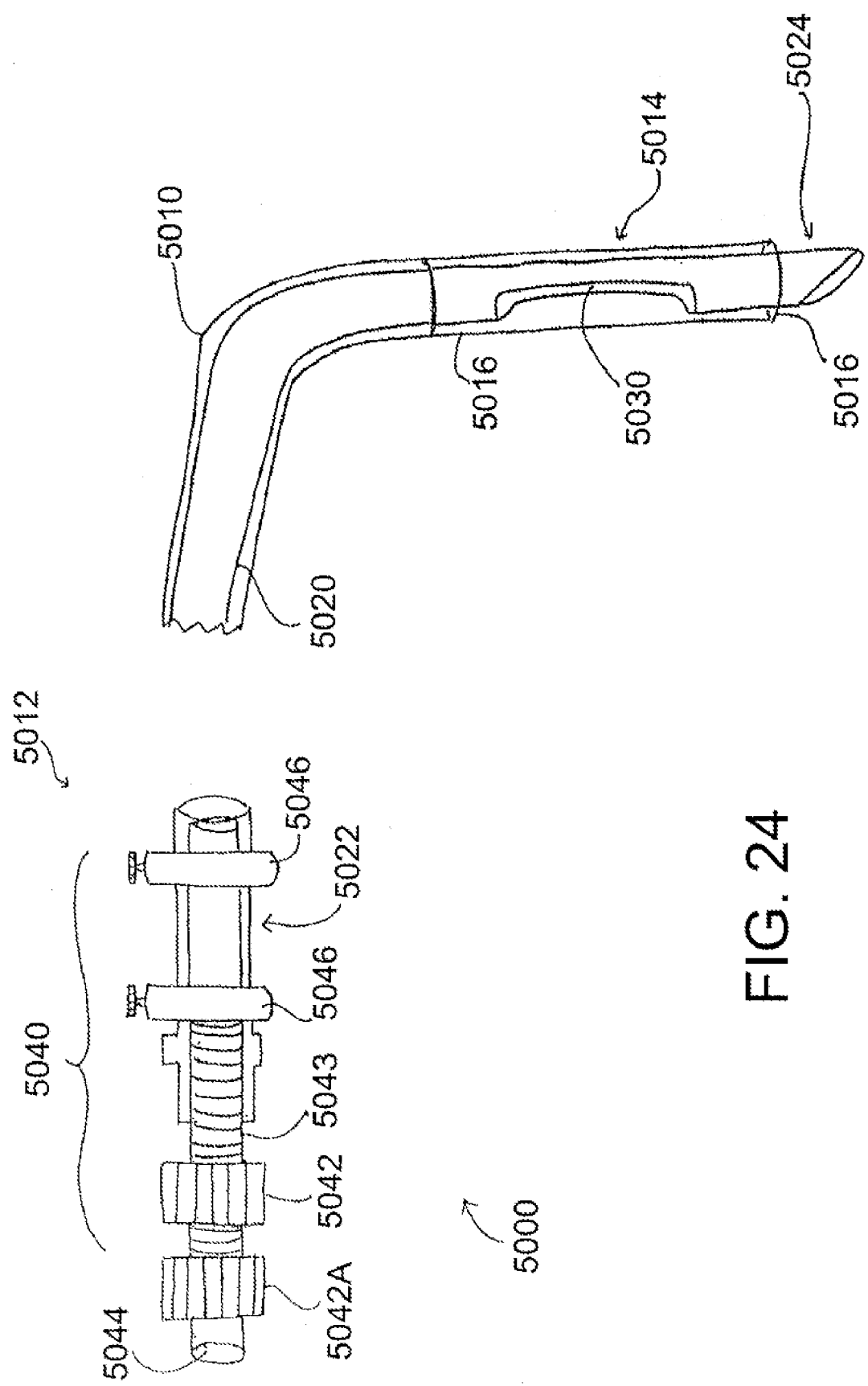
FIG. 24 shows an embodiment of the proximal and distal ends of the biopsy system shown in FIG. 23.
Figure 25:
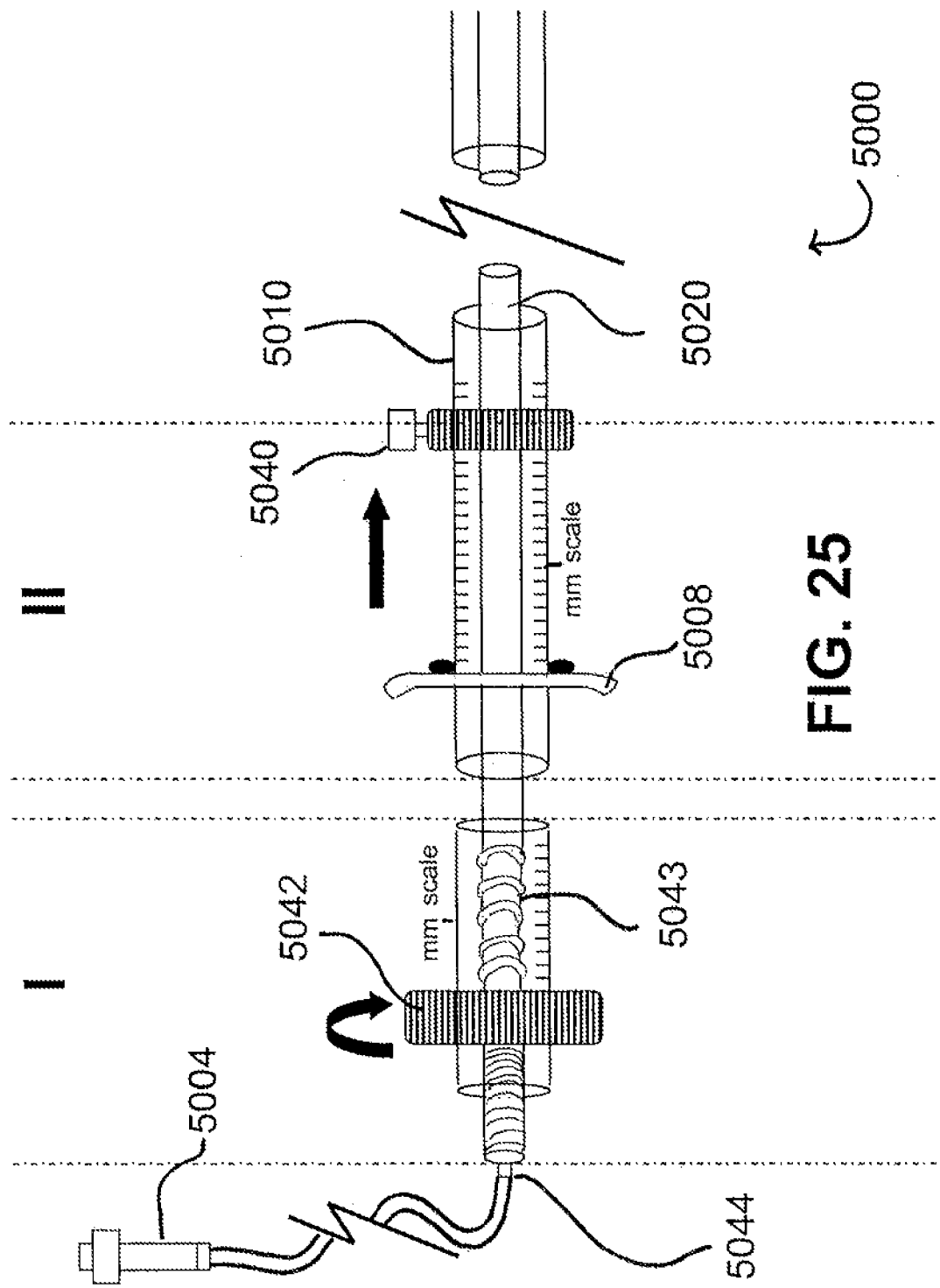
FIG. 25 shows an embodiment of the proximal end of the biopsy system of FIG. 23.

Now referring to FIGS. 24 and 25, one embodiment of the biopsy system 5000 comprises two semi-rigid catheters, with the second catheter 5020 disposed within the interior of the first catheter 5010. Both the first catheter 5010 and the second catheter 5020 are configured to conform to the bend 1144 of the lumen 1140 (or the bend 1134 of the lumen 1130, if applicable) as shown in FIG. 24. In this manner, the first catheter 5010 and the second catheter 5020 can engage the tissue in an operative way when advanced through the outlet 1146 of the lumen 1140.

The first catheter 5010 comprises a proximal end 5012, a distal end 5014, and a hollow interior. The proximal end 5012 of the first catheter 5010 is coupled with a torque mechanism 5040 (described below), a vacuum source 5004 and, optionally, a handle 5008 (see FIG. 25). The handle 5008 may be configured in any fashion and, in at least one embodiment, may assist a user to hold the delivery catheter 1000 during the operation thereof. The distal end 5014 of the first catheter 5010 is open and further comprises at least one sharp cutting edge 5016 capable of cutting tissue. The distal end 5014 of the first catheter 5010 may be used for aspiration or to cut the tissue targeted for the biopsy (the "targeted tissue") through use of the sharp cutting edges 5016. In one embodiment, the sharp cutting edge 5016 comprises a hollow, metallic cylinder disposed on the distal end 5014 of the first catheter 5010. In addition, the configuration of the distal end 5014 of the first catheter 5010 is such that, when a suctional force is supplied by the vacuum source 5004 within the interior of the first catheter 5010, the distal end 5014 of the first catheter 5010 can be used to provide suction to the targeted tissue.

The second catheter 5020 of the biopsy system 5000 comprises a hollow interior, a proximal end 5022, and a distal end 5024, and may be used to aspirate and puncture the targeted tissue site. Further, the second catheter 5020 is configured to be slidably movable through the hollow interior of the first catheter 5010 such that the second catheter 5020 can advance through the open distal end 5014 of the first catheter 5010. As shown in FIGS. 24 and 25, the proximal end 5022 of the second catheter 5020 is coupled with the torque mechanism 5040 and a vacuum source 5004, and the distal end 5024 of the second catheter 5020 is open. In at least one embodiment, the distal end 5024 of the second catheter 5020 may further comprise an angled configuration or comprise a needle to facilitate the advancement of the distal end 5024 of the second catheter 5020 through the targeted tissue. Further, at or near the distal end 5024 of the second catheter 5020, the second catheter 5020 comprises an opening 5030 for accepting the tissue sample on which the biopsy will be performed. In at least one embodiment, the opening 5030 is curved-shaped, positioned on the lateral surface of the second catheter 5020, and in communication with the hollow interior of the second catheter 5020. Accordingly, when a vacuum source such as a syringe or vacuum pump is coupled with the proximal end 5022 of the second catheter 5020, a vacuum is created within the interior of the second catheter 5020, and the second catheter 5020 may be used to aspirate the targeted tissue through the open distal end 5024, collect the tissue sample through the opening 5030, and/or, by use of the suctional force within the interior of the second catheter 5020, retrieve the tissue sample from the body through the interior of the second catheter 5020. It will be understood that the vacuum source 5004 coupled with the proximal end 5022 of the second catheter 5020 may also be coupled with the proximal end 5012 of the first catheter 5010. Alternatively, at least two vacuum sources 5004 may be employed in conjunction with the biopsy system 5000 such that each catheter 5010, 5020 is coupled with an independent vacuum source. In the latter embodiment, the suctional force within the interior of the first catheter 5010 may be regulated and maintained independently of the suctional force within the interior of the second catheter 5020, thereby providing a clinician with more control over the operation of the biopsy system 5000.

As previously indicated, the proximal end 5012 of the first catheter 5010 and the proximal end 5022 of the second catheter 5020 are coupled with a torque mechanism 5040. The torque mechanism 5040 comprises at least one rotatable dial 5042, at least one shaft 5043, and a suction port 5044. The suction port 5044 is in communication with the interior of the second catheter 5020 and configured to be coupled with a vacuum source 5004. In this manner, when a vacuum source is applied to the suction port 5044, a vacuum is formed within the interior of the second catheter 5020 and a suctional force is exerted through the opening 5030 in the distal end 5024 of the second catheter 5020 and through the open end of the distal end 5024 of the second catheter 5020.

Each of the at least one rotatable dials 5042 is coupled with a shaft 5043 and, in at least one embodiment, the axis of the rotatable dial 5042 is concentric to the axis of the shaft 5043. The rotatable dial 5042 is configured such that the rotatable dial 5042 is capable of rotational movement around the shaft 5043. Each of the at least one shafts 5043 comprises a proximal end and a distal end and may comprise any configuration so long as the shaft 5043 is capable of converting the rotational movement of the rotatable dial 5042 into incremental linear movement. For example, in one embodiment, each of the at least one shafts 5043 may comprise a leadscrew as is known in the art.

The distal end of the shaft 5043 is coupled with the proximal end 5012 of the first catheter 5010, the proximal end 5022 of the second catheter 5020, or both. In one embodiment, a first shaft 5043 is coupled with the second catheter 5020 such that when the rotatable dial 5042 is rotated in a first direction (e.g., clockwise), the second catheter 5020 is advanced relative to the first catheter 5010 and the lumen 1140 of the delivery catheter 1000. Further, when the rotatable dial 5042 is rotated in a second direction (e.g., counterclockwise), the second catheter 5020 retracts relative to the first catheter 5010 and the lumen 1140. In at least one embodiment, a second shaft 5043 may be coupled with the first catheter 5010 such that when the rotatable dial 5042 is rotated in a first direction, the first catheter 5010 is advanced relative to the second catheter 5020 and the lumen 1140 and when the rotatable dial 5042 is rotated in a second direction, the first catheter 5010 retracts relative to the second catheter 5020 and the lumen 1140.

It will be understood that any number of rotatable dials 5042 and corresponding shafts 5043 may be used in various combinations to facilitate the independent movement of the first catheter 5010 relative to the second catheter 5020, and vice versa. In this manner, the biopsy system 5000 provides a user with the ability to easily and independently control the placement of the first and second catheters 5010, 5020 when the biopsy system 5000 is in use. For example, in the embodiment shown in FIG. 24, the torque mechanism 5040 comprises a first rotatable dial 5042 and a second rotatable dial 5042A. As previously described, the first rotatable dial 5042 is coupled with the first catheter 5010 through a corresponding shaft 5043 and the second rotatable dial 5042A is coupled the second catheter 5020 through a separate shaft (not shown). In this embodiment, rotation of the first rotatable dial 5042 causes the first catheter 5010 to either advance or retract and, similarly, rotation of the second rotatable dial 5042A causes the second catheter 5020 to either advance or retract. Accordingly, a clinician can independently control the distal ends 5012, 5022 of the catheters 5010, 5020 from an external location when the biopsy system 5000 is used to collect a targeted tissue from a patient.

Certain other embodiments of the torque mechanism 5040 may comprise other types of torque systems, so long as the torque system permits the clinician to reliably advance and retract the components of the biopsy system 5000. Further, the magnitude of the advancement and retraction of the components should be controllable by the torque system as described below.

In at least one embodiment, a defined rotation of the rotatable dial 5042 (e.g., one full rotation) corresponds to a particular increment that the first or second catheter 5010, 5020 is advanced or retracted. For example, in one embodiment, one complete clockwise turn of the rotatable device advances the second catheter 5020 1 mm. The rotation of the rotatable dial 5042 may further be segmented in defined increments such that a user can advance or retract the applicable catheter 5010, 5020 a defined distance without performing a complete rotation of the rotatable dial 5042. Further, the torque mechanism 5040 can be calibrated by a user to define a specific degree of rotation of the rotatable dial 5042 to a precise distance of linear movement. For example, for applications that require a high degree of precision, a user can set the shaft 5043 to advance/retract the applicable catheter 5010, 5020 in increments of 0.5 mm per 10 degrees of rotation of the rotatable dial 5042. Alternatively, for applications that require less specificity—such as performing a biopsy for an autopsy—a user can set the shaft 5043 to advance/retract the applicable catheter 5010, 5020 in increments of 1.5 mm per 10 degrees of rotation of the rotatable dial 5042. Accordingly, a user can program the torque mechanism 5040 for a specific application or procedure.

The torque mechanism 5040 may further comprise at least one limiter 5046, which is operatively coupled with the proximal ends 5012, 5022 of the first and second catheters 5010, 5020. In the embodiment shown in FIG. 24, the torque mechanism 5040 comprises two limiters 5046. The limiter 5046 may be any mechanism capable of preventing the overextension of the applicable catheter 5010, 5020. For example, a clinician can set the limiter 5046 to prevent the second catheter 5020 from advancing more than 8 mm. In this manner, the limiter 5046 functions as a safety mechanism to prevent the over-penetration of the tissue from which a biopsy is to be obtained. Any number of limiters 5046 may be used in conjunction with the torque mechanism 5040 and, in one embodiment, a first limiter 5046 is applied to the first catheter 5010 and a second limiter 5046 is applied to the second catheter 5020. In this embodiment, the first and second limiters 5046 may be independently set by the clinician.

Obtaining a tissue specimen for a biopsy may be accomplished using the biopsy system 5000. A typical procedure would involve the percutaneous intravascular insertion of a portion of the delivery catheter 1000 into a body, which can be performed as previously described herein under local or general anesthesia. In one embodiment, the biopsy system 5000 is coupled with the delivery catheter 1000, the first and second catheters 5010, 5020 are positioned within the lumen 1140, and a fiberoptic laser Doppler tip positioned within the lumen 1130. A portion of the delivery catheter 1000 may then utilize an approach described herein or otherwise known by a user of the delivery catheter 1000 to enter the percutaneous intravascular pericardial sac. It can be appreciated that the delivery catheter 1000 may be used in conjunction with the biopsy system 5000 to access other spaces within a body to obtain a tissue specimen therefrom, and that such an apparatus is not limited to heart access and removal of myocardial tissue. In one embodiment, the biopsy system 5000 is coupled with the delivery catheter 1000 such that when the delivery catheter 1000 is used to deliver the distal ends 5014, 5024 of the first and second catheters 5010, 5020 to a targeted tissue, the torque mechanism 5040 (and in some embodiments, the handle 5008) is positioned externally of the patient's body, thereby providing a clinician with control over the operation of the biopsy system 5000. In addition, embodiments of the delivery catheter 1000 may also facilitate the delivery of other mechanisms to a targeted tissue in addition to the biopsy system 5000. For example and without limitation, referring back to FIG. 11, there is shown a cross-sectional view of a delivery catheter 1260. Delivery catheter 1260 includes tube 1265, a first lumen 1270, a second lumen 1280, and a steering channel 1290. Steering wires 1292, 1294, and 1296 are shown within steering channel 1290. First lumen 1270 has outlet 1275, which can be used to deliver a micro-camera system (not shown) or a laser Doppler tip 1278. Second lumen 1280 is sized to deliver a pacing lead 1300, as well as a sensing lead (not shown). Accordingly, embodiments of the delivery catheter 1000 may enable a clinician to employ steering wires 1292, 1294 and 1296, a navigational tool such as a micro-camera system, a laser Doppler tip or otherwise, or any number of other devices in conjunction with the biopsy system 5000.

A procedure using the biopsy system 5000 may be performed by inserting the delivery catheter 1000 into a pericardial sac, following the cardiac surface using, for example, fluoroscopy and/or echodoppler visualization techniques. In one embodiment, obtaining a tissue specimen for biopsy can be facilitated using a laser Doppler tip. For example, when locating the targeted tissue on the surface of the heart from which to collect a tissue sample, the laser Doppler tip located in the lumen 1130 can be used to measure the thickness of the epicardial wall and/or identify any vasculature located thereon to determine the appropriate target area for obtaining the tissue specimen. In this manner, the laser Doppler tip can be used to avoid over-penetration of the myocardial tissue and damaging surrounding vascular structures. It will be appreciated that other types of visualization tools may be used in conjunction with the biopsy system 5000 and the delivery catheter 1000. For example, an endo-camera or a micro-camera may be located in the lumen 1130 and used for navigation and/or location of the targeted tissue.

After the targeted tissue has been identified, the vacuum source 5004 (e.g., a syringe or vacuum pump) is used to apply suction through the distal end 5014 of the first catheter 5010. Initially, the first and second catheters 5010, 5020 are positioned such that the first catheter 5010 contains the distal end 5024 of the second catheter 5020, as shown in FIG. 26A. Accordingly, the suction may be achieved by operation of the vacuum source 5004 coupled with the proximal end 5012 of the first catheter 5010. In another embodiment, suction may be achieved by operation of the vacuum source 5004 coupled with the proximal end 5022 of the second catheter 5020. In this embodiment, the suctional force within the interior of the second catheter 5020 is communicated into the interior of the first catheter 5010 such that suction is applied through the open distal end 5014 of the first catheter 5010. In this manner, the distal end 5014 of the first catheter 5010 aspirates and removably engages the surface of the targeted tissue such that a reversible seal is formed therebetween. In yet another embodiment, suction may be applied through the interiors of both the first and second catheters 5010, 5020, either by operation of one vacuum source 5004 coupled with both the first and second catheters 5010, 5020, or through operation of at least two vacuum sources 5004, each vacuum source 5004 being independently coupled with either the first or second catheter 5010, 5020. Irrespective of to which catheter 5010, 5020 the vacuum source(s) 5004 is/are coupled, suction is maintained within the distal end 5014 of the first catheter 5010 throughout the biopsy procedure. This enables the first catheter 5010 to remain removably engaged with the targeted tissue throughout the biopsy procedure, thereby assisting to stabilize the biopsy system 5000, ensuring that the tissue sample is being collected from the identified targeted tissue, and preventing the collected tissue from becoming contaminated.

After the first catheter 5010 has engaged the surface of the targeted tissue, the clinician uses the torque mechanism 5040 to advance the distal end 5024 of the second catheter 5020 into the targeted tissue. As previously described, the clinician controls how deep the second catheter 5020 penetrates the tissue by using the calibrated torque mechanism 5040. As shown in FIG. 26B, the distal end 5024 of the second catheter 5020 is advanced into the targeted tissue far enough that the opening 5030 is positioned within the tissue. After the distal end 5024 of the second catheter 5020 is positioned at the desired depth within the tissue, the torque mechanism 5040 is used to advance the cutting portion 5016 of the first catheter 5010 over the extended second catheter 5020 and into the targeted tissue. The first catheter 5010 may be advanced to the same depth as the second catheter 5020 such that the distal end 5014 of the first catheter 5010 and the distal end 5024 of the second catheter 5020 are even with one another. In this manner, the first catheter 5010 carves out a groove in the targeted tissue, thereby entrapping a portion of the tissue within the interior of the first catheter 5010. As the distal end 5014 of the first catheter 5010 comprises a cylindrical configuration, the tissue contained within the interior of the first catheter 5010 is detached from the targeted tissue. It will be understood that the amount of the tissue contained within the interior of the first catheter 5010 corresponds with the diameter of the first catheter 5010, and this diameter may be selected depending on the amount of tissue sample desired. For example, in one embodiment, the diameter of the first catheter 5010 may be 1 mm.

As shown in FIG. 26C, after the tissue sample is entrapped within the interior of the first catheter 5010, suction is again applied (or increased) through the interior of the second catheter 5020, which results in a suctional force through the opening 5030. The clinician can increase the strength of the suction within the interior of the second catheter 5020 as needed to pull the detached tissue into the interior of the second catheter 5020 and retain the tissue therein. After the detached tissue is positioned within the interior of the second catheter 5020, the suction within the interior of the first catheter 5010 is decreased, thereby releasing the seal between the distal end 5014 of the first catheter 5010 and the targeted tissue. Thereafter, both the first and second catheters 5010, 5020 are withdrawn from the targeted tissue, thereby removing the tissue sample that is contained within the interior of the second catheter 5020 (see FIG. 26D). During the removal of the catheters 5010, 5020 from the body, the clinician can optionally increase or maintain the suction within the interior of the second catheter 5020 to ensure that the tissue sample is retained therein.

Figure 27B:
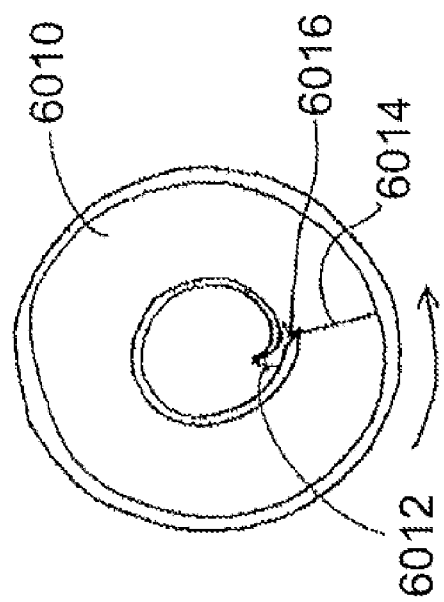
FIG. 27B shows a bottom view of the component of FIG. 27A.
Figure 27A:
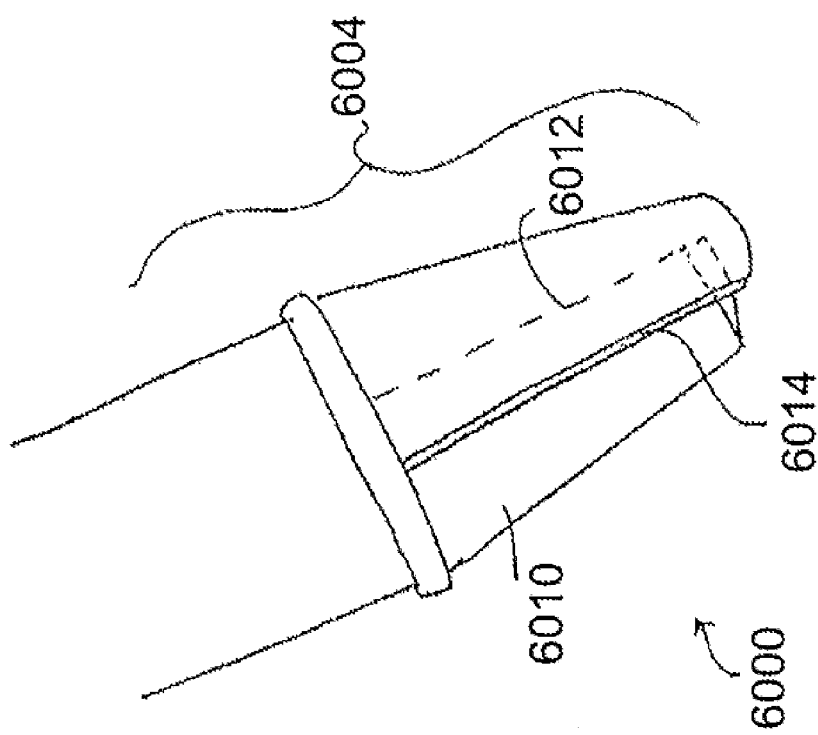
FIG. 27A shows a side view of an embodiment of the distal end of a component of a biopsy system.

Now referring to FIGS. 27A and 27B, an alternative embodiment of the first and second catheters 5010, 5020 is shown. In this embodiment, a single catheter 6000 is used in conjunction with the biopsy system 5000 to obtain a tissue sample from a targeted tissue. The catheter 6000 comprises a semi-rigid catheter configured to conform to the bend 1114 of the lumen 1140 (or the bend 1134 of the lumen 1130, if applicable). In this manner, the catheter 6000 can engage the targeted tissue in an operative way when advanced through the outlet 1146 of the lumen 1140.

The catheter 6000 comprises a proximal end 6002 (not shown), a distal end 6004, and a hollow interior. The proximal end 6002 is configured to couple with the torque mechanism 5040 and a vacuum source (not shown), such that a clinician can advance and retract the catheter 6000 as previously described with respect to the first and second catheters 5010, 5020, and a suctional force can be produced within the interior of the catheter 6000. However, in this embodiment, the torque mechanism 5040 may further comprise a component to allow a clinician to rotate the catheter 6000 within the lumen 1140. For example and without limitation, the torque mechanism 5040 may comprise at least one dial affixed to a shaft such that rotation of the dial translates to rotation of the shaft and thus the catheter 6000.

The distal end 6004 of the catheter 6000 is open and comprises a cutting portion 6010 configured in a conical shape. In at least one embodiment, the apex of the conical cutting portion 6010 is positioned distally of the base, such that the cutting portion 6010 tapers in and is narrower at its distal end. Accordingly, when the distal end 6004 of the catheter 6000 is applied to a targeted tissue, the conical configuration and narrow distal end of the cutting portion 6010 enables the distal end 6004 of the catheter 6000 to easily puncture and be inserted into the targeted tissue.

The cutting portion 6010 further comprises overlapping edges. In one embodiment, the cutting portion 6010 comprises a first edge 6012 and a second edge 6014 and may comprise a metallic material or any other material capable of cutting tissue. As shown in FIGS. 27A and 2713, the cutting portion 6010 is configured such that the first edge 6012 is folded underneath the second edge 6014 and the first and second edges 6012, 6014 overlap. Further, an opening 6016 is formed between the first and second edges 6012, 6014 such that tissue can move therethrough. In this embodiment, the second edge 6014 extends the length of the cutting portion 6010 and comprises a sharp, cutting edge that is capable of cutting tissue.

Similar to the first and second catheters 5010, 5020, the catheter 6000 may be used to collect a tissue sample from a targeted tissue. In this embodiment, the catheter 6000 is positioned within the lumen 1140 of the delivery catheter 1000 and coupled with the torque mechanism 5040 and a vacuum source as previously described. After the laser Doppler system has identified the targeted tissue, the distal end 6004 of the catheter 6000 is advanced and engages the surface of the targeted tissue. Suction may be applied through the interior of the catheter 6000 such that the open distal end 6004 of the catheter 6000 aspirates the targeted tissue.

After the catheter 6000 has engaged the surface of the targeted tissue, the clinician uses the torque mechanism 5040 to advance the distal end 6004 into the targeted tissue to a particular depth. Thereafter, the clinician, either manually or using the torque mechanism 5040, rotates the catheter 6000 in the direction of the second edge 6014 (see FIG. 27B). Due to the overlapping configuration of the first and second edges 6012, 6014, the rotational movement of the catheter 6000 causes the second edge 6014 to slice the targeted tissue and draw the tissue sample through the opening 6016 and into the interior of the catheter 6000. Suction can also be applied through the interior of the catheter 6000 to facilitate the ease of the cutting process and retention of the tissue sample within the interior of the catheter 6000.

After the distal end 6004 of the catheter 6000 has made a complete rotation and detached the tissue sample from the surrounding lateral portion of the targeted tissue, the catheter 6000 is withdrawn through the delivery catheter 1000, thereby removing the tissue sample contained therein. The tapered configuration of the cutting portion 6010 allows the catheter 6000 to be easily dislodged from the targeted tissue, as only a narrow portion of the tissue has not been subjected to the cutting edge 6014.

In addition to retrieving a biological tissue sample for biopsy, the devices, systems and methods disclosed herein can be used for therapeutic treatments. Treatment of cardiac tamponade by the removal of a pericardial effusion may be accomplished using an apparatus of the present disclosure as described below. A typical procedure would involve the percutaneous intravascular insertion of a portion of an apparatus into a body, which can be performed under local or general anesthesia. A portion of the apparatus may then utilize an approach described herein or otherwise known by a user of the apparatus to enter the percutaneous intravascular pericardial sac. It can be appreciated that such an apparatus may be used to access other spaces within a body to remove fluid and/or deliver a gas, liquid, and/or particulate(s) as described herein, and that such an apparatus is not limited to heart access and removal of pericardial effusions.

Exemplary embodiments of a portion of such an apparatus are shown in FIGS. 21A and 21B. As shown in FIG. 21A, a perforated drainage catheter 2100 is provided. Perforated drainage catheter 2100 comprises a tube defining at least one suction/injection aperture 2110, and as shown in the embodiment in FIG. 21A, perforated drainage catheter 2100 defines multiple suction/injection apertures 2110. Suction/injection apertures 2110 are operably connected to an internal lumen defined within perforated delivery catheter 2100. It can be appreciated that the portion of perforated drainage catheter 2100 as shown in FIGS. 21A and 21B may be coupled to one or more portions of a system for engaging a tissue as described herein. As such, one or more portions of a system for engaging a tissue may be used to define a system for removing fluid as described herein.

It can be appreciated that the internal lumen within perforated delivery catheter 2100 may define multiple internal channels. For example, perforated delivery catheter 2100 may define two channels, one channel operably coupled to one or more suction/injection apertures 2110 to allow for a vacuum source coupled to one end of the channel to provide suction via the suction/injection apertures 2110, and one channel operably coupled to one or more other suction/injection channels to allow for the injection of gas, liquid, and/or particulate(s) to a target site.

As described in further detail below, when perforated drainage catheter 2100 enters a space in a body, for example a pericardial sac, perforated drainage catheter 2100 may be used to remove fluid by the use of suction through one or more suction/injection apertures 2110. Perforated drainage catheter 2100 may also be used to deliver gas, liquid, and/or particulate(s) to a target site through one or more suction/injection apertures 2110.

Another exemplary embodiment of a portion of a perforated drainage catheter 2100 is shown in FIG. 21B. As shown in FIG. 21B, perforated drainage catheter 2100 comprises a tube with multiple suction/injection apertures 2110. However, in this exemplary embodiment, perforated drainage catheter 2100 comprises a number of concave grooves 2120 extending a portion of a length of perforated drainage catheter 2100, whereby the suction/injection apertures 2110 are provided at the recessed portions therein. Concave grooves 2120, when positioned at least partially around the circumference of perforated drainage catheter 2100, define one or more ridges 2130 extending a portion of a length of perforated drainage catheter 2100. Said ridges 2130 of perforated drainage catheter 2100, when positioned at or near a tissue (not shown), aid to prevent a tissue from coming in direct contact with one or more suction/injection apertures 2110. For example, when perforated drainage catheter 2100 is used in a manner described herein and when a vacuum is coupled to perforated drainage catheter 2100, suction from one or more suction/injection apertures 2110 positioned within one or more concave grooves 2120 would allow for the removal of fluid present in the area of perforated drainage catheter 2100. Ridges 2130 would aid to prevent or minimize tissue adhesion and/or contact with the one or more suction/injection apertures 2110.

A procedure using perforated drainage catheter 2100 may be performed by inserting perforated drainage catheter 2100 into a pericardial sac, following the cardiac surface using, for example, fluoroscopy and/or echodoppler visualization techniques. When perforated drainage catheter 2100 is inserted into a pericardial sac, a pericardial effusion present within the pericardial sac, may be removed by, for example, gentle suction using a syringe. In one example, a 60 cc syringe may be used to remove the effusion with manual gentle suction. When the effusion has been removed, the patients hemodynamic parameters may be monitored to determine the effectiveness of the removal of the effusion. When the pericardial sac is empty, determined by, for example, fluoroscopy or echodoppler visualization, the acute pericardial effusion catheter may be removed, or it may be used for local treatment to introduce, for example, an antibiotic, chemotherapy, or another drug as described below.

Figure 22:
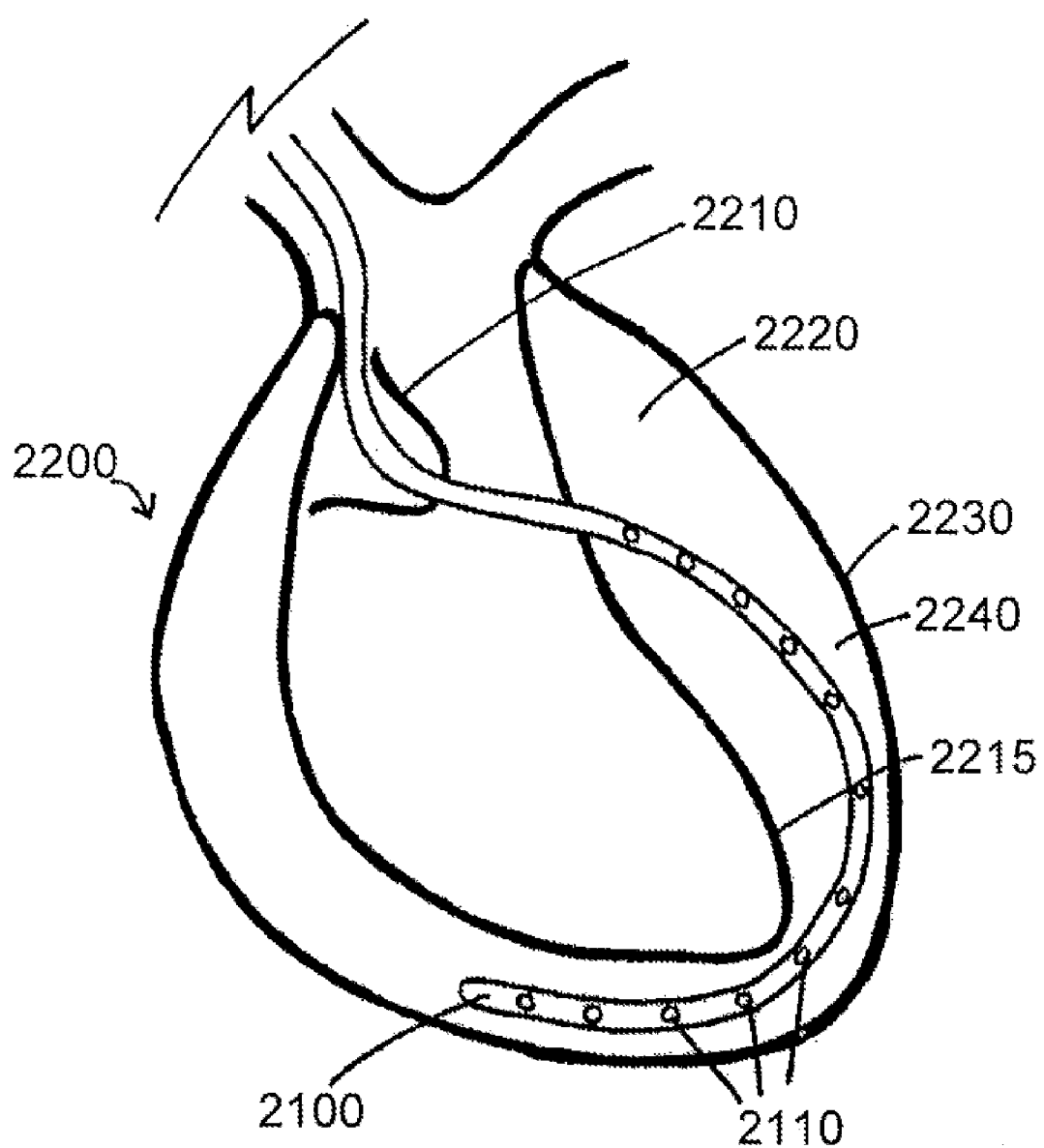
FIG. 22 shows an embodiment of a portion of an apparatus for removing fluid from a tissue inserted within a heart, as disclosed herein.

An exemplary embodiment of a portion of a perforated drainage catheter 2100 present within a pericardial sac is shown in FIG. 22. As shown in FIG. 22, perforated drainage catheter 2100 is first inserted into the heart 2200 using one or more of the techniques and/or procedures described herein, and is placed through the right atrial appendage 2210, the visceral pericardium 2215, and into the pericardial sac 2220. The outer portion of the pericardial sac 2220 is defined by the parietal pericardium 2230. A pericardial effusion 2240 (fluid within the pericardial sac 2220) may then be removed using perforated drainage catheter 2100. When a vacuum source (not shown) is coupled to the proximal end of a portion of a system for removing fluid (comprising, in part, perforated drainage catheter 2100 and one or more other components of a system for engaging a tissue as described herein), the introduction of a vacuum to perforated drainage catheter 2100 allows the pericardial effusion 2240 (the fluid) to be withdrawn from the pericardial sac 2220 into one or more suction/injection apertures 2110 defined along a length of suction/injection apertures 2110.

When perforated drainage catheter 2100 is used to remove some or all of a pericardial effusion (or other fluid present within a space within a body), it may also be used to deliver a gas, liquid, and/or particulate(s) at or near the space where the fluid was removed. For example, the use of perforated drainage catheter 2100 to remove a pericardial effusion may increase the risk of infection. As such, perforated drainage catheter 2100 may be used to rinse the pericardial sac (or other space present within a body) with water and/or any number of beneficial solutions, and may also be used to deliver one or more antibiotics to provide an effective systemic antibiotic therapy for the patient. While the intrapericardial instillation of antibiotics (e.g., gentamycin) is useful, it is typically not sufficient by itself, and as such, it may be combined with general antibiotics treatment for a more effective treatment.

Additional methods to treat neoplastic pericardial effusions without tamponade may be utilized using a device, system and/or method of the present disclosure. For example, a systemic antineoplastic treatment may be performed to introduce drugs to inhibit and/or prevent the development of tumors. If a non-emergency condition exists (e.g., not a cardiac tamponade), a system and/or method of the present disclosure may be used to perform a pericardiocentesis. In addition, the present disclosure allows for the intrapericardial instillation of a cytostatic/sclerosing agent. It can be appreciated that using one or more of the devices, systems and/or methods disclosed herein, the prevention of recurrences may be achieved by intrapericardial instillation of sclerosing agents, cytotoxic agents, or immunomodulators, noting that the intrapericardial treatment may be tailored to the type of the tumor. Regarding chronic autoreactive pericardial effusions, the intrapericardial instillation of crystalloid glucocorticoids could avoid systemic side effects, while still allowing high local dose application.

A pacing lead may be placed on the external surface of the heart using an engagement catheter and a delivery catheter as disclosed herein. For example, an elongated tube of an engagement catheter is extended into a blood vessel so that the distal end of the tube is in contact with a targeted tissue on the interior of a wall of the heart. As explained above, the targeted tissue may be on the interior of the atrial wall or the atrial appendage. Suction is initiated to aspirate a portion of the targeted tissue to retract the cardiac wall away from the pericardial sac that surrounds the heart, thereby enlarging a pericardial space between the pericardial sac and the cardiac wall. A needle is then inserted through a lumen of the tube and advanced to the heart. The needle is inserted into the targeted tissue, causing a perforation of the targeted tissue. The distal end of a guide wire is inserted through the needle into the pericardial space to secure the point of entry through the cardiac wall. The needle is then withdrawn from the targeted tissue.

A delivery catheter, as described herein, is inserted into the lumen of the tube of the engagement catheter and over the guide wire. The delivery catheter may be a 14 Fr. radiopaque steering catheter. The distal end of the delivery catheter is advanced over the guide wire through the targeted tissue into the pericardial space. Once in the pericardial space, the delivery catheter is directed using a steering wire system as disclosed herein. In addition, a micro-camera system may be extended through the lumen of the delivery catheter to assist in the direction of the delivery catheter to the desired location in the pericardial space. Micro-camera systems suitable for use with the delivery catheter are well-known in the art. Further, a laser Doppler system may be extended through the lumen of the delivery catheter to assist in the direction of the delivery catheter. The delivery catheter is positioned such that the outlet of one of the lumens of the delivery catheter is adjacent to the external surface of the heart (e.g., the external surface of an atrium or a ventricle). A pacing lead is extended through the lumen of the delivery catheter onto the external surface of the heart. The pacing lead may be attached to the external surface of the heart, for example, by screwing the lead into the cardiac tissue. In addition, the pacing lead may be placed deeper into the cardiac tissue, for example in the subendocardial tissue, by screwing the lead further into the tissue. After the lead is placed in the proper position, the delivery catheter is withdrawn from the pericardial space and the body. The guide wire is withdrawn from the pericardial space and the body, and the engagement catheter is withdrawn from the body.

The disclosed embodiments can be used for subendocardial, as well as epicardial, pacing. While the placement of the leads is epicardial, the leads can be configured to have a long screw-like tip that reaches near the subendocardial wall. The tip of the lead can be made to be conducting and stimulatory to provide the pacing to the subendocardial region. In general, the lead length can be selected to pace transmurally at any site through the thickness of the heart wall. Those of skill in the art can decide whether epicardial, subendocardial, or some transmural location stimulation of the muscle is best for the patient in question.

While various embodiments of devices, systems, and methods for accessing the heart tissue have been described in considerable detail herein, the embodiments are merely offered by way of non-limiting examples of the disclosure described herein. Many variations and modifications of the embodiments described herein will be apparent to one of ordinary skill in the art in light of this disclosure. For example and without limitation, the devices, systems and methods may be modified and employed as described in U.S. patent application Ser. No. 12/596,972 to Kassab et al, and U.S. patent application Ser. No. 12/596,970 to Kassab et al., both of which are incorporated by reference herein in their entireties. It will therefore be understood by those skilled in the art that various changes and modifications may be made, and equivalents may be substituted for elements thereof, without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

We claim:

1. A system for obtaining a tissue sample from a targeted tissue, the system comprising:
a first catheter having a proximal end, distal end, and an interior, the distal end of the first catheter comprising a cutting portion adapted to cut a targeted biological tissue;
a second catheter slidably received within the interior of the first catheter, the second catheter having a proximal end, an interior, a distal end adapted to puncture the targeted tissue, and an opening disposed proximal to the distal end of the second catheter and in communication with the interior of the second catheter;
a torque mechanism comprising at least one dial coupled with at least one shaft, the at least one dial configured for rotational movement and the at least one shaft adapted to convert the rotational movement of the at least one dial into linear movement of the at least one shaft, the at least one shaft coupled with the first catheter such that the at least one shaft is adapted to advance and retract the first catheter, and the at least one shaft coupled with the second catheter such that the at least one shaft is adapted to advance and retract the second catheter; and
a deliver catheter comprising an elongated tube having a proximal end, a distal end, a wall, and a first lumen and a second lumen, the delivery catheter adapted for at least partial intravascular insertion into a mammalian body, and the at least one lumen of the delivery catheter extending from approximately the proximal end of the tube to or near the distal end of the tube and comprising a bend relative to the tube at or near the distal end of the tube and an outlet through the wall of the tube at or near the distal end of the tube, the first and second lumens each extending from approximately the proximal end of the tube to or near the distal end of the tube, each positioned longitudinally adjacent to each other, and each comprising a bend relative to the tube at or near the distal end of the tube and an outlet through the wall of the tube at or near the distal end of the tube, the first lumen of the delivery catheter having the catheter slidably disposed therein, and the second lumen of the delivery catheter having a navigational tool disposed therein, the navigational tool configured to be advanceable through the outlet of the second lumen.

2. The system of claim 1, further comprising at least one limiter device coupled with the at least one shaft of the torque mechanism and adapted to prevent the second catheter from advancing farther than a specified distance.

3. The system of claim 1, wherein the torque mechanism comprises a first shaft coupled with the proximal end of the first catheter and a second shaft coupled with the proximal end of the second catheter.

4. The system of claim 3, further comprising:
a first limiter device coupled with the first shaft and adapted to prevent the first catheter from advancing farther than a first distance; and
a second limiter device coupled with the second shaft and capable of adapted to prevent the second catheter from advancing farther than a second distance.

5. The system of claim 1, wherein the distal end of the second catheter comprises a hollow needle.

6. The system of claim 1, wherein the first and second catheters comprise a semi-rigid material.

7. The system of claim 1, wherein the cutting portion of the first catheter comprises a metallic cylinder having a cutting edge.

8. The system of claim 1, wherein the at least one shaft comprises a leadscrew.

9. The system of claim 1, wherein the at least one dial is adapted for segmented rotational movement and the at least one shaft is configured to convert the segmented rotational movement of the at least one dial into a defined amount of linear movement of the second catheter.

10. The system of claim 9, wherein the defined amount of linear movement comprises about 1 mm.

11. The system of claim 3, wherein a first dial is coupled with the first shaft and a second dial is coupled with the second shaft, the first dial and the second dial each adapted for segmented rotational movement, the first shaft configured to convert the segmented rotational movement of the first dial into a defined amount of linear movement of the first catheter, and the second shaft of configured to convert the segmented rotational movement of the second dial into a defined amount of linear movement of the second catheter.

12. The system of claim 1, wherein the targeted tissue is a mammalian heart.

13. The system of claim 1, wherein the system is capable of intravascular insertion.

14. The system of claim 1, wherein the distal end of the second catheter comprises a tapered configuration.

15. The system of claim 1, wherein the proximal end of the first catheter is coupled with a handle.

16. The system of claim 1, further comprising at least one suction port in communication with either the interior of the first catheter, the interior of the second catheter, or both, the at least one suction port adapted for operative connection to a vacuum source.

17. A system for accessing a targeted tissue and obtaining a tissue sample therefrom, the system comprising:
a delivery catheter comprising an elongated tube having a proximal end, a distal end, a wall, and a first lumen and a second lumen, the delivery catheter adapted for at least partial intravascular insertion into a mammalian body, and the at least one lumen of the deliver catheter extending from approximately the proximal end of the tube to or near the distal end of the tube and comprising a bend relative to the tube at or near the distal end of the tube and an outlet through the wall of the tube at or near the distal end of the tube, the first and second lumens each extending from approximately the proximal end of the tube to or near the distal end of the tube, each positioned longitudinally adjacent to each other, and each comprising a bend relative to the tube at or near the distal end of the tube and an outlet through the wall of the tube at or near the distal end of the tube; and a biopsy system slidably disposed within the at least one lumen of the delivery catheter, the biopsy system comprising:
a first catheter having a proximal end, a distal end, and an interior extending between the proximal end and the distal end, and the distal end of the first catheter comprising a cutting portion adapted biological tissue,
a second catheter slidably received within the interior of the first catheter, the second catheter having a proximal end, a distal end, and an interior extending between the proximal end and the distal end, and the distal end of the second catheter comprising a tapered configuration configured to puncture the targeted tissue and an opening in communication with the interior of the second catheter, and
a torque mechanism comprising at least one dial coupled with a first shaft and at least one dial coupled with a second shaft, each of the at least one dials configured for rotational movement and the respective shaft adapted to convert the rotational movement of the at least one dial into linear movement of the respective shaft, the first shaft of the torque mechanism coupled with the first catheter such that the first shaft of the torque mechanism is adapted to advance and retract the first catheter, and the second shaft coupled with the second catheter such that the second shaft is adapted to advance and retract the second catheter;
the first lumen of the delivery catheter having the biopsy system slidably disposed therein, and the second lumen of the delivery catheter having a navigational tool disposed therein, the navigational tool configured to be advanceable through the outlet of the second lumen.

18. The system of claim 17, wherein the at least one lumen of the delivery catheter further comprises a third lumen, the third lumen extending from approximately the proximal end of the tube to or near the distal end of the tube, positioned longitudinally adjacent to the first and second lumens, and comprising a steering wire system disposed therein, the steering wire system configured to facilitate the navigation of the delivery catheter through vasculature of the body.

19. The system of claim 18, wherein a guide wire is disposed within the third lumen of the delivery catheter.

20. The system of claim 18, wherein each of the steering wire system, the navigational tool and the biopsy system may be independently controlled by a user.

21. The system of claim 17, wherein the targeted tissue is an epicardial surface of a mammalian heart.

22. The system of claim 17, wherein the navigational tool is selected from the group consisting of a laser Doppler tip, an endo-camera, and a micro-camera.

23. A method of engaging a tissue and retrieving a tissue sample therefrom, the method comprising the steps of:
inserting into a blood vessel an elongated tube having a proximal end, a distal end, and a first lumen, such that the distal end of the tube is in contact with a first targeted biological tissue on an interior wall of a mammalian heart;
accessing the pericardial space through the first targeted tissue;
inserting at least a distal end of a delivery catheter into the first lumen of the tube, the delivery catheter comprising at least a first lumen comprising a bend at or near the distal end of the delivery catheter and an outlet at or near the distal end of the delivery catheter;
advancing at least the distal end of the delivery catheter through the first targeted tissue and into the pericardial space such that the distal end of the delivery catheter is positioned at or near a second targeted biological tissue;

inserting at least a portion of a biopsy system into the at least one lumen of the delivery catheter, the biopsy system comprising a first catheter and a second catheter, the first catheter of the biopsy system comprising a distal end having a cutting portion, an outlet disposed at or near the distal end, and an interior in communication with the outlet, the second catheter of the biopsy system slidably disposed within the interior of the first catheter and comprising an interior, a distal end adapted to puncture the second targeted tissue and an opening disposed at or near the distal end of the second catheter and in communication with the interior of the second catheter;

advancing the first and second catheters of the biopsy system through the outlet of the first lumen of the delivery catheter such that the distal ends of the first and second catheters are positioned at or near the second targeted tissue;

piercing the second targeted tissue with the second catheter of the biopsy system; and collecting a sample of the second targeted tissue into the opening of the second catheter of the biopsy system.

24. The method of claim 23, wherein the second targeted tissue comprises an epicardial surface of a mammalian heart.

25. The method of claim 24, wherein the delivery catheter further comprises a second lumen, the second lumen of the delivery catheter comprising a bend at or near the distal end of the delivery catheter and an outlet at or near the distal end of the delivery catheter, and further comprising the steps of inserting at least a distal end of a navigational tool into the second lumen of the delivery catheter and locating the second targeted tissue.

26. The method of claim 24, further comprising the step of aspirating the second targeted tissue such that the distal end of the first catheter is reversibly coupled therewith.

27. The method of claim 23, wherein the biopsy system further comprises a torque mechanism comprising at least one dial coupled with at least one shaft, the at least one dial configured for rotational movement about the at least one shaft and the at least one shaft adapted to convert the rotational movement of the at least one dial into linear movement of the first catheter of the biopsy system, the second catheter of the biopsy system or both, and the step of piercing the second targeted tissue with the second catheter of the biopsy system further comprises operating the torque mechanism of the biopsy system to advance the distal end of the second catheter a first distance into the second targeted tissue.

28. The method of claim 27, further comprising the step of advancing the first catheter through operation of the torque mechanism such that the cutting portion of the first catheter cuts a sample of the second targeted tissue.

29. The method of claim 28, further comprising the step of aspirating the second targeted tissue such that the sample of the second targeted tissue is pulled into the interior of the second catheter through the opening of the second catheter and detached from the remaining second targeted tissue.

30. The method of claim 29, further comprising the step of withdrawing the first catheter and the second catheter containing the sample of the second targeted tissue.

31. The method of claim 27, further comprising the step of advancing the first catheter a second distance through operation of the torque mechanism such that the cutting portion of the first catheter cuts the second targeted tissue, and wherein the first distance and the second distance are substantially equal.

32. A system for obtaining a tissue sample from a targeted tissue, the system comprising:

a catheter having a proximal end, distal end, and an interior extending between the proximal and distal ends, the distal end comprising a tapered configuration, a cutting edge capable of slicing a targeted biological tissue, and an opening in communication with the interior of the catheter;

a torque mechanism coupled with the proximal end of the catheter, the torque mechanism comprising at least one dial coupled with at least one shaft, the at least one dial being configured for rotational movement and the at least one shaft adapted to convert the rotational movement of the at least one dial into either linear movement of the catheter or rotational movement of the catheter, and rotation of the catheter in a first direction causes the cutting edge of the catheter to slice a sample of a targeted tissue and wherein the cutting edge and the opening are configured to allow the sample to be drawn through the opening and into the interior of the catheter; and a delivery catheter comprising an elongated tube having a proximal end, a distal end, a wall, and a first lumen and a second lumen, the delivery catheter adapted for at least partial intravascular insertion into a mammalian body, and the at least one lumen of the delivery catheter extending from approximately the proximal end of the tube to or near the distal end of the tube and comprising a bend relative to the tube at or near the distal end of the tube and an outlet through the wall of the tube at or near the distal end of the tube, the first and second lumens each extending from approximately the proximal end of the tube to or near the distal end of the tube, each positioned longitudinally adjacent to each other, and each comprising a bend relative to the tube at or near the distal end of the tube and an outlet through the wall of the tube at or near the distal end of the tube, the first lumen of the delivery catheter having the catheter slidably disposed therein, and the second lumen of the delivery catheter having a navigational tool disposed therein, the navigational tool configured to be advanceable through the outlet of the second lumen.

33. The system of claim 32, wherein the at least one lumen of the delivery catheter further comprises a third lumen, the third lumen extending from approximately the proximal end of the tube to or near the distal end of the tube and comprising a steering wire system disposed therein, the steering wire system configured to facilitate the navigation of the delivery catheter through vasculature of the body.

34. The system of claim 33, wherein a guide wire is disposed within the third lumen of the delivery catheter.

35. The system of claim 33, wherein each of the steering wire system, the navigational tool and the biopsy system may be independently controlled by a user.

36. The system of claim 32, further comprising a suction port in communication with the interior of the catheter, the suction port adapted for operative connection to a vacuum source.

37. The system of claim 32, wherein the distal end of the catheter further comprises a first edge and a second edge, the first edge and the second edge configured in a tapered configuration such that the first edge overlaps the second edge and the opening is formed therebetween.

38. The system of claim 32, wherein the distal end of the catheter is comprised of a metallic material.

39. The system of claim 32, further comprising at least one limiter device coupled with the at least one shaft of the torque mechanism and adapted to prevent the catheter from advancing farther than a specified distance.

40. The system of claim 32, wherein the proximal end of the catheter is coupled with a handle.

41. The system of claim 32, wherein the targeted tissue is an epicardial surface of a mammalian heart.

42. The system of claim 32, wherein the navigational tool is selected from the group consisting of a laser Doppler tip, an endo-camera, and a micro-camera.

43. A method of retrieving a tissue sample from a body, the method comprising the steps of:
- inserting into a blood vessel an elongated tube having a proximal end, a distal end, and a first lumen, such that the distal end of the tube is in contact with a first targeted biological tissue on an interior wall of a mammalian heart;
- accessing a pericardial space of the heart through the first targeted tissue;
- inserting at least a distal end of a delivery catheter into the first lumen of the tube, the delivery catheter comprising at least one lumen comprising a bend at or near the distal end of the delivery catheter and an outlet at or near the distal end of the delivery catheter;
- advancing at least the distal end of the delivery catheter through the first targeted tissue and into the pericardial space such that the distal end of the delivery catheter is positioned at or near a second targeted biological tissue;
- inserting at least a portion of a biopsy system into the at least one lumen of the delivery catheter, the biopsy system comprising a catheter comprising a distal end having a tapered configuration, a cutting edge configured to slice the second targeted tissue and an opening in communication with the interior of the catheter;
- advancing the catheter of the biopsy system through the outlet of the first lumen of the delivery catheter such that the distal end of the catheter is positioned at or near the second targeted tissue;
- piercing the second targeted tissue with distal end of the catheter; and
- rotating the distal end of the catheter such that the cutting edge slices the second targeted tissue, detaches a sample thereof and draws the sample into the interior of the catheter.

44. The method of claim 43, wherein the biopsy system further comprises a torque mechanism coupled with the catheter and comprising at least one dial coupled with at least one shaft, the at least one dial configured for rotational movement relative to the respective shaft and each of the at least one shafts adapted to convert the rotational movement of the respective dial into either linear movement of the catheter or rotational movement of the catheter, and wherein the step of piercing the second targeted tissue with the distal end of the catheter further comprises rotating the a first dial of a torque mechanism to advance the distal end of the catheter a first distance into the second targeted tissue.

45. The method of claim 44, wherein the step of rotating the distal end of the catheter further comprises rotating a second dial of the torque mechanism.

46. The method of claim 43, wherein:
- the at least one lumen of the delivery catheter comprises a first lumen and a second lumen, the first and second lumens each extending from approximately the proximal end of the delivery catheter to or near the distal end of the delivery catheter, each positioned longitudinally adjacent to each other, and each comprising a bend at or near the distal end of the delivery catheter, the first lumen of the delivery catheter having a biopsy system slidably disposed therein, and the second lumen of the delivery catheter having a navigational tool disposed therein, the navigational tool adapted to be advanceable through the outlet of the second lumen; and
- the method further comprising the step of operating the navigational tool to locate the second targeted tissue on the epicardial surface of the heart.

47. The method of claim 43, further comprising the step of aspirating the second targeted tissue such that the distal end of the catheter is reversibly coupled with the second targeted tissue.

48. The method of claim 43, further comprising the step of operating a vacuum source operatively coupled with the interior of the catheter to facilitate retention of the sample within the interior of the catheter.

49. The method of claim 43, further comprising the step of withdrawing the catheter containing the sample.

\* \* \* \* \*